United States Patent
Loutherback et al.

(10) Patent No.: US 11,666,912 B2
(45) Date of Patent: Jun. 6, 2023

(54) SORTING OF T LYMPHOCYTES IN A MICROFLUIDIC DEVICE

(71) Applicant: Berkeley Lights, Inc., Emeryville, CA (US)

(72) Inventors: Kevin D. Loutherback, Berkeley, CA (US); Yelena Bronevetsky, San Francisco, CA (US); Peter J. Beemiller, Emeryville, CA (US); Xiaohua Wang, Albany, CA (US); Kevin T. Chapman, Santa Monica, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 1142 days.

(21) Appl. No.: 16/253,869

(22) Filed: Jan. 22, 2019

(65) Prior Publication Data
US 2019/0283026 A1    Sep. 19, 2019

Related U.S. Application Data

(63) Continuation of application No. PCT/US2017/043395, filed on Jul. 21, 2017.
(Continued)

(51) Int. Cl.
*B01L 3/00* (2006.01)
*A61K 35/17* (2015.01)
(Continued)

(52) U.S. Cl.
CPC ........ *B01L 3/502746* (2013.01); *A61K 35/17* (2013.01); *A61K 35/28* (2013.01);
(Continued)

(58) Field of Classification Search
CPC ... G01N 2015/0065; G01N 2015/1081; G01N 2015/1006; G01N 2015/1056;
(Continued)

(56) References Cited

U.S. PATENT DOCUMENTS

| 6,294,063 B1 | 9/2001 | Becker et al. |
| 6,942,776 B2 | 9/2005 | Medoro |

(Continued)

FOREIGN PATENT DOCUMENTS

| CN | 101275114 A | 10/2008 |
| CN | 101346463 A | 1/2009 |

(Continued)

OTHER PUBLICATIONS

Berger et al., "Design of a microfabricated magnetic cell separator" Electrophoresis 2001, 22, 3883-3892.
(Continued)

*Primary Examiner* — Joseph C Rodriguez
(74) *Attorney, Agent, or Firm* — Barnes & Thornburg LLP; Kenneth E. Horton

(57) ABSTRACT

Methods of sorting T lymphocytes in a microfluidic device are provided. The methods can include flowing a fluid sample comprising T lymphocytes through a region of a microfluidic device that contains an array of posts. The array of posts can be configured to have a critical size ($D_c$) that separates activated T lymphocytes from naïve T lymphocytes. Also provided are microfluidic devices having an array of posts configured to separate activated T lymphocytes from naïve T lymphocytes, compositions enriched for T lymphocytes, particularly activated T lymphocytes that are known to be reactive to an antigen of interest, and methods of treating subjects suffering from a pathogenic disorder or cancer by administering such compositions.

25 Claims, 14 Drawing Sheets

Related U.S. Application Data

(60) Provisional application No. 62/365,372, filed on Jul. 21, 2016.

(51) Int. Cl.
| | |
|---|---|
| *G01N 1/34* | (2006.01) |
| *B03C 5/02* | (2006.01) |
| *A61K 35/28* | (2015.01) |
| *B03C 5/00* | (2006.01) |
| *G01N 1/40* | (2006.01) |

(52) U.S. Cl.
CPC ... *B01L 3/502761* (2013.01); *B01L 3/502792* (2013.01); *B03C 5/005* (2013.01); *B03C 5/026* (2013.01); *G01N 1/34* (2013.01); *B01L 3/502784* (2013.01); *B01L 2200/0652* (2013.01); *B01L 2300/0645* (2013.01); *B01L 2300/0816* (2013.01); *B01L 2300/12* (2013.01); *B01L 2300/165* (2013.01); *B01L 2400/0424* (2013.01); *B01L 2400/086* (2013.01); *B03C 2201/26* (2013.01); *G01N 2001/4088* (2013.01)

(58) Field of Classification Search
CPC ............ G01N 15/1484; G01N 15/149; G01N 15/1493; G01N 27/44791; G01N 30/6095; G01N 1/34; B01L 3/502715; B01L 3/502766; B01L 3/502769; B01L 3/502746; B01L 3/502761; B01L 3/502792; B03C 5/005; B03C 5/26; A61K 35/17; A61K 35/28
See application file for complete search history.

(56) References Cited

U.S. PATENT DOCUMENTS

| | | |
|---|---|---|
| 7,090,759 B1 | 8/2006 | Seul |
| 8,581,167 B2 | 11/2013 | Lean et al. |
| 9,144,806 B2 | 9/2015 | Chen et al. |
| 2003/0008364 A1 | 1/2003 | Wang et al. |
| 2004/0072278 A1 | 4/2004 | Chou et al. |
| 2004/0191789 A1 | 9/2004 | Manaresi et al. |
| 2004/0197905 A1 | 10/2004 | Hafeman |
| 2005/0112548 A1 | 5/2005 | Segawa et al. |
| 2005/0129581 A1 | 6/2005 | Mcbride et al. |
| 2005/0175981 A1 | 8/2005 | Voldman et al. |
| 2006/0091015 A1 | 5/2006 | Lau |
| 2006/0154361 A1 | 7/2006 | Wikswo et al. |
| 2006/0263612 A1 | 11/2006 | Chen et al. |
| 2007/0095669 A1 | 5/2007 | Lau et al. |
| 2007/0183934 A1 | 8/2007 | Diercks et al. |
| 2008/0013092 A1 | 1/2008 | Maltezos et al. |
| 2008/0023399 A1 | 1/2008 | Inglis et al. |
| 2008/0223721 A1 | 9/2008 | Cohen et al. |
| 2008/0302732 A1 | 12/2008 | Soh et al. |
| 2009/0023608 A1 | 1/2009 | Hung et al. |
| 2009/0098541 A1 | 4/2009 | Southern et al. |
| 2009/0170186 A1 | 7/2009 | Wu et al. |
| 2010/0003666 A1 | 1/2010 | Lee et al. |
| 2010/0101960 A1 | 4/2010 | Ohta et al. |
| 2010/0273681 A1 | 10/2010 | Cerrina et al. |
| 2011/0020459 A1 | 1/2011 | Achrol et al. |
| 2011/0053151 A1 | 3/2011 | Hansen et al. |
| 2011/0117634 A1 | 5/2011 | Halamish et al. |
| 2011/0143964 A1 | 6/2011 | Zhou et al. |
| 2011/0186165 A1 | 8/2011 | Borenstein et al. |
| 2011/0262906 A1 | 10/2011 | Dimov et al. |
| 2012/0009671 A1 | 1/2012 | Hansen et al. |
| 2012/0015347 A1 | 1/2012 | Singhal et al. |
| 2012/0118740 A1 | 5/2012 | Garcia et al. |
| 2012/0156675 A1 | 6/2012 | Lueerssen et al. |
| 2012/0325665 A1 | 12/2012 | Chiou et al. |
| 2013/0115606 A1 | 5/2013 | Hansen et al. |
| 2013/0118905 A1 | 5/2013 | Morimoto et al. |
| 2013/0130232 A1 | 5/2013 | Weibel et al. |
| 2013/0146459 A1 | 6/2013 | Bazant et al. |
| 2013/0171628 A1 | 7/2013 | Di Carlo et al. |
| 2013/0190212 A1 | 7/2013 | Handique et al. |
| 2013/0204076 A1 | 8/2013 | Han et al. |
| 2013/0261021 A1 | 10/2013 | Bocchi et al. |
| 2014/0030788 A1 | 1/2014 | Chen et al. |
| 2014/0116881 A1 | 5/2014 | Chapman et al. |
| 2014/0124370 A1 | 5/2014 | Short et al. |
| 2015/0018226 A1 | 1/2015 | Hansen et al. |
| 2015/0151298 A1* | 6/2015 | Hobbs ............... B01L 3/502761 |
| | | 435/7.1 |
| 2015/0151307 A1 | 6/2015 | Breinlinger et al. |
| 2015/0165436 A1 | 6/2015 | Chapman et al. |
| 2016/0047735 A1 | 2/2016 | Grisham et al. |
| 2016/0139012 A1 | 5/2016 | Dsilva et al. |
| 2016/0184821 A1 | 6/2016 | Hobbs et al. |
| 2016/0199837 A1 | 7/2016 | Breinlinger et al. |
| 2016/0252495 A1 | 9/2016 | Ricicova et al. |
| 2016/0312165 A1 | 10/2016 | Lowe, Jr. et al. |
| 2018/0298318 A1 | 10/2018 | Kurz et al. |
| 2019/0240665 A1 | 8/2019 | Lioberger et al. |
| 2019/0275516 A1 | 9/2019 | Lowe, Jr. et al. |
| 2020/0025669 A1* | 1/2020 | Ward ............... B01L 3/502715 |

FOREIGN PATENT DOCUMENTS

| | | | |
|---|---|---|---|
| CN | 101351546 | A | 1/2009 |
| CN | 102119214 | A | 7/2011 |
| CN | 104838273 | A | 8/2015 |
| EP | 3487510 | A1 | 5/2019 |
| JP | 2004-500095 | A | 1/2004 |
| JP | 2007537729 | A | 12/2007 |
| JP | 2012522518 | A | 9/2012 |
| KR | 1020030032922 | A | 4/2003 |
| KR | 1020109008222 | A | 1/2010 |
| WO | 2001/062895 | A2 | 8/2001 |
| WO | 2002088702 | A2 | 11/2002 |
| WO | 2005100541 | A2 | 10/2005 |
| WO | 2006108101 | A2 | 10/2006 |
| WO | 2008119066 | A1 | 10/2008 |
| WO | 2008131048 | A2 | 10/2008 |
| WO | 2010115167 | A2 | 10/2010 |
| WO | 2010147078 | A1 | 12/2010 |
| WO | 2012037030 | A2 | 3/2012 |
| WO | 2012072823 | A1 | 6/2012 |
| WO | 2013019491 | A1 | 2/2013 |
| WO | 2015058206 | A1 | 4/2015 |
| WO | 2017106958 | A1 | 6/2017 |
| WO | 2018018017 | A1 | 1/2018 |

OTHER PUBLICATIONS

Chiou et al., "Massively parallel manipulation of single cells and microparticles using optical images," Nature, vol. 436 (Jul. 21, 2005), pp. 370-372.

Chiou, "Massively Parallel Optical Manipulation of Cells, Micro- and Nano-Particles on Optoelectronic devices", Dissertation, University of California at Berkeley, 2005 (147 pages).

Chung et al., "Imaging Single-Cell Signaling Dynamics with a Deterministic High-Density Single-Cell Trap Array", Anal. Chem. 83(18):7044-7052 (2011).

CN101275114A, Machine Translation, Oct. 1, 2008, 8 pages.

Hsu et al., "Sorting of Differentiated Neurons Using Phototransistor-Based Optoelectronic Tweezers for Cell Replacement Therapy of Neurodegenerative Diseases", Transducers 2009, Denver, CO USA Jun. 2009, download dated Nov. 23, 2009 from IEEE Xplore, 4 pages.

Hung et al., "Continuous Perfusion Microfluidic Cell Culture Array for High-Throughput Cell-Based Assays", Biotech and Bioengineering 89(1): 1-8 (2004). Dec. 3, 2004.

Iliescu et al., "Continuous Field-Flow Separation of Particle Populations in a Dielectrophoretic Chip with Three Dimensional Electrodes", Applied Physics Letters 90:234104 (2007).

(56) References Cited

OTHER PUBLICATIONS

KR1020100008222A (KIPO computer-generated English language translation), Jan. 25, 2010, 10 pages.

Lee et al. "Separation and sorting of cells in microsystems using physical principles", Journal of Micromechanics & Microengineering, Institute of Physics Publishing, Bristol, GB, vol. 26, No. 1, Dec. 16, 2015 (Dec. 16, 2015), pp. 1-15.

Maheswaran et al. "Ex Vivo Culture of CTCs: An Emerging Resource to Guide Cancer Therapy", Cancer Research 75(12) (2015).

Nevill et al., "Integrated microfluidic cell culture and lysis on a chip", Lab on a Chip 7:1689-95 (2007).

Sajeesh et al., "Particle separation and sorting in microfluidic devices: a review" Microfluid Nanofluid (2014) vol. 17, pp. 1-52.

Somaweera et al., "Generation of a Chemical Gradient Across an Array of 256 Cell Cultures in a Single Chip", Analyst, Oct. 7, 2013, vol. 138, No. 19, pp. 1-14.

Valley et al., "Optoelectronic Tweezers as a Tool for Parallel Single-Cell Manipulation and Stimulation", IEEE Transactions on Biomedical Circuits and Systems, vol. 3, No. 6 (Dec. 2009), pp. 424-431.

WO2010147078, Machine Translation, Dec. 23, 2010, 12 pages.

Xu et al,. "Recent Trends in Dielectrophoresis", Informacije MIDEM, 2010, vol. 40, Issue No. 4, pp. 253-262.

Yi et al., "Microfluidics technology for manipulation and analysis of biological cells," Analytica Chimica Acta 560 (2006), pp. 1-23.

Nguyen H.H. et al., Naive CD8+T cell derived tumor-specific cytotoxic effectors as a potential remedy for overcoming TGF-β immunosuppression in the tumor microenvironment. Scientific Reports, Jun. 16, 2016, vol. 6, pp. 10.

Written Opinion of Intellectual Property Office of Singapore, Application No. 11201900442P (dated Jun. 4, 2020).

Ingles et al., Determining blood cell size using microfluidic hydrodynamics, Journal of Immunological Methods 329 (2008) pp. 151-156.

Inglis et al., "Critical particle size for fractionation by deterministic lateral displacement", Lab On A Chip, vol. 6, No. 5, Jan. 1, 2006 (Jan. 1, 2006), p. 655.

European Patent Office, Supplementary Search Report, Application Serial No. 17831997.6, dated Jan. 24, 2020 (7 pages).

The International Search Report and Written Opinion of the International Searching Authority, PCT Application Serial No. PCT/US17/43395 (dated Nov. 13, 2017) 12 pages.

\* cited by examiner

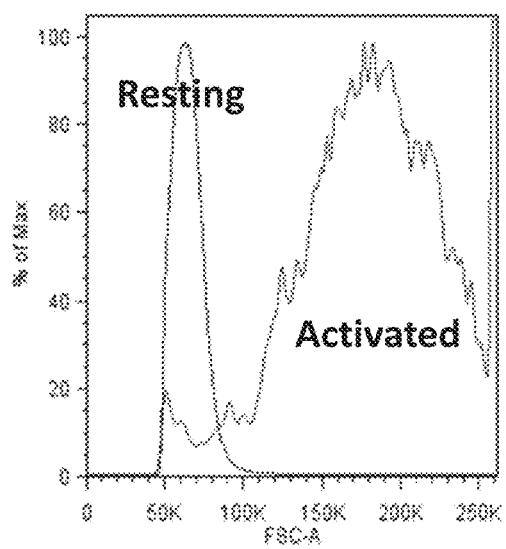
FIG. 9A
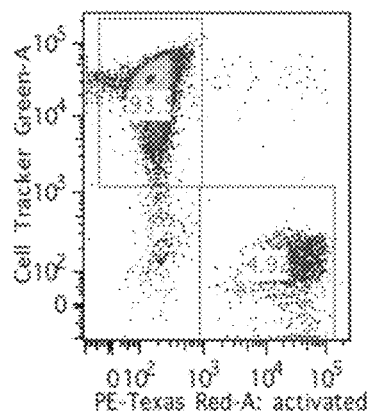   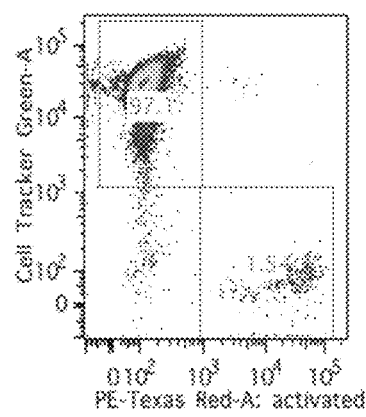   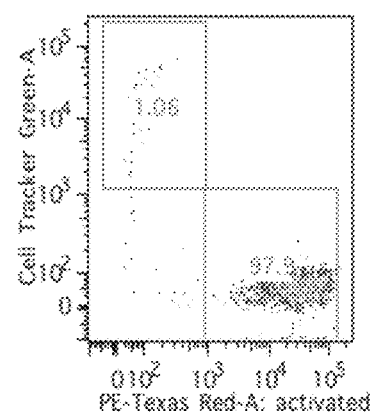
FIG. 9B          FIG. 9C          FIG. 9D

SORTING OF T LYMPHOCYTES IN A MICROFLUIDIC DEVICE

CROSS REFERENCE TO RELATED APPLICATIONS

This application claims the benefit under 35 U.S.C. § 119 of U.S. Patent Application No. 62/365,372, filed on Jul. 21, 2016, the entire disclosure of each of which is incorporated herein by reference.

FIELD OF THE INVENTION

The field generally relates to methods, systems and devices for sorting T lymphocytes, particularly activated T lymphocytes, within a microfluidic environment.

BACKGROUND OF THE INVENTION

Immunotherapy is the burgeoning field of using a patient's own immune system to help fight cancer. A variety of immunotherapy strategies have been evaluated, including stimulating the patient's own immune system to attack cancer cells or administering immune system components from an external source. For example, monoclonal antibodies designed to attack cancer cells in vivo have been administered alone or in genetically engineered constructs. In addition, various T cell therapies have been investigated. Autologous T cell therapies involve obtaining T cells from a subject, expanding the T cells ex vivo, and reintroducing the expanded T cells into the subject. Chimeric antigen receptor T cell (CAR-T) therapies involve genetically engineering T cells to express chimeric antibody-containing fusion proteins on their surface which target the cancer in question and allows for the T cells to kill the cancer cells. Both types of T cell therapies offer advantages. However, the therapies still require further refinement.

One of the key problems in both autologous T cell therapies and CAR-T therapies is the lack of methods for selecting T cells ex vivo in a manner that generates a population of T cells having the highest tumor killing potential. The present embodiments offer a solution for sorting T cells ex vivo to obtain populations enriched for T cells having a desirable phenotype. The present embodiments also provide microfluidic devices that facilitate such sorting and compositions obtained therefrom.

SUMMARY OF THE INVENTION

In one aspect, methods of sorting T lymphocytes in a microfluidic device, based on the size of the T lymphocytes, are provided. The methods can include producing a sample enriched for activated T lymphocytes that specifically recognize an antigen of interest. The microfluidic device can include a flow path having a first region that comprises a first array of posts. The first region can be a channel (e.g., a main channel), and the first array of posts can extend across the entire width of the channel. The method includes flowing a fluid sample containing T lymphocytes through the first region of the flow path (or channel) of the microfluidic device, and thus through the first array of posts.

The first array can be characterized by a critical size ($D_c$) of about 4 microns to about 10 microns. The posts of the first array can be arranged in rows and columns, with the rows of posts defining a first array direction that differs from a first direction of the first region by a tilt angle ($\varepsilon$), where the first direction of the first region is defined by the general direction that fluid flows through the first region. The columns of posts in the first array can repeat periodically with a periodicity equal to $1/\varepsilon$, where $\varepsilon$ is measured in radians. Adjacent posts in each respective column in the first array define gaps through which fluid can flow, generally transversely with respect to the columns. The columns of posts can be arranged substantially transversely with respect to the first direction of the first region (e.g., each column of posts can be arranged along an axis that is oriented about 80° to about 100° relative to the first direction of the first region) or, more generally, the columns of posts can be arranged along an axis that is oriented about 45° to about 135° relative to the first direction of the first region.

The fluid sample containing T lymphocytes can include, for example, $CD8^+$ T lymphocytes. The fluid sample can be derived from a starting population of T lymphocytes that has been incubated with an activating agent which comprises an antigen of interest. The activating agent can be, for example, dendritic cells (DCs) or artificial antigen presenting cells (aAPCs). The starting population of T lymphocytes can be obtained from, for example, peripheral blood or PBMCs. Optionally, the starting population of T lymphocytes can be enriched for naïve T cells (e.g., $CD8^+$ naïve T cells). For example, the starting population of T lymphocytes can contain 30%, 40%, 50%, 60%, 70%, 80%, 90%, or more naïve T cells (e.g., 30%, 40%, 50%, 60%, 70%, 80%, 90%, or more naïve $CD8^+$ T cells).

The methods can be used, for example, to identify T cells having TCRs that are specific to an antigen of interest. The antigen of interest can be a peptide sequence derived from a pathogen, such as a bacterial pathogen, a fungal pathogen, a parasitic pathogen, or a viral pathogen. Alternatively, the antigen of interest can be a peptide sequence that is a tumor-associated antigen. The identified T cells can be cloned and a subset of cells from one or more such clones can be used for TCR sequencing analysis. Alternatively, or in addition, the methods can be used to isolate a population of activated T cells that are suitable for (or, upon expansion, are suitable for) use as an endogenous T cell therapeutic agent.

In another aspect, microfluidic devices suitable for sorting T lymphocytes are provided. The microfluidic devices can include a flow path having a first region that comprises a first array of posts, with the first region of the flow path having a first direction corresponding to the general direction of fluid flow through the first region. The first region can be a channel (e.g., a main channel), and the first array of posts can extend across the entire width of the channel. The first array can be characterized by a critical size (Dc) of about 4 microns to about 7 microns, or about 7 microns to about 10 microns. The posts of the first array can be arranged in rows and columns, with the rows of posts in the first array defining a first array direction that differs from the first direction of the first region by a tilt angle ($\varepsilon$). The columns of posts in the first array can repeat periodically with a periodicity equal to $1/\varepsilon$, where $\varepsilon$ is measured in radians. Adjacent posts in each respective column in the first array define gaps through which fluid can flow, generally transversely with respect to the columns. The columns of posts can be arranged substantially transversely with respect to the first direction of the first region (e.g., each column of posts can be arranged along an axis that is oriented about 80° to about 100° relative to the first direction of the first region) or, more generally, the columns of posts can be arranged along an axis that is oriented about 45° to about 135° relative to the first direction of the first region.

The flow path of the microfluidic devices can include a second region which receives fluid that passes through the first region, and the second region can include a divider that separates the second region into a first channel and a second channel. The first channel can receive a first portion of any fluid that passes through the first region, and the second channel can receive a second portion of any fluid that passes through the first region. Either the first channel or the second channel can include a second array of posts. The microfluidic device can further include one or more sequestration pens, each of which can have an opening that opens to either the first channel or the second channel.

In yet another aspect, compositions comprising T lymphocytes, particularly T lymphocytes that have been sorted/ enriched according to any one of the methods disclosed herein, are provided. As discussed above, such compositions can be suitable for use as an endogenous T cell therapeutic agent, or as a starting material for generating such a therapeutic agent.

Additional aspect, objects and advantages will be set forth in part in the description which follows, and in part will be obvious from the description, or may be learned by practice. The aspects, objects and advantages will be realized and attained by means of the elements and combinations particularly pointed out in the appended claims.

It is to be understood that both the foregoing summary and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIGS. 9A-9D depict cell count plots generated from FACS analysis of populations of T lymphocytes (including both activated and resting T lymphocytes) prior to and after sorting using a microfluidic device having an array of posts.

DETAILED DESCRIPTION OF EMBODIMENTS

Figure 1:
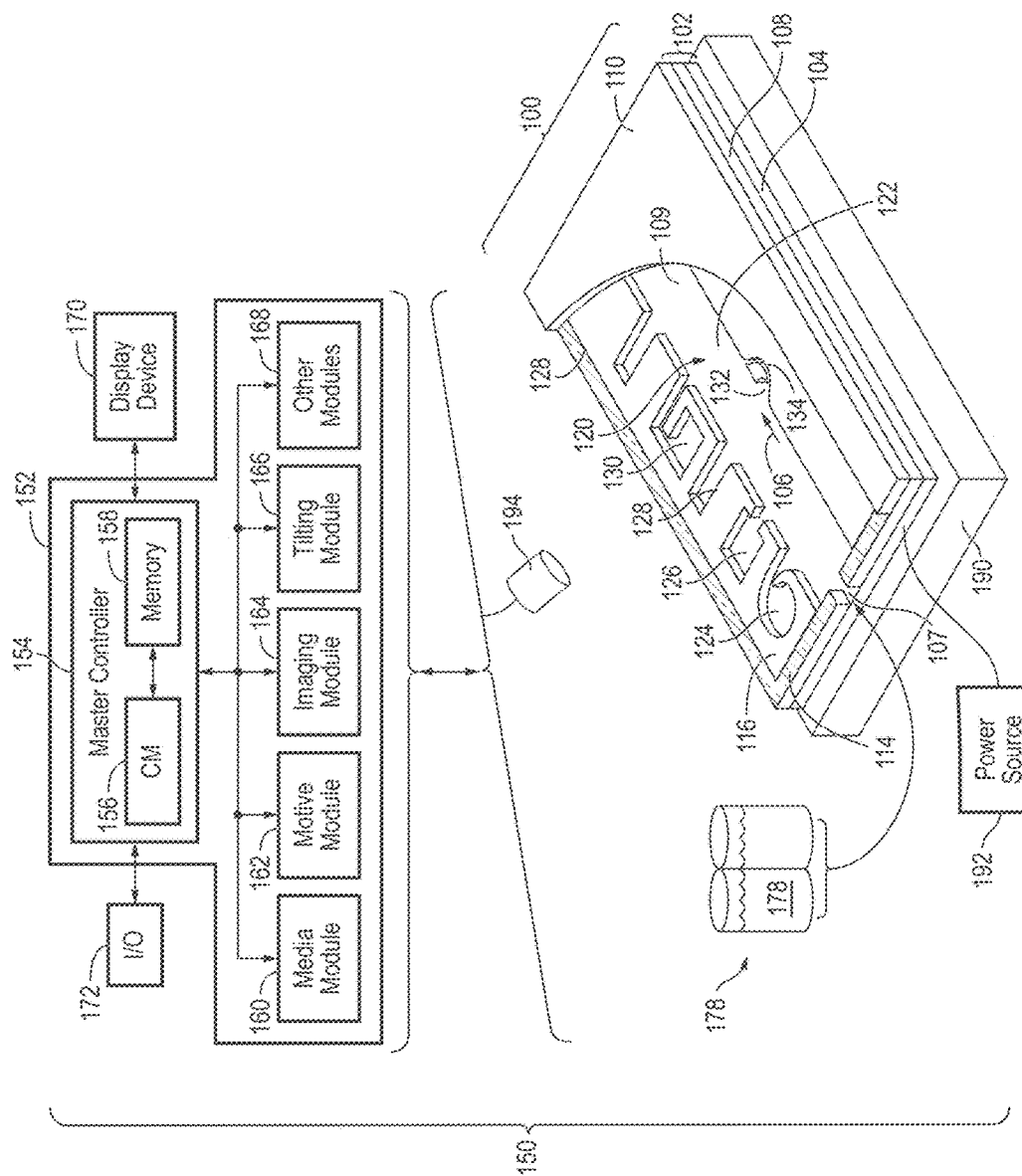
FIG. 1 illustrates an example of a system for operating and monitoring a microfluidic device according to certain embodiments.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "ones" means more than one. As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least two ports configured to allow the fluid (and, optionally, micro-objects suspended in the fluid) to flow into and/or out of the microfluidic device. Typically, a microfluidic circuit of a microfluidic device will include at least one microfluidic channel and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 μL.

As used herein, a "nanofluidic device" or "nanofluidic apparatus" is a type of microfluidic device having a microfluidic circuit that contains at least one circuit element configured to hold a volume of fluid of less than about 1 μL, e.g., less than about 750, 500, 250, 200, 150, 100, 75, 50, 25, 20, 15, 10, 9, 8, 7, 6, 5, 4, 3, 2, 1 nL or less. Typically, a nanofluidic device will comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements is configured to hold a volume of fluid of about 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "channel" as used herein refers to flow region of a microfluidic device having a length that is significantly longer than both the horizontal and vertical dimensions. The length of the channel is generally defined by the flow path of the channel. In the case of a straight channel, the length would be the "longitudinal axis" of the channel. The "horizontal dimension" or "width" of the channel is the horizontal dimension as observed in a transverse section oriented perpendicular to the longitudinal axis of the channel (or, if the channel is curved, perpendicular to an axis tangential to the flow path of the channel at the plane of the transverse section). The "vertical dimension" or "height" of the channel is the vertical dimension as observed in a transverse section oriented perpendicular to the longitudinal axis of the channel (or, if the channel is curved, perpendicular to an axis tangential to the flow path of the channel at the plane of the transverse section). The flow channel can be, for example, at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 100,000 microns to about 500,000 microns, including any range therebetween. In some embodiments, the horizontal dimension (or width) is in the range of from about 100 microns to about 1000 microns (e.g., about 150 to about 500 microns) and the vertical dimension (or height) is in the range of from about 25 microns to about 200 microns, e.g., from about 40 to about 150 microns. It must be noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, a microfluidic sequestration pen and a microfluidic channel, or a connection region and an isolation region of a microfluidic sequestration pen.

As used herein, the term "constriction" refers generally to a narrowing of a width of a circuit element (or an interface between two circuit elements) in a microfluidic device. The constriction can be located, for example, at the interface between a microfluidic sequestration pen and a microfluidic channel, or at the interface between an isolation region and a connection region of a microfluidic sequestration pen.

As used herein, the term "transparent" refers to a material which allows visible light to pass through without substantially altering the light as is passes through.

As used herein, the term "micro-object" refers generally to any microscopic object that may be isolated and collected in accordance with the present disclosure. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells (e.g., embryos, oocytes, sperm cells, cells dissociated from a tissue, eukaryotic cells, protist cells, animal cells, mammalian cells, human cells, immunological cells, hybridomas, cultured cells, cells from a cell line, cancer cells, infected cells, transfected and/or transformed cells, reporter cells, prokaryotic cell, and the like); biological organelles; vesicles, or complexes; synthetic vesicles; liposomes (e.g., synthetic or derived from membrane preparations); lipid nanorafts (as described in Ritchie et al. (2009) "Reconstitution of Membrane Proteins in Phospholipid Bilayer Nanodiscs," Methods Enzymol., 464:211-231), and the like; or a combination of inanimate micro-objects and biological micro-objects (e.g., microbeads attached to cells, liposome-coated micro-beads, liposome-coated magnetic beads, or the like). Beads may further have other moieties/molecules covalently or non-covalently attached, such as fluorescent labels, proteins, small molecule signaling moieties, antigens, or chemical/biological species capable of use in an assay.

As used herein, the terms "T lymphocyte" and "T cell" are used interchangeably.

As used herein, the term "maintaining (a) cell(s)" refers to providing an environment comprising both fluidic and gaseous components and, optionally a surface, that provides the conditions necessary to keep the cells viable and/or expanding.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Culturing, Selecting, and Expanding T Lymphocytes in Microfluidic/Nanofluidic Devices.

Methods of selecting and expanding biological cells, including T lymphocytes, within microfluidic devices have been described, for example, in U.S. patent application Ser. No. 15/135,707, filed on Apr. 22, 2016, the entire contents of which are incorporated herein by reference. Methods of activating and expanding T lymphocytes within a microfluidic device have been described in International Application No. PCT/US17/22846, filed Mar. 16, 2017, the entire contents of which is incorporated herein by reference.

Microfluidic Devices and Systems for Operating and Observing Such Devices.

FIG. 1 illustrates a generalized example of a microfluidic device 100 and a system 150 which can be used to operate and observe microfluidic devices. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1, suitable microfluidic devices can include a plurality (e.g., 2 or 3) of such microfluidic circuits. Regardless, the microfluidic device 100 can be configured to be a nanofluidic device. In the embodiment illustrated in FIG. 1, the microfluidic circuit 120 comprises a plurality of microfluidic sequestration pens 124, 126, 128, and 130, each having a single opening in fluidic communication with flow path 106. As discussed further below, the microfluidic sequestration pens comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1, the microfluidic circuit 120 is defined by an enclosure 102. Although the enclosure 102 can be physically structured in different configurations, in the example shown in FIG. 1 the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1 but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise a rigid material. The rigid material may be glass or a material with similar properties. In some embodiments, the support structure 104 can comprise a deformable material. The deformable material can be a polymer, such as PDMS. In some embodiments, the support structure 104 can comprise both rigid and deformable materials.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA. However, the support structure 104 need not contain any electrodes or semiconductor substrates.

The microfluidic circuit structure 108 can define circuit elements of the microfluidic circuit 120. Such circuit elements can comprise spaces or regions that can be fluidly interconnected when microfluidic circuit 120 is filled with fluid, such as flow channels or chambers, either of which can include an array of posts (e.g., formed by the microfluidic circuit structure 108), pens, traps, and the like. In the microfluidic circuit 120 illustrated in FIG. 1, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements (including arrays of posts, not shown) and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1 or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

Figure 6:
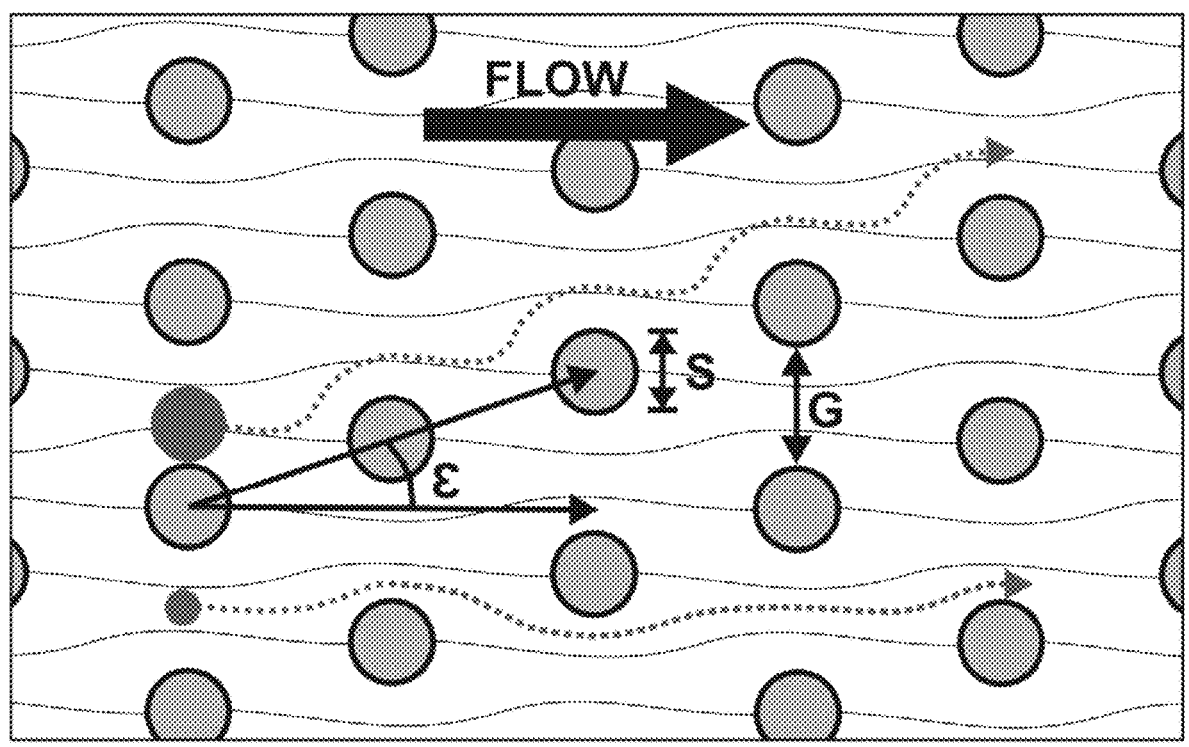
FIG. 6 is a schematic diagram of an array of posts which can be included in a microfluidic device according to certain embodiments.

The flow path of the microfluidic device can include a first region comprising an array of posts. The first region is bounded by a pair of walls (e.g., a first lateral wall and a second lateral wall) which together define a first direction corresponding to the expected directed of fluid flow in the first region of the flow path. The posts in the post array can be arranged in rows and columns, as generally shown in FIG. 6. The rows of posts can define a first array direction that differs from the first direction of the first region by a tilt angle ($\varepsilon$), with the columns of posts in the first array repeated periodically with a periodicity equal to $1/\varepsilon$, where $\varepsilon$ is measured in radians. Adjacent posts in each respective column in the first array define gaps through which fluid can flow generally transversely with respect to the columns. In general, the gaps between adjacent posts in the columns of a post array will have a characteristic size. As used herein in reference to the gaps between adjacent posts in the columns of a post array, the term "characteristic size" refers to a size that is the same (+/−5%) for the majority of gaps in the post array. In other words, at least 50% of the gaps between adjacent posts in the columns of the post array can have the characteristic size. More typically, at least 60%, 70%, 80%, 90%, 95%, or more of the gaps between adjacent posts in the columns of the post array can have the characteristic size.

The posts of the array can more generally be termed obstacles. Obstacle/post arrays have been described, e.g., in U.S. Pat. Nos. 7,150,812 and 8,783,467, the contents of which are incorporated by reference herein in their entirety.

Figure 7A:
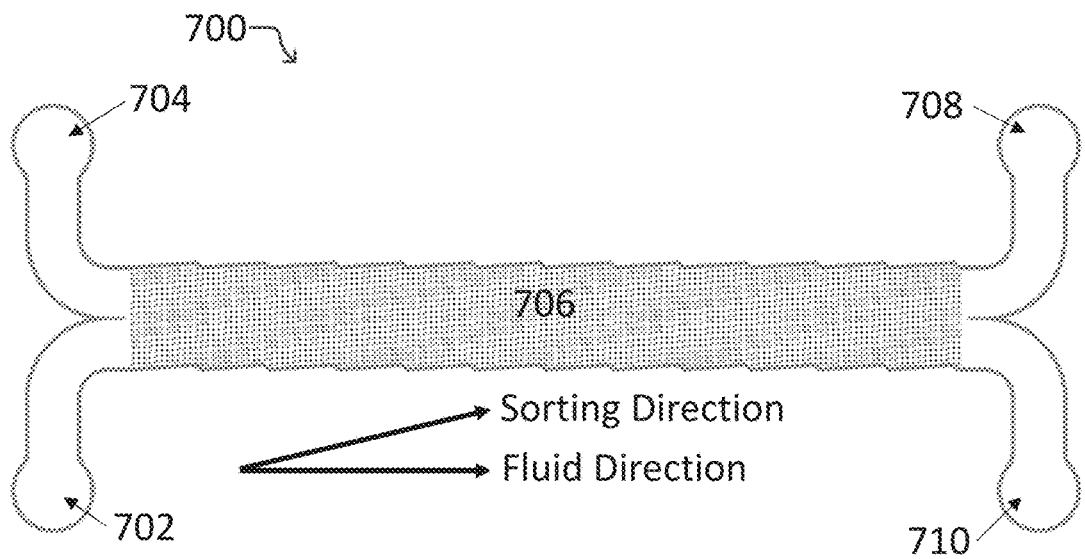
FIGS. 7A and 7B illustrate microfluidic devices having arrays of posts according to certain embodiments.
Figure 7B:
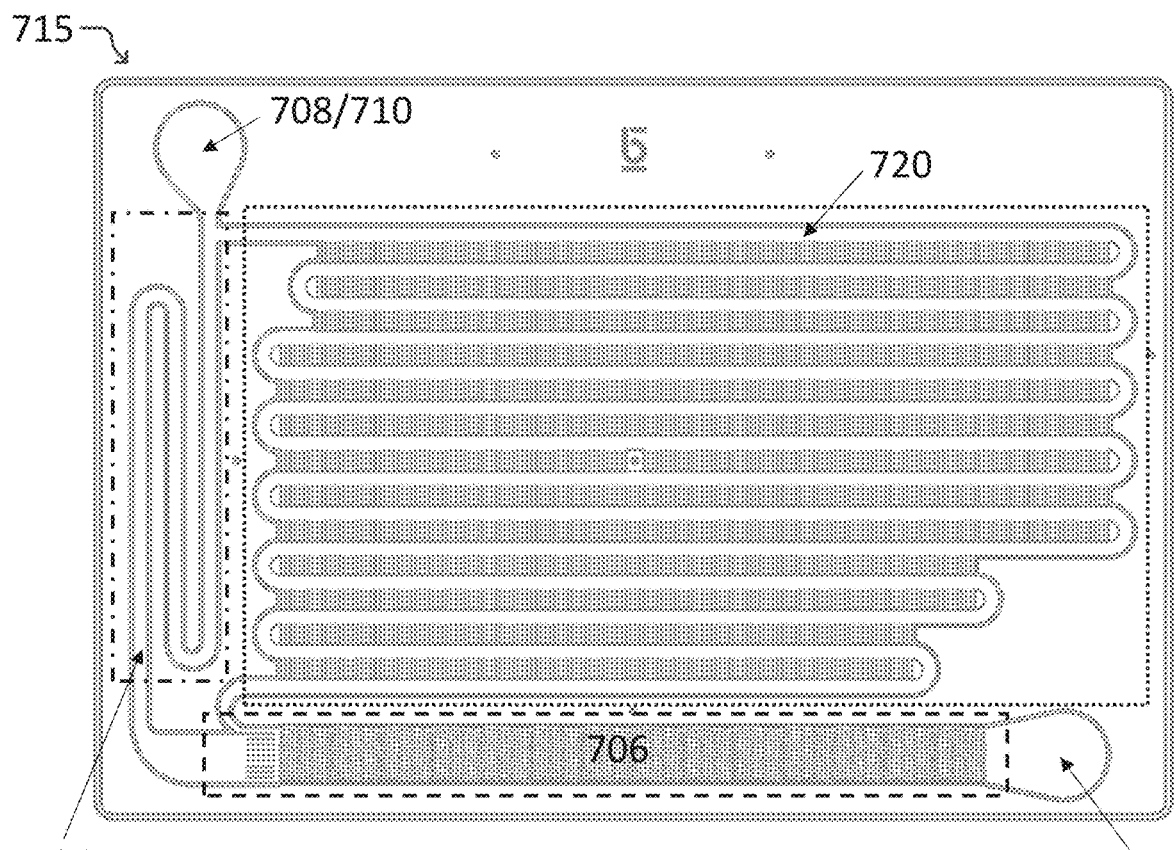

The post array will generally extend across the entire width of the first region of the flow path. The microfluidic device can have one or more ports that function as inlets and one or more ports that function as outlets. For example, as shown in FIG. 7B, a port upstream of the first region 706 can function as an inlet 702, while a port downstream of the first region 706 can function as an outlet 708/710. Alternatively, as illustrated in FIG. 7A, a pair of ports located upstream of the first region can function as inlets 702 and 704 to the microfluidic device (e.g., a first upstream port 702 can provide a flow of a fluid sample comprising cells, such as T lymphocytes, while a second upstream port 704 can provide a flow of medium or buffer that lacks cells). Similarly, a pair of ports 708 and 710 located downstream can allow fluid flows to exit the microfluidic device. For example, a first downstream port 708 can provide an outlet for fluid that is enriched for a desired population of cells, particularly activated T lymphocytes, and a second downstream port 710 can provide an outlet for waste. In some embodiments, the waste stream can come from a bypass channel.

The array of posts can be generally characterized by a critical size ($D_c$), which can be about 3 microns to about 15 microns (e.g., about 4 microns to about 10 microns, or about 7 microns to about 12 microns). In some embodiments, the array is characterized by a Dc of about 4 microns to about 7 microns (e.g., about 4 microns to about 5 microns, about 4.5 microns to about 5.5 microns, about 5 microns to about 6 microns, about 5.5 microns to about 6.5 microns, about 6 microns to about 7 microns, or any range defined by the foregoing endpoints). In other embodiments, the array is characterized by a $D_c$ of about 7 microns to about 10 microns (e.g., about 7 microns to about 8 microns, about 7.5 microns to about 8.5 microns, about 8 microns to about 9 microns, about 8.5 microns to about 9.5 microns, about 9 microns to about 10 microns, or any range defined by the foregoing endpoints. Importantly, the $D_c$ can be selected such that naïve T lymphocytes, which will typically have a diameter less than activated T lymphocytes, will predominantly flow through the post array in the general direction of fluid flow, while activated T lymphocytes will travel in the first array direction defined by the rows of the array. In this manner, fluid flowing through the post array can become enriched for activated T lymphocytes. As used herein, "enriched" means that the proportion of cells of interest in a portion of fluid is increased as a result of moving through the post array, as compared to the proportion of such cells of interest in the portion of fluid prior to the fluid moving through the post array. The amount of enrichment can be calculated in different ways. For example, one simple measurement is to divide the percentage of activated T lymphocytes in the fluid portion after it has moved through the post array by the percentage of activated T lymphocytes in the fluid portion just before it entered the post array. Alternatively, enrichment can be calculated as $(N^+_{out}/N^-_{out})/(N^+_{in}/N^-_{in})$, where $N^+_{out}$ is the number of cells of interest detected in the fluid portion after it has moved through the post array, $N^-_{out}$ is the number of cells other than the cells of interest detected in the fluid portion after it has moved through the post array, $N^+_{in}$ is the number of cells of interest detected in the fluid portion just before it moves through the post array, and $N^-_{in}$ is the number of cells other than the cells of interest detected in the fluid portion just before it moves through the post array. The exact calculation of enrichment is not critical. For example, either of the foregoing definitions can be used and, provided that at least one calculation indicates an enrichment, then the fluid portion that has moved through the post array would be considered enriched.

In certain embodiments, the array has a tilt angle ε of about 1/3 radians to about 1/100 radians (e.g., about 1/5 radians to about 1/20 radians, or about 1/10 radians to about 1/16 radians).

The gaps between adjacent posts in each column of the first array can be about 15 microns to about 100 microns (e.g., about 20 microns to about 30 microns, about 25 microns to about 35 microns, about 30 microns to about 40 microns, about 35 microns to about 45 microns, about 40 microns to about 50 microns, about 45 microns to about 55 microns, about 50 microns to about 60 microns, about 55 microns to about 65 microns, about 60 microns to about 70 microns, about 65 microns to about 75 microns, about 70 microns to about 90 microns, about 80 microns to about 100 microns, or any range defined by the foregoing endpoints). In certain particular embodiments, the gaps can be about 15 microns to about 30 microns, about 20 microns to about 35 microns, or about 25 microns to about 40 microns.

In general, the size of the gaps between adjacent posts in the same column of the first array are substantially equal, having a size equivalent to a characteristic size. However, exceptions are permitted. In particular, the size of the gaps between adjacent posts (in the same column) most proximal to a lateral wall bounding the region that contains the post array may deviate from the characteristic size. As persons skilled in the art will understand, such deviations in gap sizes can be designed to reduce boundary irregularities in the flow of fluids through the array caused by the spacing between the lateral walls and the post immediately adjacent to such walls.

In certain embodiments, the posts of the array have a circular shape in cross-section. Alternatively, the posts of the first array have a polyhedral shape, such as a triangular shape, a square shape, a rhomboid shape, a parallelogram shape, a pentagon shape, a hexagon shape, or the like, or even an irregular shape when viewed in cross-section. Typically, the posts in the array will all have the same orientation (when viewed in cross-section relative to the first direction of the array. In certain embodiments, the polyhedral/irregularly shaped posts are oriented asymmetrically with regard to the axis defined by the first direction. In this manner, the posts can be oriented such that no axis of symmetry in the cross-sectional shape of the posts is parallel to the axis defined by the first direction of the array.

Posts of the first array can have a diameter of about 30 microns to about 100 microns (e.g., about 30 microns to about 50 microns, about 30 microns to about 60 microns, about 30 microns to about 70 microns, about 40 microns to about 60 microns, about 40 microns to about 70 microns, about 40 microns to about 80 microns, about 40 microns to about 90 microns, about 50 microns to about 70 microns, about 50 microns to about 80 microns, about 50 microns to about 90 microns, about 50 microns to about 100 microns, about 60 to about 80 microns, about 60 microns to about 90 microns, about 60 microns to about 100 microns, about 70 microns to about 90 microns, about 70 microns to about 100 microns, about 80 microns to about 100 microns, or any range defined by the foregoing endpoints). For polyhedral or irregularly shaped posts, the "diameter" of the post is the largest cross-sectional width as measured along an axis perpendicular to the direction of fluid flow (i.e., the first direction).

Table 1 provides a number of designs for exemplary post arrays and their corresponding critical size $D_c$, any of which can be used in the disclosed methods depending upon the size separation desired.

TABLE 1

Exemplary Post Array Designs

| Post Shape | Post Size | Gap Size | Array Tilt | Critical Diameter |
|---|---|---|---|---|
| Triangle | 50 | 30 | 1/12 | 7.2 |
| Circular | 50 | 30 | 1/15 | 8.8 |
| Triangle | 50 | 15 | 1/16 | 3 |
| Triangle | 50 | 20 | 1/16 | 4 |
| Triangle | 50 | 20 | 1/12 | 5 |
| Triangle | 50 | 25 | 1/12 | 6 |
| Triangle | 50 | 25 | 1/10 | 7 |
| Triangle | 50 | 29 | 1/10 | 8 |
| Triangle | 50 | 33 | 1/10 | 9 |
| Triangle | 50 | 37 | 1/10 | 10 |
| Triangle | 50 | 15 | 1/16 | 3 |
| Triangle | 50 | 25 | 1/12 | 6 |
| Diamond | 70 | 21 | 1/12 | 6 |
| Diamond | 70 | 17.5 | 1/12 | 5 |
| Diamond | 70 | 21 | 1/10 | 7 |

The posts of the first array can be formed from any of a wide variety of materials, including any of the materials described herein for the construction of a microfluidic device, such as microfluidic circuit material 116. Thus, for example, the posts can be made from a silicone polymer (e.g., PDMS, PPS, or the like).

Microfluidic devices having a post array as described above will typically have a flow path that includes a first region having the post array and a second region configured to receive a flow of fluid after the fluid has passed through the first region. The first region can have a length of about 5 mm to about 15 mm (e.g., about 5 mm to about 10 mm, about 6 mm to about 11 mm, about 7 mm to about 12 mm, about 8 mm to about 13 mm, about 9 mm to about 14 mm, about 10 mm to about 15 mm, or any range defined by the foregoing endpoints), with the length being measured along an axis defined by the first direction. The second region can be split by a divider (or wall) that separates the second region, for example, into a first channel and a second channel. Other arrangements are also possible, such as multiple dividers (or walls), as will be evident by the discussion below. The second region can be configured relative to the first region such that particles/cells (e.g., T lymphocytes) having a diameter less than the characteristic Dc of the post array predominantly flow into a first channel and particles/cells (e.g., T lymphocytes) having a diameter greater than the characteristic Dc of the array predominantly flow into a second channel. As used herein, the "diameter" of a particle/cell, such as a T lymphocyte, is the effective size of the particle/cell as it travels through the post array. This effective diameter can be influenced by a variety of factors, including the health of the cell, the stage of the cell cycle, the composition of the posts in the array, coatings on the posts of the array, and the like. In certain embodiments, the first channel can be a "bypass channel" that goes directly to export/waste, and the second channel can be a selection and/or assay channel into which the most desired particles/cells (e.g., T lymphocytes) are directed.

In some embodiments, the first channel is configured to receive at least 50% (e.g., at least 60%, 70%, 75%, 80%, 85%, 90%, or more) of the fluid flowing out of the first region (and the post array). In some embodiments, the first channel is configured to receive about 85% to about 95% (e.g., about 87%, to about 93%, about 88% to about 92%, about 89% to about 91%, about 90%, or any range defined by the foregoing endpoints) of the fluid flowing out of the first region (and the post array). In such embodiments, the remaining fluid flowing into the second channel (which can be, for example, 50%, 45%, 40%, 35%, 30%, 25%, 20%, 15%, 10%, 5%, or less of the fluid flowing out of the first region) can include all or most of the particles/cells having an effective diameter greater than the Dc of the post array. Thus, for example, as T lymphocytes having a diameter greater than Dc exit the first region and enter the second channel of the second region, they can be effectively concentrated by a factor of at least about 2, about 2.5, about 3, about 3.5, about 4, about 4.5, about 5, about 6, about 7, about 8, about 9, about 10, about 15, about 20, or greater.

In certain embodiments, the flow path of the microfluidic device can include a second region that splits into a first channel and a second channel, with the first and second being configured such that a pressure differential across the first channel is equal to a pressure differential across the second channel. This equal pressure can be achieved, for example, if the channels rejoin (e.g., before reaching an outlet port) or if they lead to separate outlet ports. To ensure that there is substantially equal pressure in each channel, the resistance in the channels can be matched according to the formula $\Delta P = Q_{CH1} * R_{CH1} = Q_{CH2} * R_{CH2}$, where $Q_{CH1}$ is the volumetric flow in the first channel per unit time, $Q_{CH2}$ is the volumetric flow in the second channel per unit time, and $R_{CH1}$ and $R_{CH2}$ are the respective fluidic resistances in the first and second channels. For a channel having a rectangular shape in cross-section, $R = L/(W*d^3)$, where L is the length of the channel, W is one cross-sectional dimension of the channel, and d is the smallest cross-sectional dimension of the channel.

In certain embodiments, the first channel comprises a length and the second channel comprises a length, and the length of the second channel is larger than the length of the first channel (e.g., at least 6, 7, 8, 9, 10, 11, 12, 15, or 20 times larger). The microfluidic device can include at least one sequestration pen, as described herein, that opens off of the second channel of the second region and has a volume large enough to hold at least one T lymphocyte. The sequestration pen can have a volume of about 250 pL to about 3 nL (e.g., about 250 pL to about 1 nL, about 375 pL to about 1 nL, about 500 pL to about 1 nL, about 750 pL to about 1 nL, about 250 pL to about 1.25 nL, about 500 pL to about 1.25 nL, about 750 pL to about 1.25 nL, about 1 nL to about 1.25 nL, about 500 pL to about 1.5 nL, about 750 pL to about 1.5 nL, about 1 nL to about 1.5 nL, about 500 pL to about 2 nL, about 750 pL to about 2 nL, about 1 nL to about 2 nL, about 1.25 nL to about 2 nL, about 1.5 nL to about 2 nL, about 1 nL to about 2.5 nL, about 1.5 nL to about 2.5 nL, about 2 nL to about 2.5 nL, about 1 nL to about 3 nL, about 1.5 nL to about 3 nL, about 2 nL to about 3 nL, or about 2.5 nL to about 3 nL).

The microfluidic devices can include more than one post array. For example, the second channel can include a first sub-region comprising a second array of posts. The second channel can be configured such that a portion of fluid flowing through the first region of the flow path will enter into the second channel, and that portion of fluid and any cells contained therein will pass through the second array.

The second array can be similar to the first array. For example, having the same critical size $D_c$ (or a similar critical size, e.g., +/−0.5 microns) can facilitate removal of unwanted cells/micro-objects and further enrichment of the sample. In some embodiments, the second array can have a different critical size ($D_c$). For example, the first array can have a critical size of about 4 microns to about 7 microns (e.g., about 6 microns), and the second array can have a critical size of about 7 microns to about 10 microns (e.g., about 9 microns). The larger critical size of the second array can remove micro-objects that are larger than desired, such as unwanted cells that are about to dividing.

In some embodiments, the second channel can include a first subregion that includes that second post array and a second subregion. The second subregion can be configured to receive a flow of fluid after it passes through the first subregion (and the second post array). The second subregion can, for example, include a divider, such as a wall, that separates the second channel into a third channel and a fourth channel. In this manner, by passing the sample through a series of post arrays, the cells (T lymphocytes) in the sample can be more finely sorted. In addition, sequestration pens can be positioned such that they open off of either the third channel or the fourth channel, allowing the flow of liquid to be stopped and cells of interest to be penned and, optionally, cultured on chip.

Exemplary designs for microfluidic chips having a post array are shown in FIGS. 7A and 7B (i.e., microfluidic devices 700 and 715), and described in connection with the examples.

FIG. 1 also shows a system 150 for operating and controlling microfluidic devices, such as microfluidic device 100. System 150, as illustrated, includes an electrical power source 192, an imaging device 194, and a tilting device 190.

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 4, the imaging device 194 may further include a microscope (or an optical train), which may or may not include an eyepiece.

System 150 can further comprise a tilting device 190 configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1. Alternatively, the media source 178 can be located in whole or in part inside the enclosure 102 of the microfluidic device 100. For example, the media source 178 can comprise reservoirs that are part of the microfluidic device 100.

FIG. 1 also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 2A and 2B, the enclosure 102 can comprise a dielectrophoresis (DEP), optoelectronic tweezers (OET) and/or opto-electrowetting (OEW) configuration (not shown in FIG. 1), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. In some instances, pens 124, 126, 128, 130 are configured to physically corral one or more micro-objects within the microfluidic circuit 120. Sequestration pens in accordance with the present disclosure can comprise various shapes, surfaces and features that are optimized for use with DEP, OET, OEW, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. Sequestration pens in accordance with the present disclosure are useful for culturing, selecting, and expanding T cells. As shown, microfluidic sequestration pens 124, 126, 128, and 130 of microfluidic circuit 120 each comprise differing features and shapes which may provide one or more benefits useful in culturing, selecting, and expanding T cells. In some embodiments, the microfluidic circuit 120 comprises a plurality of identical microfluidic sequestration pens. In some embodiments, the microfluidic circuit 120 comprises a plurality of microfluidic sequestration pens, wherein two or more of the sequestration pens comprise differing structures and/or features which provide differing benefits in culturing, selecting, and expanding T cells.

In the embodiment illustrated in FIG. 1, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens are configured (e.g., relative to a channel 122) such that they can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the teachings of the present disclosure. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the teachings of the present disclosure.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 2A:
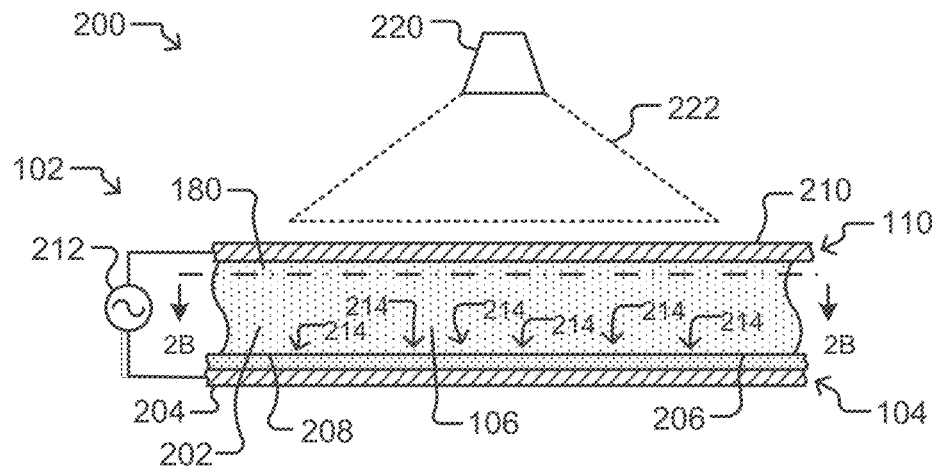
FIGS. 2A and 2B illustrate a microfluidic device according to certain embodiments.

FIGS. 2A-2F illustrates various embodiments of microfluidic devices that can be used in the practice of the present disclosure. FIG. 2A depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an opto-electrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Motive Microfluidic Device Configurations.

As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 2B:
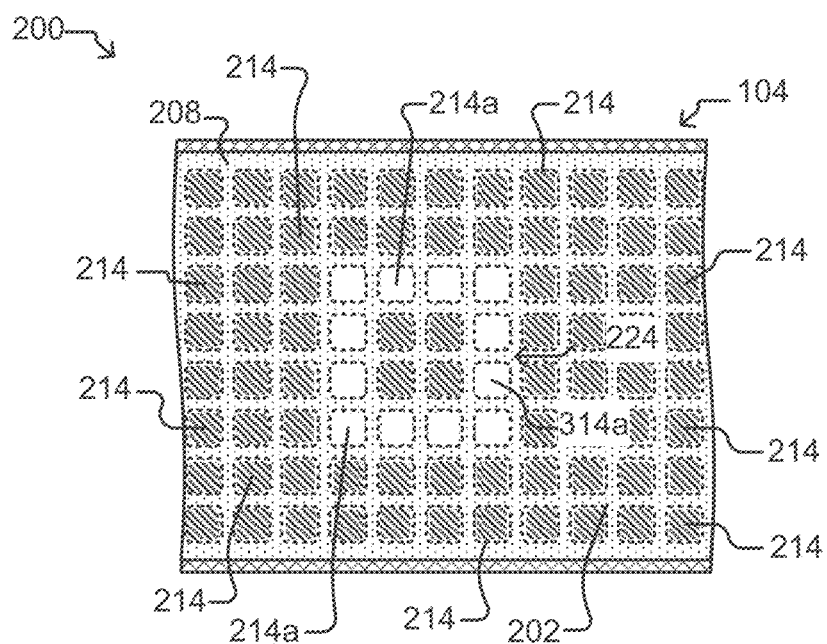

One example of a microfluidic device 200 comprising a DEP configuration is illustrated in FIGS. 2A and 2B. While for purposes of simplicity FIGS. 2A and 2B show a side cross-sectional view and a top cross-sectional view, respectively, of a portion of an enclosure 102 of the microfluidic device 200 having an open region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 2A, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 2A and 2B can have an optically-actuated DEP configuration. Accordingly, changing patterns of light 222 from the light source 220, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 2B, a light pattern directed onto the inner surface 208 of the electrode activation substrate 206 can illuminate select DEP electrode regions 214a (shown in white) in a pattern, such as a square light pattern 224. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 222 projected from a light source 220 into the microfluidic device 200. Whether the DEP forces attract or repel nearby micro-objects can depend on such parameters as the frequency of the power source 212 and the dielectric properties of the medium 180 and/or micro-objects (not shown).

The square pattern 224 of illuminated DEP electrode regions 214a illustrated in FIG. 2B is an example only. Any pattern of the DEP electrode regions 214 can be illuminated (and thereby activated) by the pattern of light 222 projected into the device 200, and the pattern of illuminated/activated DEP electrode regions 214 can be repeatedly changed by changing or moving the light pattern 222.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. In such embodiments, the DEP electrode regions 214 can be created anywhere and in any pattern on the inner surface 208 of the electrode activation substrate 208, in accordance with the light pattern 222. The number and pattern of the DEP electrode regions 214 thus need not be fixed, but can correspond to the light pattern 222. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 222. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 222, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 222.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 220 can alternatively be used to illuminate the enclosure 102 from below.

With the microfluidic device 200 of FIGS. 2A-2B having a DEP configuration, the motive module 162 can select a micro-object (not shown) in the medium 180 in the region/chamber 202 by projecting a light pattern 222 into the device 200 to activate a first set of one or more DEP electrodes at DEP electrode regions 214a of the inner surface 208 of the electrode activation substrate 206 in a pattern (e.g., square pattern 224) that surrounds and captures the micro-object. The motive module 162 can then move the captured micro-object by moving the light pattern 222 relative to the device 200 to activate a second set of one or more DEP electrodes at DEP electrode regions 214. Alternatively, the device 200 can be moved relative to the light pattern 222.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 224), one or more micro-objects in region/chamber 202 can be trapped and moved within the region/chamber 202. The motive module 162 in FIG. 1 can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or halfnuim oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 nm to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 microns. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 222 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 222 (or moving microfluidic device 200 relative to the light source 220) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1 can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Sequestration Pens.

Figure 2C:
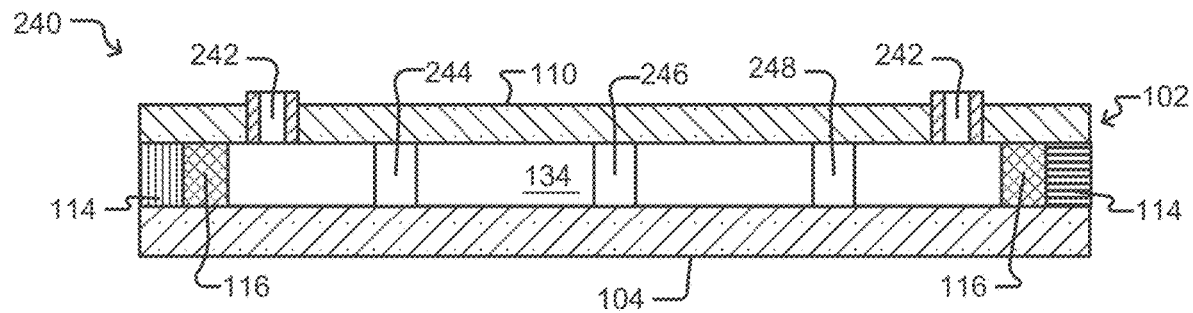
FIGS. 2C and 2D illustrate sequestration pens according to certain embodiments.
Figure 2D:
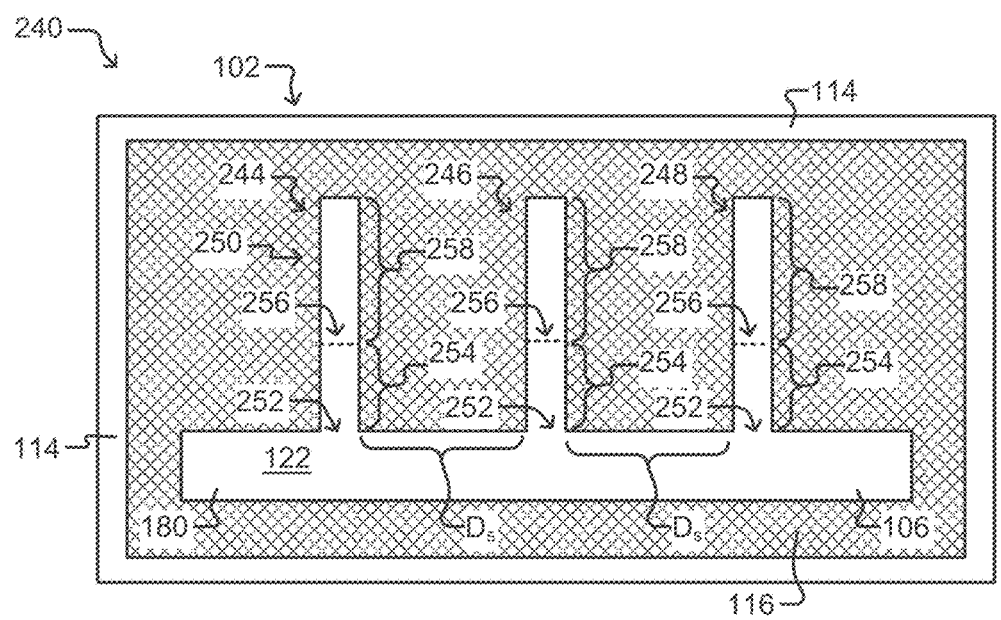

Non-limiting examples of generic sequestration pens 244, 246, and 248 are shown within the microfluidic device 240 depicted in FIGS. 2C-2D. Each sequestration pen 244, 246, and 248 can comprise an isolation structure 250 defining an isolation region 258 and a connection region 254 fluidically connecting the isolation region 258 to a channel 122. The connection region 254 can comprise a proximal opening 252 to the channel 122 and a distal opening 256 to the isolation region 258. The connection region 254 can be configured so that the maximum penetration depth of a flow of a fluidic medium (not shown) flowing from the channel 122 into the sequestration pen 244, 246, 248 does not extend into the isolation region 258. Thus, due to the connection region 254, a micro-object (not shown) or other material (not shown) disposed in an isolation region 258 of a sequestration pen 244, 246, 248 can thus be isolated from, and not substantially affected by, a flow of medium 180 in the channel 122.

The channel 122 can thus be an example of a swept region, and the isolation regions 258 of the sequestration pens 244, 246, 248 can be examples of unswept regions. As noted, the channel 122 and sequestration pens 244, 246, 248 can be configured to contain one or more fluidic media 180. In the example shown in FIGS. 2C-2D, the ports 242 are connected to the channel 122 and allow a fluidic medium 180 to be introduced into or removed from the microfluidic device 240. Prior to introduction of the fluidic medium 180, the microfluidic device may be primed with a gas such as carbon dioxide gas. Once the microfluidic device 240 contains the fluidic medium 180, the flow 260 of fluidic medium 180 in the channel 122 can be selectively generated and stopped. For example, as shown, the ports 242 can be disposed at different locations (e.g., opposite ends) of the channel 122, and a flow 260 of medium can be created from one port 242 functioning as an inlet to another port 242 functioning as an outlet.

Figure 2E:
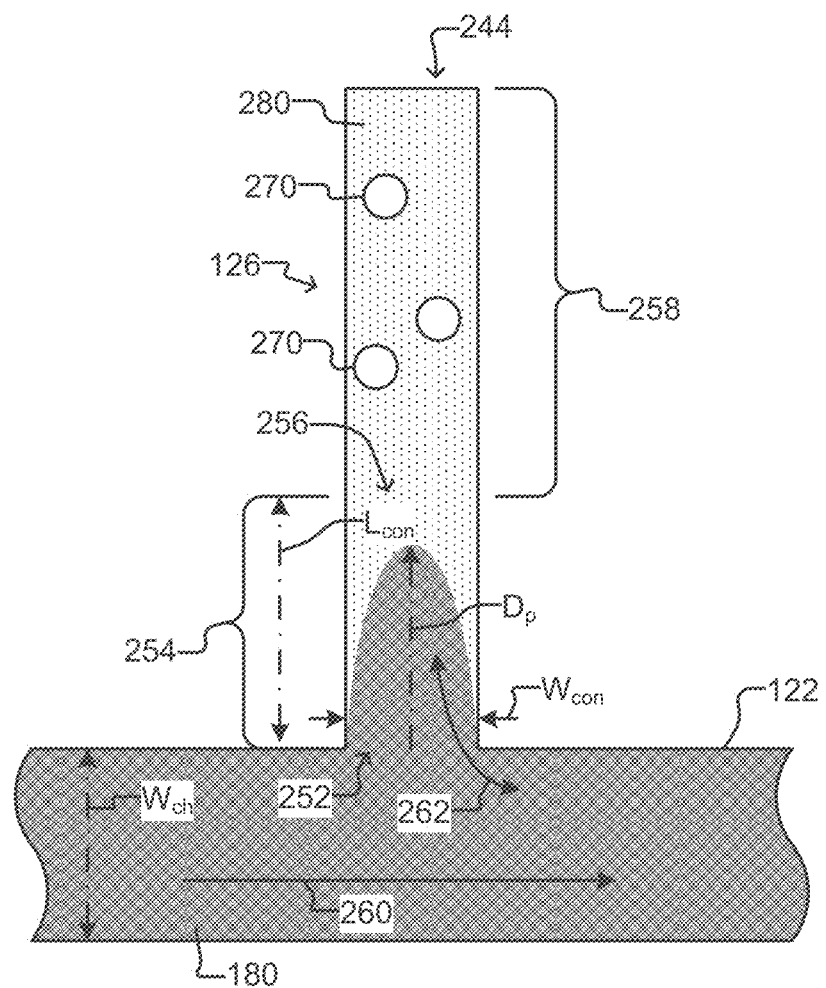
FIG. 2E illustrates a detailed sequestration pen according to certain embodiments.

FIG. 2E illustrates a detailed view of an example of a sequestration pen 244 according to the present disclosure. Examples of micro-objects 270 are also shown.

As is known, a flow 260 of fluidic medium 180 in a microfluidic channel 122 past a proximal opening 252 of a sequestration pen 244 can cause a secondary flow 262 of the medium 180 into and/or out of the sequestration pen 244. To isolate micro-objects 270 in the isolation region 258 of a sequestration pen 244 from the secondary flow 262, the length $L_{con}$ of the connection region 254 of the sequestration pen 244 (i.e., from the proximal opening 252 to the distal opening 256) should be greater than the penetration depth $D_p$ of the secondary flow 262 into the connection region 254. The penetration depth $D_p$ of the secondary flow 262 depends upon the velocity of the fluidic medium 180 flowing in the channel 122 and various parameters relating to the configuration of the channel 122 and the proximal opening 252 of the connection region 254 to the channel 122. For a given microfluidic device, the configurations of the channel 122 and the opening 252 will be fixed, whereas the rate of flow 260 of fluidic medium 180 in the channel 122 will be variable. Accordingly, for each sequestration pen 244, a maximal velocity Vmax for the flow 260 of fluidic medium 180 in channel 122 can be identified that ensures that the penetration depth $D_p$ of the secondary flow 262 does not exceed the length $L_{con}$ of the connection region 254. As long as the rate of the flow 260 of fluidic medium 180 in the channel 122 does not exceed the maximum velocity Vmax, the resulting secondary flow 262 can be limited to the channel 122 and the connection region 254 and kept out of the isolation region 258. The flow 260 of medium 180 in the channel 122 will thus not draw micro-objects 270 out of the isolation region 258. Rather, micro-objects 270 located in the isolation region 258 will stay in the isolation region 258 regardless of the flow 260 of fluidic medium 180 in the channel 122.

Moreover, as long as the rate of flow 260 of medium 180 in the channel 122 does not exceed $V_{max}$, the flow 260 of fluidic medium 180 in the channel 122 will not move miscellaneous particles (e.g., microparticles and/or nanoparticles) from the channel 122 into the isolation region 258 of a sequestration pen 244. Having the length $L_{con}$ of the connection region 254 be greater than the maximum penetration depth $D_p$ of the secondary flow 262 can thus prevent contamination of one sequestration pen 244 with miscellaneous particles from the channel 122 or another sequestration pen (e.g., sequestration pens 246, 248 in FIG. 2D).

Because the channel 122 and the connection regions 254 of the sequestration pens 244, 246, 248 can be affected by the flow 260 of medium 180 in the channel 122, the channel 122 and connection regions 254 can be deemed swept (or flow) regions of the microfluidic device 240. The isolation regions 258 of the sequestration pens 244, 246, 248, on the other hand, can be deemed unswept (or non-flow) regions. For example, components (not shown) in a first fluidic medium 180 in the channel 122 can mix with a second fluidic medium 280 in the isolation region 258 substantially only by diffusion of components of the first medium 180 from the channel 122 through the connection region 254 and into the second fluidic medium 280 in the isolation region 258. Similarly, components (not shown) of the second medium 280 in the isolation region 258 can mix with the first medium 180 in the channel 122 substantially only by diffusion of components of the second medium 280 from the isolation region 258 through the connection region 254 and into the first medium 180 in the channel 122. The first medium 180 can be the same medium or a different medium than the second medium 280. Moreover, the first medium 180 and the second medium 280 can start out being the same, then become different (e.g., through conditioning of the second medium 280 by one or more cells in the isolation region 258, or by changing the medium 180 flowing through the channel 122).

The maximum penetration depth $D_p$ of the secondary flow 262 caused by the flow 260 of fluidic medium 180 in the channel 122 can depend on a number of parameters, as mentioned above. Examples of such parameters include: the shape of the channel 122 (e.g., the channel can direct medium into the connection region 254, divert medium away from the connection region 254, or direct medium in a direction substantially perpendicular to the proximal opening 252 of the connection region 254 to the channel 122); a width $W_{ch}$ (or cross-sectional area) of the channel 122 at the proximal opening 252; and a width $W_{con}$ (or cross-sectional area) of the connection region 254 at the proximal opening 252; the velocity V of the flow 260 of fluidic medium 180 in the channel 122; the viscosity of the first medium 180 and/or the second medium 280, or the like.

In some embodiments, the dimensions of the channel 122 and sequestration pens 244, 246, 248 can be oriented as follows with respect to the vector of the flow 260 of fluidic medium 180 in the channel 122: the channel width $W_{ch}$ (or cross-sectional area of the channel 122) can be substantially perpendicular to the flow 260 of medium 180; the width $W_{con}$ (or cross-sectional area) of the connection region 254 at opening 252 can be substantially parallel to the flow 260 of medium 180 in the channel 122; and/or the length $L_{con}$ of the connection region can be substantially perpendicular to the flow 260 of medium 180 in the channel 122. The foregoing are examples only, and the relative position of the channel 122 and sequestration pens 244, 246, 248 can be in other orientations with respect to each other.

As illustrated in FIG. 2E, the width $W_{con}$ of the connection region 254 can be uniform from the proximal opening 252 to the distal opening 256. The width $W_{con}$ of the connection region 254 at the distal opening 256 can thus be in any of the ranges identified herein for the width $W_{con}$ of the connection region 254 at the proximal opening 252. Alternatively, the width $W_{con}$ of the connection region 254 at the distal opening 256 can be larger than the width $W_{con}$ of the connection region 254 at the proximal opening 252.

As illustrated in FIG. 2E, the width of the isolation region 258 at the distal opening 256 can be substantially the same as the width $W_{con}$ of the connection region 254 at the proximal opening 252. The width of the isolation region 258 at the distal opening 256 can thus be in any of the ranges identified herein for the width $W_{con}$ of the connection region 254 at the proximal opening 252. Alternatively, the width of the isolation region 258 at the distal opening 256 can be larger or smaller than the width $W_{con}$ of the connection region 254 at the proximal opening 252. Moreover, the distal opening 256 may be smaller than the proximal opening 252 and the width $W_{con}$ of the connection region 254 may be narrowed between the proximal opening 252 and distal opening 256. For example, the connection region 254 may be narrowed between the proximal opening and the distal opening, using a variety of different geometries (e.g. chamfering the connection region, beveling the connection region). Further, any part or subpart of the connection region 254 may be narrowed (e.g. a portion of the connection region adjacent to the proximal opening 252).

In various embodiments of sequestration pens (e.g. 124, 126, 128, 130, 244, 246 or 248), the isolation region (e.g. 258) is configured to contain a plurality of micro-objects. In other embodiments, the isolation region can be configured to contain only one, two, three, four, five, or a similar relatively small number of micro-objects. Accordingly, the volume of an isolation region can be, for example, at least $3 \times 10^3$, $6 \times 10^3$, $9 \times 10^3$, $1 \times 10^4$, $2 \times 10^4$, $4 \times 10^4$, $8 \times 10^4$, $1 \times 10^5$, $2 \times 10^5$, $4 \times 10^5$, $8 \times 10^5$, $1 \times 10^6$, $2 \times 10^6$, $4 \times 10^6$, $6 \times 10^6$ cubic microns, or more.

In various embodiments of sequestration pens, the width $W_{ch}$ of the channel 122 at a proximal opening (e.g. 252) can be within any of the following ranges: 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. The foregoing are examples only, and the width Web of the channel 122 can be in other ranges (e.g., a range defined by any of the endpoints listed above). Moreover, the $W_{ch}$ of the channel 122 can be selected to be in any of these ranges in regions of the channel other than at a proximal opening of a sequestration pen.

In some embodiments, a sequestration pen has a cross-sectional height of about 30 to about 200 microns, or about 50 to about 150 microns. In some embodiments, the sequestration pen has a cross-sectional area of about 100,000 to about 2,500,000 square microns, or about 200,000 to about 2,000,000 square microns. In some embodiments, a connection region has a cross-sectional height that matches the cross-sectional height of the corresponding sequestration pen. In some embodiments, the connection region has a cross-sectional width of about 50 to about 500 microns, or about 100 to about 300 microns.

In various embodiments of sequestration pens the height $H_{ch}$ of the channel 122 at a proximal opening 252 can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the channel 122 can be in other ranges (e.g., a range defined by any of the endpoints listed above). The height $H_{ch}$ of the channel 122 can be selected to be in any of these ranges in regions of the channel other than at a proximal opening of a sequestration pen.

In various embodiments of sequestration pens a cross-sectional area of the channel 122 at a proximal opening 252 can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the channel 122 at a proximal opening 252 can be in other ranges (e.g., a range defined by any of the endpoints listed above).

In various embodiments of sequestration pens, the length $L_{con}$ of the connection region 254 can be in any of the following ranges: 1-200 microns, 5-150 microns, 10-100 microns, 15-80 microns, 20-60 microns, 20-500 microns, 40-400 microns, 60-300 microns, 80-200 microns, and 100-150 microns. The foregoing are examples only, and length $L_{con}$ of a connection region 254 can be in a different range than the foregoing examples (e.g., a range defined by any of the endpoints listed above).

In various embodiments of sequestration pens the width $W_{con}$ of a connection region 254 at a proximal opening 252 can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region 254 at a proximal opening 252 can be different than the foregoing examples (e.g., a range defined by any of the endpoints listed above).

In various embodiments of sequestration pens the width $W_{con}$ of a connection region 254 at a proximal opening 252 can be in any of the following ranges: 2-35 microns, 2-25 microns, 2-20 microns, 2-15 microns, 2-10 microns, 2-7 microns, 2-5 microns, 2-3 microns, 3-25 microns, 3-20 microns, 3-15 microns, 3-10 microns, 3-7 microns, 3-5 microns, 3-4 microns, 4-20 microns, 4-15 microns, 4-10 microns, 4-7 microns, 4-5 microns, 5-15 microns, 5-10 microns, 5-7 microns, 6-15 microns, 6-10 microns, 6-7 microns, 7-15 microns, 7-10 microns, 8-15 microns, and 8-10 microns. The foregoing are examples only, and the width $W_{con}$ of a connection region 254 at a proximal opening 252 can be different than the foregoing examples (e.g., a range defined by any of the endpoints listed above).

In various embodiments of sequestration pens, a ratio of the length $L_{con}$ of a connection region 254 to a width $W_{con}$ of the connection region 254 at the proximal opening 252 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 254 to a width $W_{con}$ of the connection region 254 at the proximal opening 252 can be different than the foregoing examples.

In various embodiments of microfluidic devices 100, 200, 240, 290, 500, 700, 715 $V_{max}$ can be set around 0.2, 0.3, 0.4, 0.5, 0.6, 0.7, 0.8, 0.9, 1.0, 1.1, 1.2, 1.3, 1.4, or 1.5 µL/sec.

In various embodiments of microfluidic devices having sequestration pens, the volume of an isolation region 258 of a sequestration pen can be, for example, at least $3\times10^3$, $6\times10^3$, $9\times10^3$, $1\times10^4$, $2\times10^4$, $4\times10^4$, $8\times10^4$, $1\times10^5$, $2\times10^5$, $4\times10^5$, $8\times10^5$, $1\times10^6$, $2\times10^6$, $4\times10^6$, $6\times10^6$ cubic microns, or more. In various embodiments of microfluidic devices having sequestration pens, the volume of a sequestration pen may be about $5\times10^3$, $7\times10^3$, $1\times10^4$, $3\times10^4$, $5\times10^4$, $8\times10^4$, $1\times10^5$, $2\times10^5$, $4\times10^5$, $6\times10^5$, $8\times10^5$, $1\times10^6$, $2\times10^6$, $4\times10^6$, $8\times10^6$, $1\times10^7$, $3\times10^7$, $5\times10^7$, or about $8\times10^7$ cubic microns, or more. In some embodiments, the microfluidic device has sequestration pens wherein no more than $1\times10^2$ biological cells may be maintained, and the volume of a sequestration pen may be no more than $2\times10^6$ cubic microns. In some embodiments, the microfluidic device has sequestration pens wherein no more than $1\times10^2$ biological cells may be maintained, and a sequestration pen may be no more than $4\times10^5$ cubic microns. In yet other embodiments, the microfluidic device has sequestration pens wherein no more than 50 biological cells may be maintained, a sequestration pen may be no more than $4\times10^5$ cubic microns.

In various embodiment, the microfluidic device has sequestration pens configured as in any of the embodiments discussed herein where the microfluidic device has about 100 to about 500 sequestration pens; about 200 to about 1000 sequestration pens, about 500 to about 1500 sequestration pens, about 1000 to about 2000 sequestration pens, or about 1000 to about 3500 sequestration pens.

In some other embodiments, the microfluidic device has sequestration pens configured as in any of the embodiments discussed herein where the microfluidic device has about 1500 to about 3000 sequestration pens, about 2000 to about 3500 sequestration pens, about 2500 to about 4000 sequestration pens, about 3000 to about 4500 sequestration pens, about 3500 to about 5000 sequestration pens, about 4000 to about 5500 sequestration pens, about 4500 to about 6000 sequestration pens, about 5000 to about 6500 sequestration pens, about 5500 to about 7000 sequestration pens, about 6000 to about 7500 sequestration pens, about 6500 to about 8000 sequestration pens, about 7000 to about 8500 sequestration pens, about 7500 to about 9000 sequestration pens, about 8000 to about 9500 sequestration pens, about 8500 to about 10,000 sequestration pens, about 9000 to about 10,500 sequestration pens, about 9500 to about 11,000 sequestration pens, about 10,000 to about 11,500 sequestration pens, about 10,500 to about 12,000 sequestration pens, about 11,000 to about 12,500 sequestration pens, about 11,500 to about 13,000 sequestration pens, about 12,000 to about 13,500 sequestration pens, about 12,500 to about 14,000 sequestration pens, about 13,000 to about 14,500 sequestration pens, about 13,500 to about 15,000 sequestration pens, about 14,000 to about 15,500 sequestration pens, about 14,500 to about 16,000 sequestration pens, about 15,000 to about 16,500 sequestration pens, about 15,500 to about 17,000 sequestration pens, about 16,000 to about 17,500 sequestration pens, about 16,500 to about 18,000 sequestration pens, about 17,000 to about 18,500 sequestration pens, about 17,500 to about 19,000 sequestration pens, about 18,000 to about 19,500 sequestration pens, about 18,500 to about 20,000 sequestration pens, about 19,000 to about 20,500 sequestration pens, about 19,500 to about 21,000 sequestration pens, or about 20,000 to about 21,500 sequestration pens.

Figure 2F:
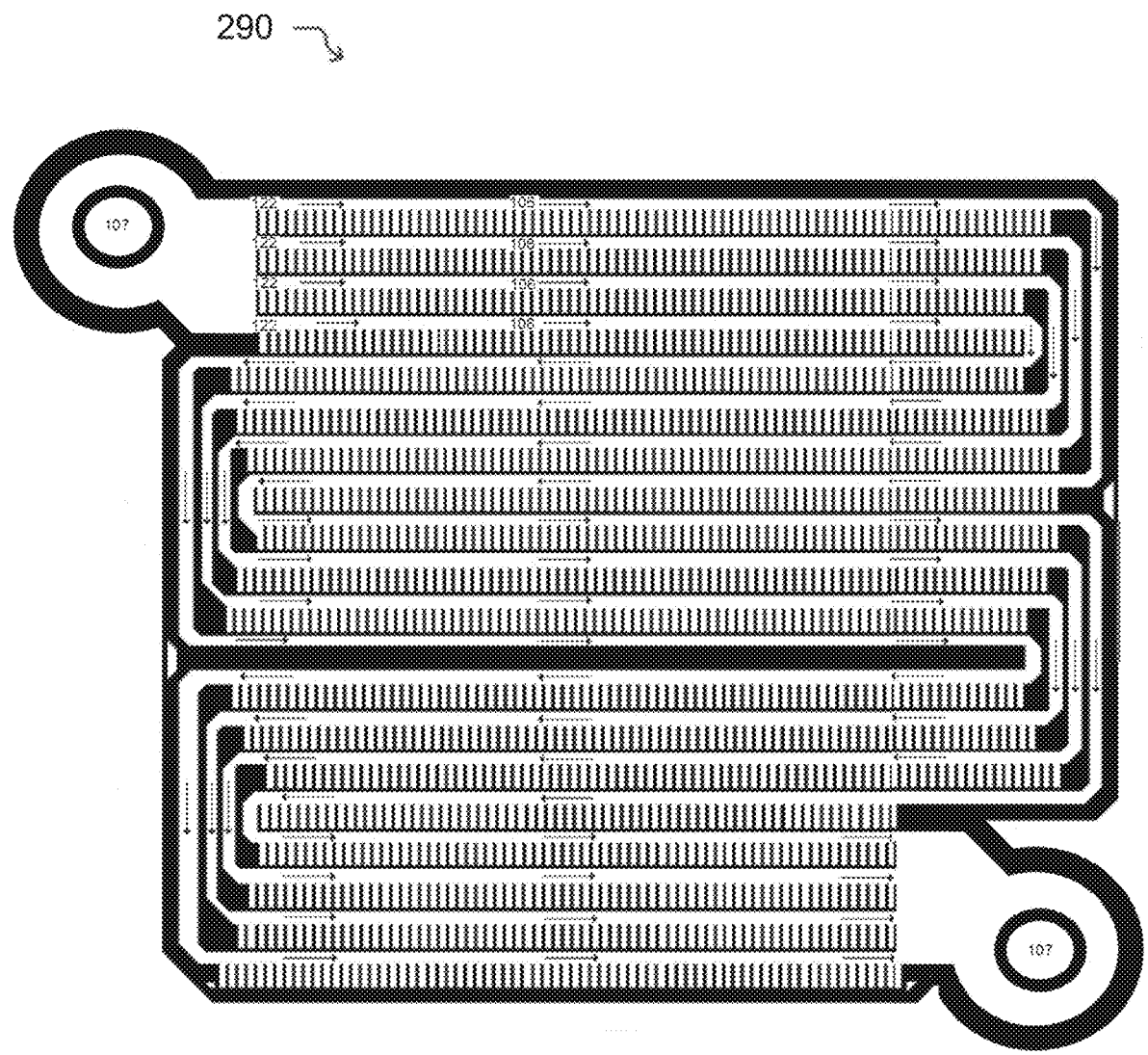
FIG. 2F illustrates a microfluidic device according to certain embodiments.

FIG. 2F illustrates a microfluidic device 290 according to one embodiment. The microfluidic device 290 is illustrated in FIG. 2F is a stylized diagram of a microfluidic device 100. In practice, the microfluidic device 290 and its constituent circuit elements (e.g. channels 122 and sequestration pens 128) would have the dimensions discussed herein. The microfluidic circuit 120 illustrated in FIG. 2F has two ports 107, four distinct channels 122 and four distinct flow paths 106. The microfluidic device 290 further comprises a plurality of sequestration pens opening off of each channel 122. In the microfluidic device illustrated in FIG. 2F, the sequestration pens have a geometry similar to the pens illustrated in FIG. 2E and thus, have both connection regions and isolation regions. Accordingly, the microfluidic circuit 120 includes both swept regions (e.g. channels 122 and portions of the connection regions 254 within the maximum penetration depth $D_p$ of the secondary flow 262) and non-swept regions (e.g. isolation regions 258 and portions of the connection regions 254 not within the maximum penetration depth $D_p$ of the secondary flow 262).

Figure 3:
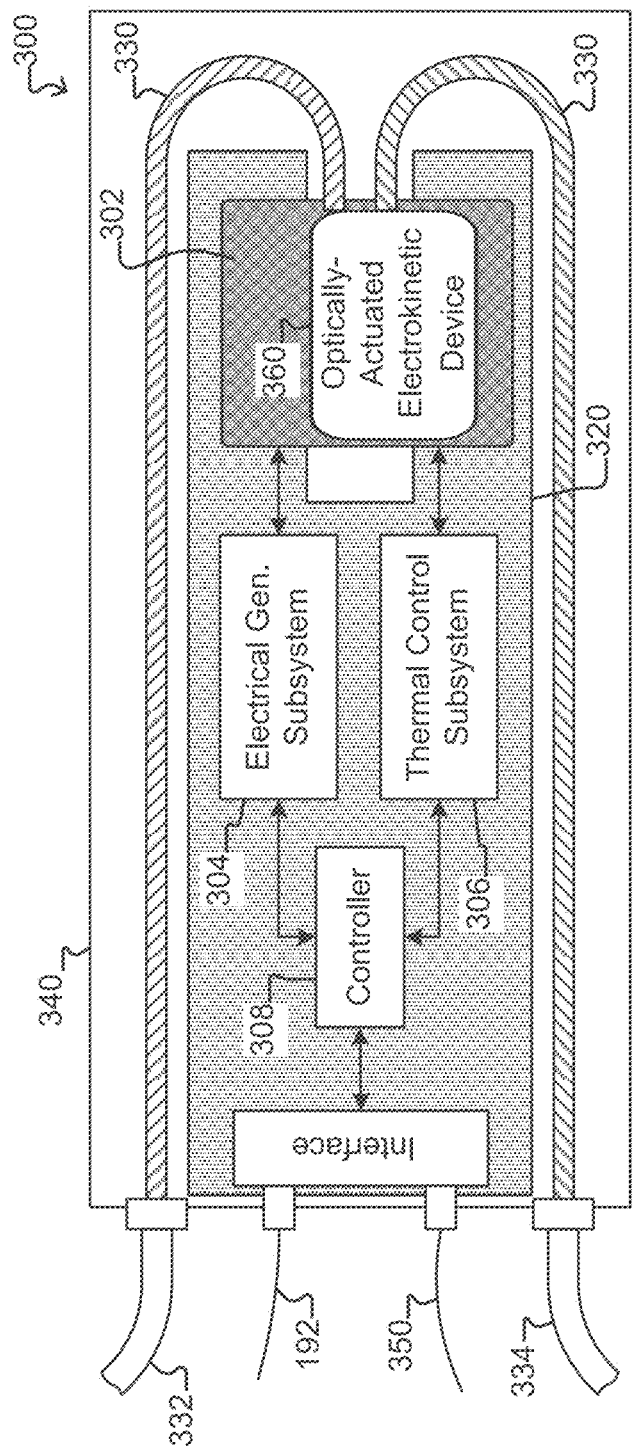
FIG. 3 illustrates a nest which can be part of a system for operating and monitoring a microfluidic device according to certain embodiments.
Figure 4:
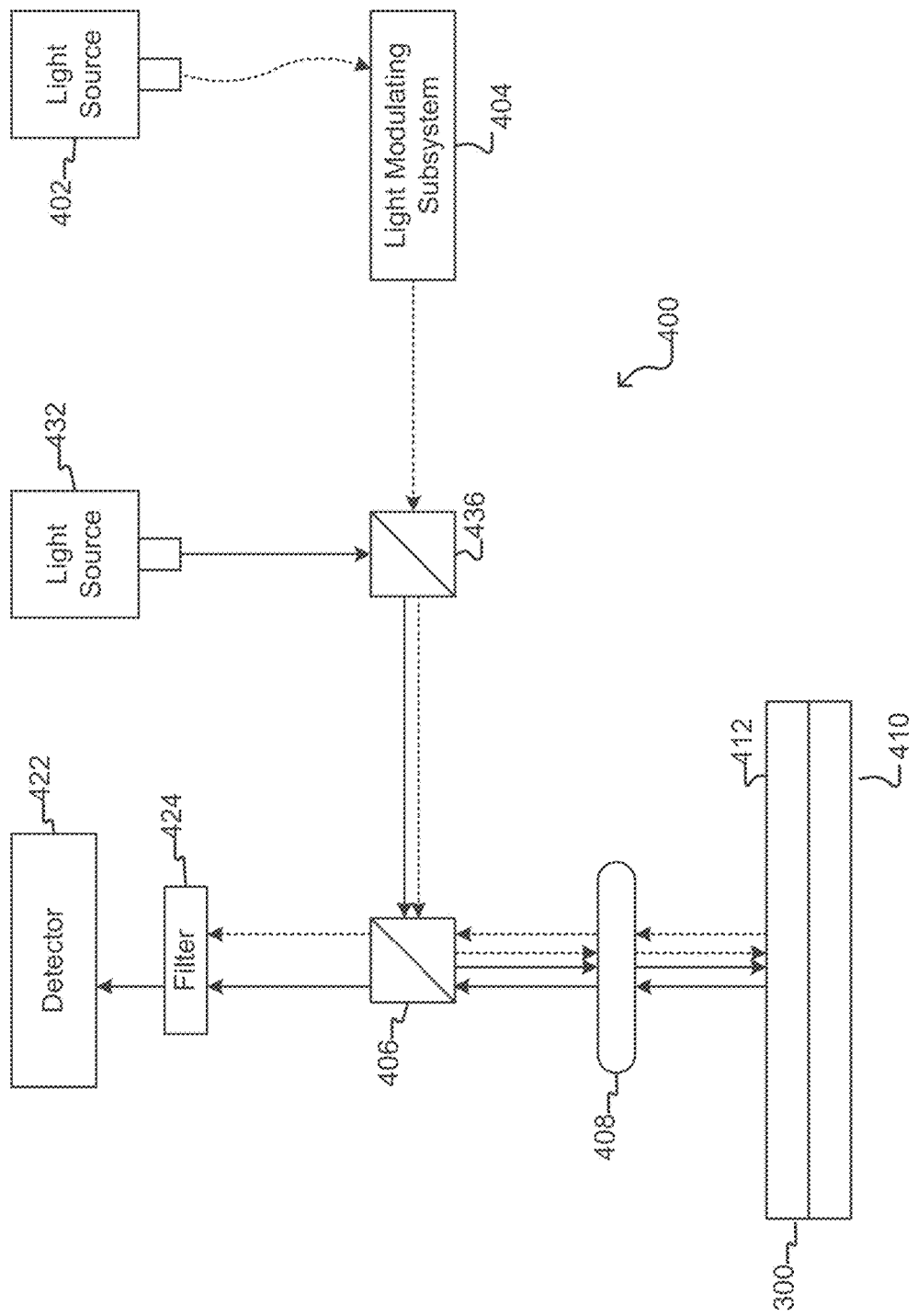
FIG. 4 illustrates an imaging device which can be part of a system for operating and monitoring a microfluidic device according to certain embodiments.

FIGS. 3 and 4 shows various embodiments of system 150 which can be used to operate and observe microfluidic devices (e.g. 100, 200, 240, 290, 500, 700, 715) according to the present disclosure. As illustrated in FIG. 3, the system 150 can include a structure ("nest") 300 configured to hold a microfluidic device 100 (not shown), or any other microfluidic device described herein. The nest 300 can include a socket 302 capable of interfacing with the microfluidic device 360 (e.g., an optically-actuated electrokinetic device 100) and providing electrical connections from power source 192 to microfluidic device 360. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 360 when it is being held by socket 302. Thus, the electrical signal generation subsystem 304 can be part of power source 192. The ability to apply a biasing voltage to microfluidic device 360 does not mean that a biasing voltage will be applied at all times when the microfluidic device 360 is held by the socket 302. Rather, in most cases, the biasing voltage will be applied intermittently, e.g., only as needed to facilitate the generation of electrokinetic forces, such as dielectrophoresis or electro-wetting, in the microfluidic device 360.

As illustrated in FIG. 3, the nest 300 can include a printed circuit board assembly (PCBA) 320. The electrical signal generation subsystem 304 can be mounted on and electrically integrated into the PCBA 320. The exemplary support includes socket 302 mounted on PCBA 320, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 360 held by the socket 302. In certain embodiments, the oscilloscope measures the waveform at a location proximal to the microfluidic device 360 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1) to perform functions and analysis. In the embodiment illustrated in FIG. 3 the controller 308 communicates with a master controller 154 through an interface 310 (e.g., a plug or connector).

in some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 360 and then adjust its own output voltage as needed such that the measured voltage at the microfluidic device 360 is the desired value. In some embodiments, the waveform amplification circuit can have a +6.5V to −6.5V power supply generated by a pair of DC-DC converters mounted on the PCBA 320, resulting in a signal of up to 13 Vpp at the microfluidic device 100.

As illustrated in FIG. 3, the support structure 300 can further include a thermal control subsystem 306. The thermal control subsystem 306 can be configured to regulate the temperature of microfluidic device 360 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 360. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 330 configured to circulate cooled fluid through the cooling block. In the embodiment illustrated in FIG. 3, the support structure 300 comprises an inlet 332 and an outlet 334 to receive cooled fluid from an external reservoir (not shown), introduce the cooled fluid into the fluidic path 330 and through the cooling block, and then return the cooled fluid to the external reservoir. In some embodiments, the Peltier thermoelectric device, the cooling unit, and/or the fluidic path 330 can be mounted on a casing 340 of the support structure 300. In some embodiments, the thermal control subsystem 306 is configured to regulate the temperature of the Peltier thermoelectric device so as to achieve a target temperature for the microfluidic device 360. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit which includes a resistor (e.g., with resistance 1 kOhm+/−0.1%, temperature coefficient+/−0.02 ppm/CO) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 350 which allows the microprocessor of the controller 308 to communicate with an external master controller 154 via the interface 310. In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 350, the electrical signal generation subsystem 308 and the thermal control subsystem 306 can communicate with the external master controller 154. In this manner, the master controller 154 can, among other things, assist the electrical signal generation subsystem 308 by performing scaling calculations for output voltage adjustments. A Graphical User Interface (GUI) provided via a display device 170 coupled to the external master controller 154, can be configured to plot temperature and waveform data obtained from the thermal control subsystem 306 and the electrical signal generation subsystem 308, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 404. The light modulating subsystem 404 can include a digital mirror device (DMD) or a microshutter array system (MSA), either of which can be configured to receive light from a light source 402 and transmits a subset of the received light into an optical train of microscope 400. Alternatively, the light modulating subsystem 404 can include a device that produces its own light (and thus dispenses with the need for a light source 402), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 404 can be, for example, a projector. Thus, the light modulating subsystem 404 can be capable of emitting both structured and unstructured light. One example of a suitable light modulating subsystem 404 is the Mosaic™ system from Andor Technologies™. In certain embodiments, imaging module 164 and/or motive module 162 of system 150 can control the light modulating subsystem 404.

In certain embodiments, the imaging device 194 further comprises a microscope 400. In such embodiments, the nest 300 and light modulating subsystem 404 can be individually configured to be mounted on the microscope 400. The microscope 400 can be, for example, a standard research-grade light microscope or fluorescence microscope. Thus, the nest 300 can be configured to be mounted on the stage 410 of the microscope 400 and/or the light modulating subsystem 404 can be configured to mount on a port of microscope 400. In other embodiments, the nest 300 and the light modulating subsystem 404 described herein can be integral components of microscope 400.

In certain embodiments, the microscope 400 can further include one or more detectors 422. In some embodiments, the detector 422 is controlled by the imaging module 164. The detector 422 can include an eye piece, a charge-coupled device (CCD), a camera (e.g., a digital camera), or any combination thereof. If at least two detectors 422 are present, one detector can be, for example, a fast-frame-rate camera while the other detector can be a high sensitivity camera. Furthermore, the microscope 400 can include an optical train configured to receive reflected and/or emitted light from the microfluidic device 360 and focus at least a portion of the reflected and/or emitted light on the one or more detectors 422. The optical train of the microscope can also include different tube lenses (not shown) for the different detectors, such that the final magnification on each detector can be different.

In certain embodiments, imaging device 194 is configured to use at least two light sources. For example, a first light source 402 can be used to produce structured light (e.g., via the light modulating subsystem 404) and a second light source 432 can be used to provide unstructured light. The first light source 402 can produce structured light for optically-actuated electrokinesis and/or fluorescent excitation, and the second light source 432 can be used to provide bright field illumination. In these embodiments, the motive module 162 can be used to control the first light source 404 and the imaging module 164 can be used to control the second light source 432. The optical train of the microscope 400 can be configured to (1) receive structured light from the light modulating subsystem 404 and focus the structured light on at least a first region in a microfluidic device, such as an optically-actuated electrokinetic device, when the device is being held by the support structure 200, and (2) receive reflected and/or emitted light from the microfluidic device and focus at least a portion of such reflected and/or emitted light onto detector 422. The optical train can be further configured to receive unstructured light from a second light source and focus the unstructured light on at least a second region of the microfluidic device, when the device is held by the support structure 300. In certain embodiments, the first and second regions of the microfluidic device can be overlapping regions. For example, the first region can be a subset of the second region.

In FIG. 3B, the first light source 402 is shown supplying light to a light modulating subsystem 404, which provides structured light to the optical train of the microscope 400. The second light source 432 is shown providing unstructured light to the optical train via a beam splitter 436. Structured light from the light modulating subsystem 404 and unstructured light from the second light source 432 travel from the beam splitter 436 through the optical train together to reach a second beam splitter 436 (or dichroic filter 406, depending on the light provided by the light modulating subsystem 404), where the light gets reflected down through the objective 408 to the sample plane 412. Reflected and/or emitted light from the sample plane 412 then travels back up through the objective 408, through the beam splitter and/or dichroic filter 406, and to a dichroic filter 424. Only a fraction of the light reaching dichroic filter 424 passes through and reaches the detector 422.

In some embodiments, the second light source 432 emits blue light. With an appropriate dichroic filter 424, blue light reflected from the sample plane 412 is able to pass through dichroic filter 424 and reach the detector 422. In contrast, structured light coming from the light modulating subsystem 404 gets reflected from the sample plane 412, but does not pass through the dichroic filter 424. In this example, the dichroic filter 424 is filtering out visible light having a wavelength longer than 495 nm. Such filtering out of the light from the light modulating subsystem 404 would only be complete (as shown) if the light emitted from the light modulating subsystem did not include any wavelengths shorter than 495 nm. In practice, if the light coming from the light modulating subsystem 404 includes wavelengths shorter than 495 nm (e.g., blue wavelengths), then some of the light from the light modulating subsystem would pass through filter 424 to reach the detector 422. In such an embodiment, the filter 424 acts to change the balance between the amount of light that reaches the detector 422 from the first light source 402 and the second light source 432. This can be beneficial if the first light source 402 is significantly stronger than the second light source 432. In other embodiments, the second light source 432 can emit red light, and the dichroic filter 424 can filter out visible light other than red light (e.g., visible light having a wavelength shorter than 650 nm).

Blocking Solutions and Blocking Agents.

Without intending to be limited by theory, the culture and expansion of T cells within a microfluidic device is facilitated (i.e., the T cells exhibit increased viability and greater expansion) when one or more inner surfaces of the microfluidic device have been conditioned or coated so as to present a layer of organic and/or hydrophilic molecules that provides the primary interface between the microfluidic device and T cells grown therein. In some embodiments, one or more of the inner surfaces of the microfluidic device (e.g. the inner surface of the electrode activation substrate of a DEP-configured microfluidic device, the cover of the microfluidic device, and/or the surfaces of the circuit material) are treated with a coating solution and/or coating agent to generate the desired layer of organic and/or hydrophilic molecules. In some embodiments, the T cells that are to be cultured and, optionally, expanded in the microfluidic device are imported in a coating solution that includes one or more coating agents.

In other embodiments, the inner surface(s) of the microfluidic device (e.g., a DEP-configured microfluidic device) are treated or "primed" with a coating solution comprising a coating agent prior to introduction of the T cells into the microfluidic device. Any convenient coating agent/coating solution can be used, including but not limited to: serum or serum factors, bovine serum albumin (BSA), polymers, detergents, enzymes, and any combination thereof. In some specific embodiments, a coating agent will be used to treat the inner surface(s) of the microfluidic device. In one example, a polymer comprising alkylene ether moieties can be included as a coating agent in the coating solution. A wide variety of alkylene ether containing polymers may be suitable. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In some embodiments, a coating solution can comprise various proteins and/or peptides as coating agents. In a specific embodiment, a coating solution that finds use in the present disclosure includes a protein such as albumin (e.g. BSA) and/or serum (or a combination of multiple different sera) comprising albumin and/or one or more other similar proteins as coating agents. The serum can be from any convenient source, including but not limited to fetal calf serum, sheep serum, goat serum, horse serum, and the like. In certain embodiments, BSA in a blocking solution is present in a range of form about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a coating solution is present in a range of from about 20% (v/v) to about 50% v/v, including 25%, 30%, 35%, 40%, 45%, or more or anywhere in between. In some embodiments, BSA is present as a coating agent in a coating solution at 5 mg/mL, whereas in other embodiments, BSA is present as a coating agent in a coating solution at 70 mg/mL. In certain embodiments, serum is present as a coating agent in a coating solution at 30%.

Coating Materials.

Depending on the embodiment, any of the foregoing coating agents/coating solutions can be replaced by or used in combination with various coating materials used to coat one or more of the inner surface(s) of the microfluidic device (e.g., a DEP-configured and/or EW-configured microfluidic device). In some embodiments, at least one surface of the microfluidic device includes a coating material that provides a layer of organic and/or hydrophilic molecules suitable for T cell culture and expansion. In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

Polymer-Based Coating Materials.

The at least one inner surface may include a coating material that comprises a polymer. The polymer may be covalently or non-covalently bound (or linked) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the coating material may include a polymer containing carboxylic acid moieties. The carboxylic acid subunit may be an alkyl, alkenyl or aromatic moiety containing subunit. One non-limiting example is polylactic acid (PLA).

In other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. These latter exemplary polymers are polyelectrolytes and may alter the characteristics of the surface to provides a layer of organic and/or hydrophilic molecules suitable for culture and expansion of T cells.

In some embodiments, the coating material may include a polymer containing urethane moieties, such as, but not limited to polyurethane.

In other embodiments, the coating material may include a polymer containing phosphate moieties, either at a terminus of the polymer backbone or pendant from the backbone of the polymer.

In other embodiments, the coating material may include a polymer containing saccharide moieties. In a non-limiting example, polysaccharides such as those derived from algal or fungal polysaccharides such as xanthan gum or dextran may be suitable to form a material which may reduce or prevent cell sticking in the microfluidic device. For example, a dextran polymer having a size about 3 Kda may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation. A nucleic acid containing polymer may include a polyelectrolyte which may provide a layer of organic and/or hydrophilic molecules suitable for T cell culture and expansion.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA). In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In further embodiments, the coating material may include a polymer including amine moieties. The polyamino polymer may include a natural polyamine polymer or a synthetic polyamine polymer. Examples of natural polyamines include spermine, spermidine, and putrescine.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently linked coating materials. In some embodiments, the at least one inner surface includes covalently linked molecules that provide a layer of organic and/or hydrophilic molecules suitable for T cell culture and expansion within the microfluidic device. The covalently linked molecules include a linking group, wherein the linking group is covalently linked to one or more surfaces of the microfluidic device. The linking group is also covalently linked to a moiety configured to provide a layer of organic and/or hydrophilic molecules suitable for T cell culture and expansion. The surface to which the linking group links may include a surface of the substrate of the microfluidic device which, for embodiments in which the microfluidic device includes a DEP configuration, can include silicon and/or silicon dioxide. In some embodiments, the covalently linked coating materials coat substantially all of the inner surfaces of the microfluidic device.

In some embodiments, the covalently linked moiety configured to provide a layer of organic and/or hydrophilic molecules suitable for T cell culture and expansion may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

The covalently linked moiety configured to provide a layer of organic and/or hydrophilic molecules suitable for T cell culture and expansion in the microfluidic device may be any polymer as described herein, and may include one or more polymers containing alkylene oxide moieties, carboxylic acid moieties, saccharide moieties, sulfonic acid moieties, phosphate moieties, amino acid moieties, nucleic acid moieties, or amino moieties.

In other embodiments, the covalently linked moiety configured to provide a layer of organic and/or hydrophilic molecules suitable for T cell culture and expansion in the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety.

In some embodiments, the covalently linked moiety may be an alkyl group that comprises carbon atoms that form a linear chain (e.g., a linear chain of at least 10 carbons, or at least 14, 16, 18, 20, 22, or more carbons). Thus, the alkyl group may be an unbranched alkyl. In some embodiments, the alkyl group may include a substituted alkyl group (e.g., some of the carbons in the alkyl group can be fluorinated or perfluorinated). The alkyl group may comprise a linear chain of substituted (e.g., fluorinated or perfluorinated) carbons joined to a linear chain of non-substituted carbons. For example, the alkyl group may include a first segment, which may include a perfluoroalkyl group, joined to a second segment, which may include a non-substituted alkyl group. The first and second segments may be joined directly or indirectly (e.g., by means of an ether linkage). The first segment of the alkyl group may be located distal to the linking group, and the second segment of the alkyl group may be located proximal to the linking group. In other embodiment, the alkyl group may include a branched alkyl group and may further have one or more arylene group interrupting the alkyl backbone of the alkyl group. In some embodiments, a branched or arylene-interrupted portion of the alkyl or fluorinated alkyl group is located at a point distal to the linking group and the covalent linkage to the surface.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the sequestration pens and/or flow regions (e.g., channels).

The coating material may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having covalently charged moieties attached to an alkyl or fluoroalkyl chain having a greater number of methylene or fluoromethylene units. In some embodiments, the coating material having more than one kind of covalently linked moiety may be designed such that a first set of molecules which have a greater number of backbone atoms, and thus a greater length from the covalent attachment to the surface, may provide capacity to present bulkier moieties at the coated surface, while a second set of molecules having different, less sterically demanding termini and fewer backbone atoms can help to functionalize the entire substrate surface and thereby prevent undesired adhesion or contact with silicon or alumina making up the substrate itself. In another example, the covalently linked moieties may provide a zwitterionic surface presenting alternating charges in a random fashion on the surface.

Conditioned surface properties. In some embodiments, the covalently linked moieties may form a monolayer when covalently linked to the surface of the microfluidic device (e.g., a DEP configured substrate surface). In some embodiments, the conditioned surface formed by the covalently linked moieties may have a thickness of less than 10 nm (e.g., less than 5 nm, or about 1.5 to 3.0 nm). In other embodiments, the conditioned surface formed by the covalently linked moieties may have a thickness of about 10 nm to about 50 nm. In some embodiments, the conditioned surface does not require a perfectly formed monolayer to be suitably functional for operation within a DEP-configured microfluidic device.

In various embodiments, the coating material of the microfluidic device may provide desirable electrical properties. Without intending to be limited by theory, one factor that impacts robustness of a surface coated with a particular coating material is intrinsic charge trapping. Different coating materials may trap electrons, which can lead to breakdown of the coating material. Defects in the coating material may increase charge trapping and lead to further breakdown of the coating material. Similarly, different coating materials have different dielectric strengths (i.e. the minimum applied electric field that results in dielectric breakdown), which may impact charge trapping. In certain embodiments, the coating material can have an overall structure (e.g., a densely-packed monolayer structure) that reduces or limits that amount of charge trapping.

Aside from the composition of the coating material, other factors such as physical (and electrical) thickness of the coating material can impact the generation of DEP force and/or electrowetting force by a substrate in a microfluidic device. Various factors can alter the physical and electrical thickness of the coating material, including the manner in which the coating material is deposited on the substrate (e.g. vapor deposition, liquid phase deposition, spin coating, or electrostatic coating). The physical thickness and uniformity of the coating material can be measured using an ellipsometer.

Besides their electrical properties, the coating material may have properties that are beneficial in use with biological molecules. For example, coating materials that contain fluorinated (or perfluorinated) alkyl groups may provide a benefit relative to unsubstituted alkyl groups in reducing the amount of surface fouling. Surface fouling, as used herein, refers to the amount of material indiscriminately deposited on the surface of the microfluidic device, which may include permanent or semi-permanent deposition of biomaterials such as protein and degradation products, nucleic acids, and respective degradation products. Such fouling can increase the amount of adhesion of biological micro-objects to the surface.

Various electrical and functional properties for different coating materials that can be used in microfluidic devices are included in the table below.

Aside from the composition of the conditioned surface, other factors such as physical thickness of the hydrophobic material can impact DEP force. Various factors can alter the physical thickness of the conditioned surface, such as the manner in which the conditioned surface is formed on the substrate (e.g. vapor deposition, liquid phase deposition, spin coating, flooding, and electrostatic coating). The physical thickness and uniformity of the conditioned surface can be measured using an ellipsometer.

In addition to its electrical properties, the conditioned surface may also have properties that are beneficial in use with biological molecules. For example, a conditioned surface that contains fluorinated (or perfluorinated) carbon chains may provide a benefit relative to alkyl-terminated chains in reducing the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Linking Group to Surface.

The covalently linked moieties forming the coating material are attached to the surface via a linking group. The linking group may be a siloxy linking group formed by the reaction of a siloxane-containing reagent with oxides of the substrate surface, which can include silicon oxide (e.g., for a DEP-configured substrate) or aluminum oxide or hafnium oxide (e.g., for a EW-configured substrate). In some other embodiments, the linking group may be a phosphonate ester formed by the reaction of a phosphonic acid containing reagent with the oxides of the substrate surface.

Multi-Part Conditioned Surface.

The covalently linked coating material may be formed by reaction of a molecule which already contains the moiety configured to provide a layer of organic and/or hydrophilic molecules suitable for T cell culture and expansion in the microfluidic device (e.g., an alkyl siloxane reagent or a fluoro-substituted alkyl siloxane reagent, which may include a perfluoroalkyl siloxane reagent), as is described below. Alternatively, the covalently linked coating material may be formed by coupling the moiety configured provide a layer of organic and/or hydrophilic molecules suitable for T cell culture and expansion to a surface modifying ligand that itself is covalently linked to the surface.

Methods of Preparing a Covalently Linked Coating Material.

In some embodiments, a coating material that is covalently linked to the surface of a microfluidic device (e.g., including at least one surface of the sequestration pens and/or flow regions) has a structure of Formula 1.

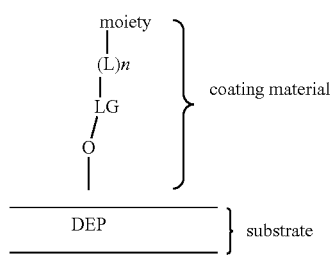

Formula 1

The coating material may be linked covalently to oxides of the surface of a DEP-configured substrate. The DEP-configured substrate may comprise silicon or alumina or hafnium oxide, and oxides may be present as part of the native chemical structure of the substrate or may be introduced as discussed below.

The coating material may be attached to the oxides via a linking group ("LG"), which may be a siloxy or phosphonate ester group formed from the reaction of a siloxane or phosphonic acid group with the oxides. The moiety configured to provide a layer of organic and/or hydrophilic molecules suitable for T cell culture and expansion in the microfluidic device can be any of the moieties described herein. The linking group LG may be directly or indirectly connected to the moiety configured to provide a layer of organic and/or hydrophilic molecules suitable for T cell culture and expansion in the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and phosphorus atoms, subject to chemical bonding limitations as is known in the art. It may be interrupted with any combination of one or more moieties selected from the group consisting of ether, amino, carbonyl, amido, or phosphonate groups, in some non-limiting examples. Additionally, the linker L may have one or more arylene, heteroarylene, or heterocyclic groups interrupting the backbone of the linker. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

When the moiety configured to provide a layer of organic and/or hydrophilic molecules suitable for T cell culture and expansion in the microfluidic device is added to the surface of the substrate in a one step process, a molecule of Formula 2 may be used to introduce the coating material:

moiety-(L)$n$-LG.  Formula 2

In some embodiments, the moiety configured to provide a layer of organic and/or hydrophilic molecules suitable for T cell culture and expansion in the microfluidic device may be added to the surface of the substrate in a multi-step process. When the moiety configured to provide a layer of organic and/or hydrophilic molecules suitable for T cell culture and expansion is coupled to the surface in a step wise fashion, the linker L may further include a coupling group CG, as shown in Formula 3.

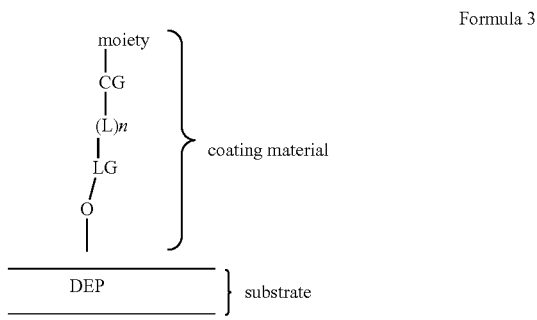

Formula 3

In some embodiments, the coupling group CG represents the resultant group from reaction of a reactive moiety $R_x$ and a reactive pairing moiety $R_{px}$ (i.e., a moiety configured to react with the reactive moiety $R_x$). For example, one typical coupling group CG may include a carboxamidyl group, which is the result of the reaction of an amino group with a derivative of a carboxylic acid, such as an activated ester, an acid chloride or the like. Other CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end (i.e., the end proximal to the moiety configured to provide a layer of organic and/or hydrophilic molecules suitable for T cell culture and expansion in the microfluidic device) of a linker L. In some other embodiments, the coupling group CG may interrupt the backbone of the linker L. In some embodiments, the coupling group CG is triazolylene, which is the result of a reaction between an alkyne group and an azide group, either of which may be the reactive moiety $R_x$ or the reactive pairing moiety $R_{px}$, as is known in the art for use in Click coupling reactions. A triazolylene group may also be further substituted. For example, a dibenzocyclocooctenyl fused triazolylene group may result from the reaction of a moiety bound to a dibenzocyclooctynyl reactive pairing moiety $R_{px}$ with an azido reactive moiety $R_x$ of the surface modifying molecule, which are described in more detail in the following paragraphs. A variety of dibenzocyclooctynyl modified molecules are known in the art or may be synthesized to incorporate a moiety configured to provide a layer of organic and/or hydrophilic molecules suitable for T cell culture and expansion.

When the coating material is formed in a multi-step process, the moiety configured to provide a layer of organic and/or hydrophilic molecules suitable for T cell culture and expansion in the microfluidic device may be introduced by reaction of a moiety-containing reagent (Formula 5) with a substrate having a surface modifying ligand covalently linked thereto (Formula 6).

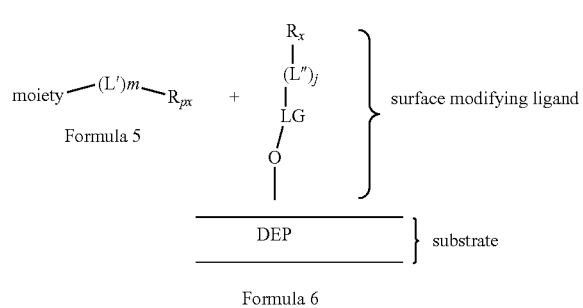

Formula 6

The modified surface of Formula 4 has a surface modifying ligand attached thereto, which has a formula of -LG-(L")j-$R_x$, which is linked to the oxide of the substrate and is formed similarly as described above for the conditioned surface of Formula 1. The surface of the substrate can be a DEP-configured substrate surface as described above, and can include oxides either native to the substrate or introduced therein. The linking group LG is as described above. A linker L" may be present (j=1) or absent (j=0). The linker L" may have a linear portion where a backbone of the linear portion may include 1 to 100 non-hydrogen atoms selected from of any combination of silicon, carbon, nitrogen, oxygen, sulfur and phosphorus atoms, subject to chemical bonding limitations as is known in the art. It may be interrupted with any combination of ether, amino, carbonyl, amido, or phosphonate groups, in some non-limiting examples. Additionally, the linker L" may have one or more arylene, heteroarylene, or heterocyclic groups interrupting the backbone of the linker. In some embodiments, the backbone of the linker L" may include 10 to 20 carbon atoms. In other embodiments, the backbone of the linker L" may include about 5 atoms to about 100 atoms; about 10 atoms to about 80 atoms, about 10 atoms to about 50 atoms, or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

A reactive moiety $R_x$ is present at the terminus of the surface modifying ligand distal to the covalent linkage of the surface modifying ligand with the surface. The reactive moiety $R_x$ is any suitable reactive moiety useful for coupling reactions to introduce the moiety provide a layer of organic and/or hydrophilic molecules suitable for T cell culture and expansion in the microfluidic device. In some embodiments, the reactive moiety $R_x$ may be an azido, amino, bromo, a thiol, an activated ester, a succinimidyl or alkynyl moiety.

Moiety-Containing Reagent.

The moiety-containing reagent (Formula 5) is configured to supply the moiety configured to provide a layer of organic and/or hydrophilic molecules suitable for T cell culture and expansion in the microfluidic device.

Moiety-(L')$_m$-$R_{px}$     Formula 5

The moiety configured to provide a layer of organic and/or hydrophilic molecules suitable for T cell culture and expansion in the moiety-containing reagent is linked to the surface modifying ligand by reaction of a reactive pairing moiety $R_{px}$ with the reactive moiety $R_x$. The reactive pairing moiety $R_{px}$ is any suitable reactive group configured to react with the respective reactive moiety $R_x$. In one non-limiting example, one suitable reactive pairing moiety $R_{px}$ may be an alkyne and the reactive moiety $R_x$ may be an azide. The reactive pairing moiety $R_{px}$ may alternatively be an azide moiety and the respective reactive moiety $R_x$ may be alkyne. In other embodiments, the reactive pairing moiety $R_{px}$ may be an active ester functionality and the reactive moiety $R_x$ may be an amino group. In other embodiments, the reactive pairing moiety $R_{px}$ may be aldehyde and the reactive moiety $R_x$ may be amino. Other reactive moiety-reactive pairing moiety combinations are possible, and these examples are in no way limiting.

The moiety configured to provide a layer of organic and/or hydrophilic molecules suitable for T cell culture and expansion of the moiety-containing reagent of Formula 5 may include any of the moieties described herein, including alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

The moiety configured to provide a layer of organic and/or hydrophilic molecules suitable for T cell culture and expansion of the moiety-containing reagent of Formula 5 may be directly connected (i.e., L', where m=0) or indirectly connected to the reactive pairing moiety $R_{px}$. When the reactive pairing moiety $R_{px}$ is connected indirectly to the moiety configured to provide a layer of organic and/or hydrophilic molecules suitable for T cell culture and expansion, the reactive pairing moiety $R_{px}$ may be connected to a linker L' (m=1). The reactive pairing moiety $R_{px}$ may be connected to a first end of the linker L', and the moiety configured to reduce surface fouling and/or prevent or reduce cell sticking may be connected to a second end of the linker L'. Linker L' may have a linear portion wherein a backbone of the linear portion includes 1 to 100 non-hydrogen atoms selected from of any combination of silicon, carbon, nitrogen, oxygen, sulfur and phosphorus atoms, subject to chemical bonding limitations as is known in the art. It may be interrupted with any combination of ether, amino, carbonyl, amido, or phosphonate groups, in some non-limiting examples. Additionally, the linker L' may have one or more arylene, heteroarylene, or heterocyclic groups interrupting the backbone of the linker L'. In some embodiments, the backbone of the linker L' may include 10 to 20 atoms. In other embodiments, the backbone of the linker L' may include about 5 atoms to about 100 atoms; about 10 atoms to about 80 atoms; about 10 atoms to about 50 atoms; or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

When the moiety-containing reagent (Formula 5) reacts with the surface having a surface modifying ligand (Formula 3), a substrate having a conditioned surface of Formula 2 is formed. Linker L' and linker L" then are formally part of linker L, and the reaction of the reactive pairing moiety $R_{px}$ with the reactive moiety $R_x$ yields the coupling group CG of Formula 2.

Surface Modifying Reagent.

The surface modifying reagent is a compound having a structure LG-(L")$_j$-R$_x$ (Formula 4). The linking group LG links covalently to the oxides of the surface of the substrate. The substrate may be a DEP-configured substrate and may include silicon or alumina or hafnium oxide, and oxides may be present as part of the native chemical structure of the substrate or may be introduced as discussed herein. The linking group LG may be any linking group described herein, such as a siloxy or phosphonate ester group, formed from the reaction of a siloxane or phosphonic acid group with the oxide on the surface of the substrate. The reactive moiety $R_x$ is described above. The reactive moiety $R_x$ may be connected directly (L", j=0) or indirectly via a linker L" (j=1) to the linking group LG. The linking group LG may be attached to a first end of the linker L" and the reactive moiety $R_x$ may be connected to a second end of the linker L", which will be distal to the surface of the substrate once the surface modifying reagent has been attached to the surface as in Formula 6.

deposited at a temperature of at least 110° C. (e.g., at least 120° C., 130° C., 140° C., 150° C., 160° C., etc.), for a period of at least 15 hours (e.g., at least 20, 25, 30, 35, 40, 45, or more hours). Such vapor deposition is typically performed under vacuum and in the presence of a water source, such as a hydrated sulfate salt (e.g., MgSO4.7H20). Typically, increasing the temperature and duration of the vapor deposition produces improved characteristics of the hydrophobic coating material.

The vapor deposition process can be optionally improved, for example, by pre-cleaning the cover 110, the microfluidic circuit material 116, and/or the substrate (e.g., the inner surface 208 of the electrode activation substrate 206 of a DEP-configured substrate, or a dielectric layer of the support structure 104 of an EW-configured substrate). For example, such pre-cleaning can include a solvent bath, such as an acetone bath, an ethanol bath, or a combination thereof. The solvent bath can include sonication. Alternatively, or in addition, such pre-cleaning can include treating the cover 110, the microfluidic circuit material 116, and/or the substrate in an oxygen plasma cleaner, which can remove various impurities, while at the same time introducing an oxidized surface (e.g. oxides at the surface, which may be covalently modified as described herein). The oxygen

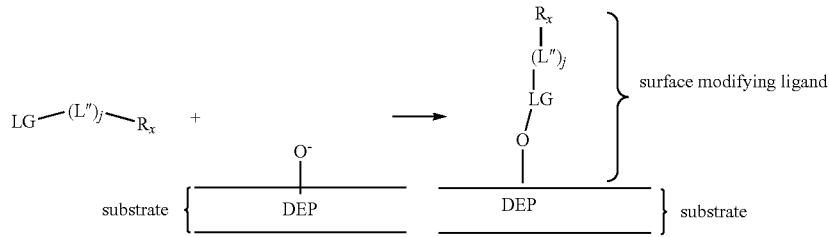

Formula 4                Formula 6

Linker L" may have a linear portion wherein a backbone of the linear portion includes 1 to 100 non-hydrogen atoms selected from of any combination of silicon, carbon, nitrogen, oxygen, sulfur and phosphorus atoms. It may be interrupted with any combination of ether, amino, carbonyl, amido, or phosphonate groups, in some non-limiting examples. Additionally, the linker L" may have one or more arylene, heteroarylene, or heterocyclic groups interrupting the backbone of the linker L". In some embodiments, the backbone of the linker L" may include 10 to 20 atoms. In other embodiments, the backbone of the linker L" may include about 5 atoms to about 100 atoms; about 10 atoms to about 80 atoms, about 10 atoms to about 50 atoms, or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

In some embodiments, the coating material (or surface modifying ligand) is deposited on the inner surfaces of the microfluidic device using chemical vapor deposition. Through chemical vapor deposition, the coating material can achieve densely-packed monolayers in which the molecules comprising the coating material are covalently bonded to the molecules of the inner surfaces of the microfluidic device. To achieve a desirable packing density, molecules comprising, for example, alkyl-terminated siloxane can be vapor plasma cleaner can be operated, for example, under vacuum conditions, at 100 W for 60 seconds. Alternatively, liquid-phase treatments, which include oxidizing agents such as hydrogen peroxide to oxidize the surface, may be used in place of an oxygen plasma cleaner. For example, a mixture of hydrochloric acid and hydrogen peroxide or a mixture of sulfuric acid and hydrogen peroxide (e.g., piranha solution, which may have a ratio of sulfuric acid to hydrogen peroxide in a range from about 3:1 to about 7:1) may be used in place of an oxygen plasma cleaner.

In some embodiments, vapor deposition is used to coat the inner surfaces of the microfluidic device 200 after the microfluidic device 200 has been assembled to form an enclosure 102 defining a microfluidic circuit 120. Deposition of a coating material comprising a densely-packed monolayer on a fully-assembled microfluidic circuit 120 may be beneficial in providing various functional properties. Without intending to be limited by theory, depositing such a coating material on a fully-assembled microfluidic circuit 120 may be beneficial in preventing delamination caused by a weakened bond between the microfluidic circuit material 116 and the electrode activation substrate 206/dielectric layer and/or the cover 110.

Figure 5:
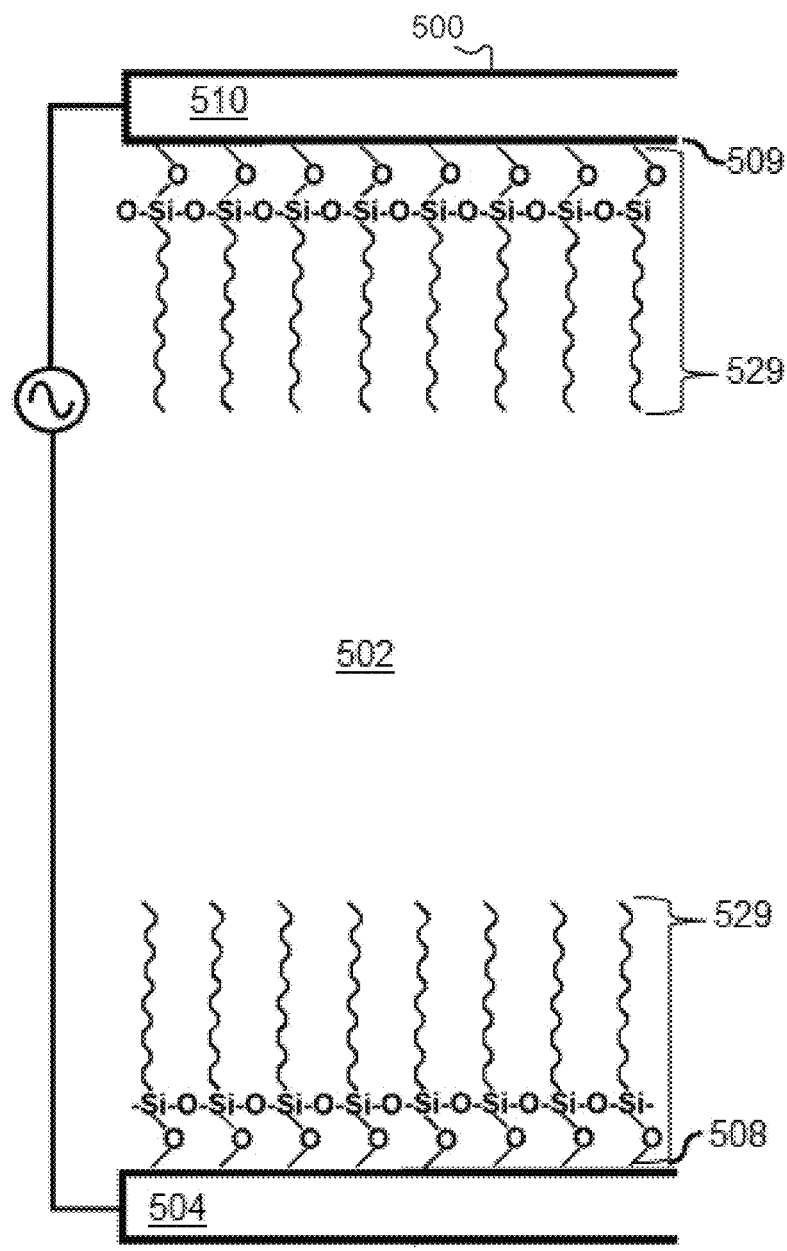
FIG. 5 illustrates a microfluidic device having a coating material that is covalently bound to the inner surface of both the substrate and the device cover according to certain embodiments.

FIG. 5 depicts a cross-sectional views of a microfluidic device 500 comprising exemplary classes of coating materials. As illustrated, the coating materials 529 (shown schematically) can comprise a monolayer of densely-packed molecules covalently bound to both the inner surface 508 of the substrate 504 and the inner surface 509 of the cover 510 of the microfluidic device 500. The coating material 529 can be disposed on all inner surfaces 508, 509 proximal to, and facing inwards towards, the enclosure 502 of the microfluidic device 500, including, in some embodiments and as discussed above, the surfaces of microfluidic circuit material (not shown) used to define circuit elements and/or structures within the microfluidic device 500. In alternate embodiments, the coating material 529 can be disposed on only one or some of the inner surfaces of the microfluidic device 500.

In the embodiment shown in FIG. 5, the coating material 529 comprises a monolayer of alkyl-terminated siloxane molecules, each molecule covalently bonded to the inner surfaces 508, 509 of the microfluidic device 500 via a siloxy group. However, any of the above-discussed coating materials 529 can be used (e.g. alkyl-terminated phosphonate ester molecules). More specifically, the alkyl group can comprise a linear chain of at least 10 carbon atoms (e.g. 10, 12, 14, 16, 18, 20, 22, or more carbon atoms) and, optionally, may be a substituted alkyl group. As discussed above, coating materials 529 that comprise a monolayer of densely-packed molecules can have beneficial functional characteristics for use in DEP configured microfluidic devices 500, such as minimal charge trapping, reduced physical/electrical thickness, and a substantially uniform surface.

In another specific embodiment, the coating material 529 can comprise a fluoroalkyl group (e.g. a fluorinated alkyl group or a perfluorinated alkyl group) at its enclosure-facing terminus (i.e. the portion of the monolayer of the coating material 529 that is not bound to the inner surfaces 508, 509 and is proximal to the enclosure 502). As discussed above, the coating material 529 can comprise a monolayer of fluoroalkyl-terminated siloxane or fluoroalkyl-terminated phosphonate ester, wherein the fluoroalkyl group is present at the enclosure-facing terminus of the coating material 529. Such a coating material 529 provides a functional benefit in providing for improved T cell culture and expansion by separating or "shielding" the T cells from the non-biological molecules (e.g., the silicon and/or silicon oxide of the substrate)

In another specific embodiments, the coating material 529 used to coat the inner surface(s) 508, 509 of the microfluidic device 500 can include anionic, cationic, or zwitterionic moieties, or any combination thereof. Without intending to be limited by theory, by presenting cationic moieties, anionic moieties, and/or zwitterionic moieties at the inner surfaces of the enclosure 502 of the microfluidic circuit 500, the coating material 529 can form strong hydrogen bonds with water molecules such that the resulting water of hydration acts as a layer (or "shield") that separates the nuclei from interactions with non-biological molecules (e.g., the silicon and/or silicon oxide of the substrate). In addition, in embodiments in which the coating material 529 is used in conjunction with blocking agents, the anions, cations, and/or zwitterions of the coating material 529 can form ionic bonds with the charged portions of blocking agents (e.g. proteins in solution) that are present in a medium 180 (e.g. a blocking solution) in the enclosure 502.

In still another specific embodiment, the coating material may comprise or be chemically modified to present a hydrophilic coating agent at its enclosure-facing terminus. In some embodiments, the coating agent may be an alkylene ether containing polymer, such as PEG. In some embodiments, the coating agent may be a polysaccharide, such as dextran. Like the charged moieties discussed above (e.g., anionic, cationic, and zwitterionic moieties), the hydrophilic coating agent can form strong hydrogen bonds with water molecules such that the resulting water of hydration acts as a layer (or "shield") that separates the nuclei from interactions with non-biological molecules (e.g., the silicon and/or silicon oxide of the substrate).

Methods of Enrichment.

Figure 11:
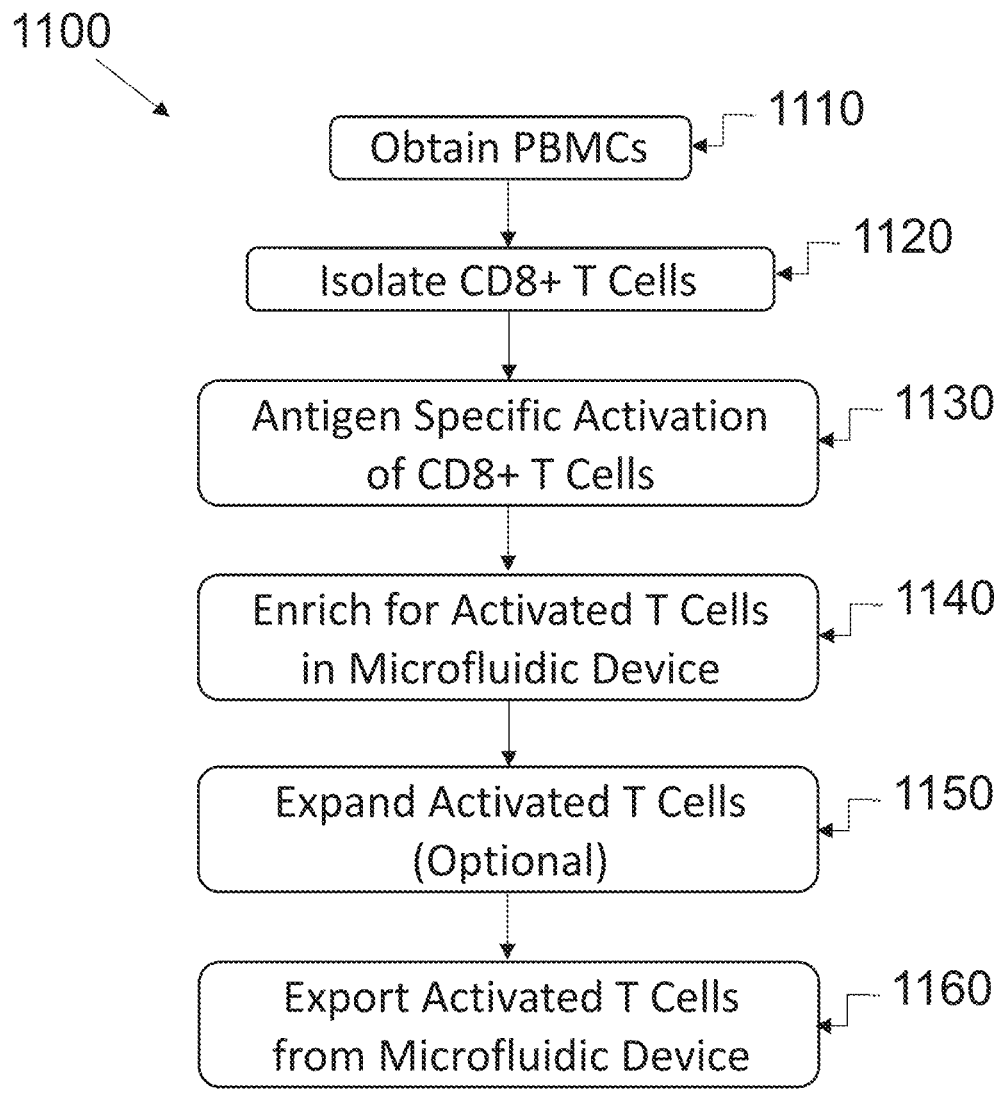
FIG. 11 is a flow chart outlining a method for enriching T lymphocytes according to certain embodiments.

The devices disclosed herein can be used to sort T lymphocytes and, for example, provide enriched populations of T lymphocytes, particularly activated T lymphocytes that are functionally responsive to an antigen of interest. FIG. 11 provides an outline of one such method 1100.

At step 1110, a sample of peripheral blood is obtained from a subject. The subject can be a human donor or some other type of animal, such as a mammal (e.g., mouse, rat, guinea pig, rabbit, sheep, pig, cow, horse, primate, or the like), a bird, a reptile, an amphibian, etc. The subject can be healthy, or the subject can be suffering from a disorder. For example, for human subjects, the disorder can be caused by a pathogenic organism, such as a bacterial pathogen, a fungal pathogen, a parasitic pathogen, or a viral pathogen. Alternatively, the disorder can be a form of cancer. For non-human animals, the animal can be suffering from any of the foregoing (i.e., infected with a pathogen, or cancer), and/or the animal can have a disorder that is a model for a corresponding human disorder.

The peripheral blood sample can be processed by leukapheresis to obtain peripheral blood mononuclear cells (PBMCs). The PBMCs can be washed and frozen for later use. Alternatively, the PBMCs can be washed and undergo further processing immediately.

At step 1120, $CD8^+$ T lymphocytes can be isolated from the PBMCs. Many different commercial kits are available for isolating $CD8^+$ T lymphocytes from PBMCs. Examples include bead-based purification kits, such as the EasySep™ Human CD8+ T Cell Enrichment kit (Stem Cell Technologies) and the EasySep™ Human Naïve $CD8^+$ T Cell Enrichment kit (Stem Cell Technologies). Different kits can be selected depending on whether all $CD8^+$ T cells are desired, or just certain sub-populations, such as naïve $CD8^+$ T cells. In some embodiments, naïve $CD8^+$ T cells can provide a good starting material for step 1130 (antigen-specific activation).

As an alternative to bead-based purification, FACS cell sorting can be used to obtain $CD8^+$ T cells, and optionally $CD8^+$ naïve T cells. For example, a fluorescently-labeled anti-CD8 antibody can be used for FACS sorting. As persons skilled in the art will understand, many different antibodies and antibody combinations can be used to get a desired population of $CD8^+$ T cells. For example, a combination of anti-CD45RO (for negative selection) and anti-CCR7 antibody (for positive selection) antibodies can be used to isolate $CD8^+$ naïve T cell populations. Additionally, anti-CD45RA and/or anti-CD62L antibodies can be used. Instead of $CD8^+$ naïve T cells, central memory T cells ($T_{CM}$) can be purified using the same antibodies mentioned above, although used differently (e.g., anti-CD45RO for positive selection, anti-CD45RA for negative selection, anti-CCR7 for positive selection, etc.)

At step 1130, the CD8+ T cell sample is contacted with a known antigen to stimulate antigen-specific activation. The known antigen can be part of an artificial antigen presenting cell (aAPC). aAPCs can be designed to present MHC Class I molecules that are bound to antigenic peptide. The MHC Class I molecules can be linked as tetramers, as described in U.S. Pat. No. 5,635,363, the entire contents of which are incorporated herein by reference. aAPCs have been described, for example, in PCT applications WO2013/086500, published Jun. 13, 2013, WO2014/160132, published Oct. 2, 2014, and WO2016/044530, published Mar. 24, 2016, the entire contents of which are incorporated herein by reference. The number of CD8$^+$ T cells contacted can be about $1\times10^5$ to about $1\times10^7$ (e.g., about $5\times10^5$ to about $5\times10^6$, or about $1\times10^6$). The ratio of aAPC:CD8$^+$ T cells can be varied. For example, the ratio can be 5:1, 4:1, 3:1, 2:1, 1:1, 1:2, 1:3, 1:4, or 1:5.

The incubation can be performed, for example, within a well of a micro-titer plate. The length of the incubation can be at least about 12 hours (e.g., about 12 hours, about 24 hours, about 36 hours, about 48 hours, about 60 hours, about 72 hours, about 84 hours, about 96 hours, about 108 hours, about 120 hours, or any range defined by two of the foregoing values). The incubation can be performed in T cell culture medium, examples of which are widely known in the art. See, for example, Ho et al. (2006), J. Immunological Methods 310:40-52, and International Application No. PCT/US17/22846, filed Mar. 16, 2017. The cell culture medium can be supplemented with a CD28 agonist (e.g., an anti-CD28 agonist antibody at 2 micrograms/mL) or the CD28 agonist can be bound to the aAPC. The culture can be maintained under standard conditions (e.g., at 37° C. under 5% $CO_2$).

As an alternative to using aAPCs, DC that have been pulsed with an antigenic peptide containing the antigen of interest can be used. Use of DCs has been described, for example, in International Application No. PCT/US17/22846, filed Mar. 16, 2017.

Many different antigenic peptides are known in the art. Examples include: the M27L peptide of Melan-A (Ho et al. (2006), referenced above); the $WT1_{126}$ peptide of the Wilms tumor protein (also described in Ho et al. (2006)); and NY-ESO-1 (Pollack et al. (2014), J. Immunother Cancer 2:36). Selection of the peptide can depend on the type of MHC Class I molecule present on the aAPCs or in the DCs.

At step 1140, the sample of CD8$^+$ T lymphocytes that has been contacted with the activating agent at step 1130 are expected to include some enlarged, activated T cells that are antigen-specific. Such T cells can be selectively enriched by flowing the sample through a microfluidic device having a post array configured to separate activated T cells from resting/naïve T cells. The microfluidic device (and the post array contained therein) can be as described in various embodiments herein. Thus, the microfluidic device can have a configuration generally as shown for microfluidic device 700 in FIG. 7A. The post array can have, for example, a predicted critical size ($D_c$) of about 6 microns, with a tilt angle $\epsilon=1/12$ radians, 25 micron gaps between posts in the same column, and triangular shaped posts having a diameter of about 50 microns. Alternatively, the microfluidic device can have a configuration generally as shown for microfluidic device 715 in FIG. 7B. The post array can have a predicted critical size ($D_c$) of about 6 microns, with a tilt angle $\epsilon=1/12$ radians, 25 micron gaps between posts in the same column, and triangular shaped posts having a diameter of about 50 microns, and the microfluidic device includes a DEP configuration.

Prior to flowing the sample through the microfluidic device, a buffer can be flowed through the device at a rapid rate (e.g., 10 to 100 microliters/sec) to eliminate bubbles. Next, the contacted/activated T cell sample from step 1140 can be flowed through the post array of the microfluidic device at a rate of about 1.0 to about 10 microliters/sec or using a pressure of about 10 psi to about 30 psi (e.g., about 20 psi).

Prior to step 1140, the incubated sample obtained from step 1130 can be labeled to identify individual T cells that specifically bind antigen. For example, the sample from step 1130 can be contacted with fluorescently-labeled soluble MHC Class I tetramers bound to an antigenic peptide (as appropriate), to facilitate the labeling and identification of antigen-specific T lymphocytes. Such labeling and identification can be used to select individual T lymphocytes for movement into a sequestration pen 725 on a microfluidic device, such as device 715 of FIG. 7B, and subsequent cloning. Alternatively, following the cloning of individual T lymphocytes in the sequestration pens 725, fluorescently-labeled soluble MHC Class I tetramers bound antigenic peptide (as appropriate) can be flowed into the sorting channel 720 of microfluidic device 715 and allowed to diffuse into the sequestration pens 725, whereupon antigen-specific T lymphocyte clones can be labeled and identified. Such labeling and identification can be used to select T lymphocytes clones for export and subsequent analysis, as discussed below.

At step 1150, an enriched sample of activated CD8+T lymphocytes can optionally be expanded within the microfluidic device. For example, after sample passes through the post array in the microfluidic device, the flow of fluid through the device can be stopped. Provided that the microfluidic device includes sequestration pens, such as shown for microfluidic device 715 of FIG. 7B, individual T lymphocytes can be selected and moved to corresponding sequestration pens and the isolated T lymphocytes can be grown into clonal populations of cells. The cloning of activated T lymphocytes within a microfluidic device in this manner has been described, for example, in International Application No. PCT/US17/22846, filed Mar. 16, 2017, referred to above.

At step 1160, T cells that were activated by contact with the activating agent can be exported from the microfluidic device. For a device such as microfluidic device 700 of FIG. 7A, such export occurs immediately after sorting, and the activated T cells are collected from the sorted outlet 708. For a device such as microfluidic device 715 of FIG. 7B, T cell clones that were successfully expanded in the sequestration pens 725 can be moved back into the channel 720 (e.g., second channel) and exported through outlet 708/710 using fluid flow. Movement of the activated T cell clones out of the pens can be accomplished, for example, using DEP force, which can be optically actuated such as with OEP.

Regardless of the exact configuration of the microfluidic device and the timing of export, the activated T cells can be collected and, optionally, further expanded off chip or tested in various assays. For example, select T cells can be process for TCR sequencing to identify antigen-specific TCRs. Alternatively, the enriched sample of activated CD8+T lymphocytes that is collected from the outlet of the microfluidic device 700 can be expanded using a rapid expansion protocol (REP) prior to being introduced into the patient suffering from melanoma. REPs are known in the art. See, for example, Ho et al. (2006), referenced above.

EXAMPLES

Example 1: Post Array-Based Separation of Activated Human T Lymphocytes and Resting Human T Lymphocytes in a Microfluidic Device CD3$^+$ human T lymphocytes isolated from peripheral blood were activated by mixing with anti-CD3/anti-CD28 magnetic beads (DYNABEADS™, Thermo Fisher Scientific, Inc.) at a ratio of 1 bead/1 cell. The mixture was incubated for 5 hours in a 5% $CO_2$ incubator at 37° C.

Following the incubation, the activated T cell/bead mixture was resuspended and labeled with a CellTracker™ fluorescent label (Thermo Fisher Scientific, Inc.). The labeled T cells were then flowed through a microfluidic device having a post array with a predicted critical size ($D_c$) of about 9 microns, at a flow rate of about 0.1 microliter/second. The post array featured a tilt angle $\varepsilon=\frac{1}{15}$ radians, with a 30 micron gap between posts in the same column. The posts had a circular shape with a diameter of about 50 microns.

Figure 8:
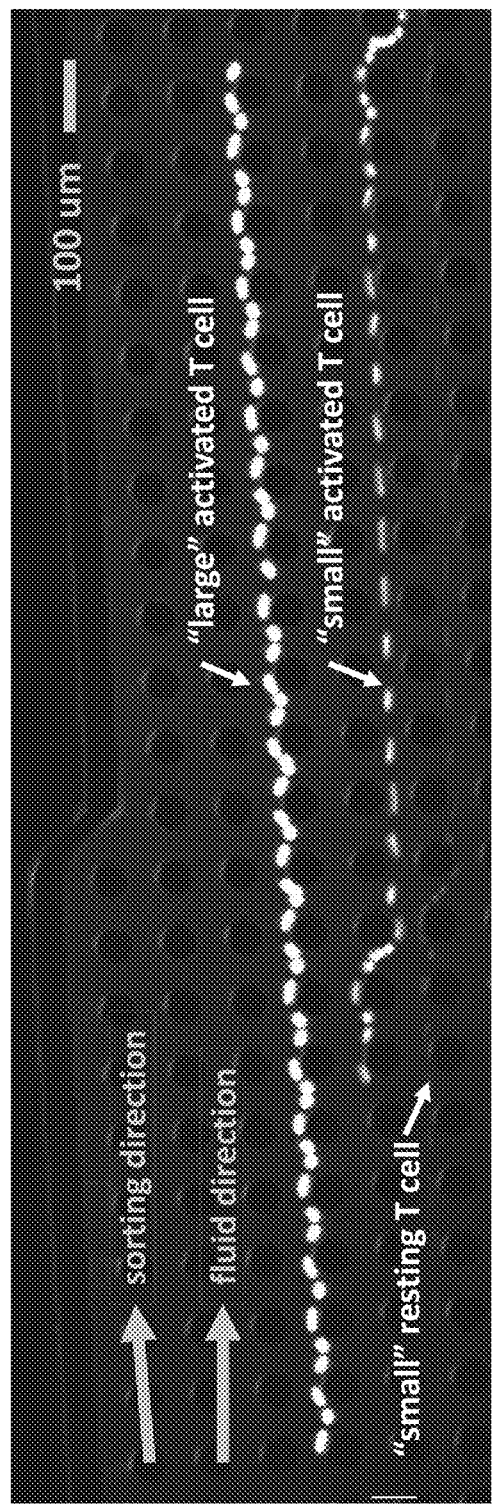
FIG. 8 is an image of a portion of a microfluidic device having an array of posts configured to separate "large" activated T lymphocytes from "small" activated T lymphocytes, and T lymphocytes fluorescently labeled to allow their detection within the array.

The labeled T cells were imaged as they flowed through the post array. As shown in FIG. 8, activated T cells having a "larger" size traveled through the post array in the "sorting direction" of the array (i.e., generally along the axis defined by the rows of posts), while activated T cells having a "smaller" size traveled through the post array generally in the direction of fluid flow through the array (i.e., generally along the direction of the flow path defined by the region of the microfluidic device that contained the post array). Resting T cells also traveled through the post array generally in the direction of fluid flow through the array.

This experiment demonstrates that T lymphocytes have different sizes and can be sorted based on such size differences by flowing them through an appropriately configured post array.

Example 2: Enrichment of Activated Human T Lymphocytes after Processing a Mixed Population of Activated and Resting T Lymphocytes in a Microfluidic Device CD3$^+$ human T lymphocytes isolated from peripheral blood were activated by mixing with anti-CD3/anti-CD28 magnetic beads (DYNABEADS™, Thermo Fisher Scientific, Inc.) at a ratio of 1 bead/1 cell, generally as described in Example 1. Following the incubation, the activated population of T lymphocytes was resuspended and labeled with a CellTracker™ reagent (Thermo Fisher Scientific, Inc.) having a red fluorescent label. At the same time, a non-activated population (i.e., "resting" population) of CD3+T lymphocytes isolated from peripheral blood was labeled with a CellTracker™ reagent having a green fluorescent label. The activated population of T lymphocytes was then mixed with the resting population of T lymphocytes to generate a T lymphocyte mixture having a density of about $1.2\times10^6$ cells/mL, with approximately 5% of the T lymphocytes originating from the activated population.

400 microliters of the T lymphocyte mixture was flowed through a microfluidic device having a configuration generally as shown for the microfluidic device 700 in FIG. 7A, with two inlets 702/704, a post array 706 located in a first region of the flow path of the device, and two outlets 708/710. The T lymphocyte mixture was flowed into a sample inlet 702 while buffer (DPBS, 5 mM EDTA, 10 mM Hepes, 2% FBS) was flowed into a second inlet 704. The lymphocyte mixture and buffer were co-flowed through the microfluidic device, with the lymphocyte mixture provided by a pressurized reservoir at a pressure of 28 psi, and the buffer provided by a pressurized reservoir at a pressure of 30 psi. The post array had a predicted critical size ($D_c$) of about 5 microns, with a tilt angle $\varepsilon=\frac{1}{12}$ radians, 17.5 micron gaps between posts in the same column, and diamond-shaped posts having a diameter of about 70 microns. Processed cell samples were collected from both a collection outlet 708 (the "sorted sample") and a waste outlet 710 (the "waste sample").

A portion of the starting T lymphocyte mixture and each of the sorted and waste samples were analyzed on a BD FACSAria™ cell sorter (Becton Dickinson). As shown in FIG. 9A, forward scatter analysis of the starting T lymphocyte mixture identified two main peaks, one representing smaller resting T lymphocytes and a second representing larger activated T lymphocytes. Analysis of the samples based on the CellTracker™ green/CellTracker™ red labeling (FIGS. 9B-9D) also identified two main types of cells. In the starting T lymphocyte mixture (FIG. 9B), 93.5% of the cells were identified as originating from the resting T lymphocyte population (i.e., green$^{++}$/red$^-$) and 4.9% of the cells were identified as originating from the activated T lymphocyte population (i.e., green$^-$/red$^{++}$), as expected. The waste sample was similar to the starting T lymphocyte sample, though there was some depletion of cells from the activated T lymphocyte population (FIG. 9C), with 97.1% of the cells identified as originating from the resting T lymphocyte population and 1.54% of the cells identified as originating from the activated T lymphocyte population. In contrast, in the sorted population (FIG. 9D), 1.06% of the cells were identified as originating from the resting T lymphocyte population and 97.9% of the cells were identified as originating from the activated T lymphocyte population. A total of 8738 cells in the sorted sample were identified as originating from the activated T lymphocyte population, corresponding to a yield of 59% and an enrichment of 914%. In this example, enrichment was calculated as $(N^+_{out}/N^-_{out})/(N^+_{in}/N^-_{in})$, where $N^+_{out}$ is the number of activated T lymphocytes detected in the sorted sample, $N^-_{out}$ is the number of resting T lymphocytes detected in the sorted sample, $N^+_{in}$ is the number of activated T lymphocytes detected in the starting mixture, and $N^-_{in}$ is the number of resting lymphocytes detected in the starting mixture.

This experiment demonstrates that the disclosed microfluidic devices are capable of processing mixtures of activated and resting T lymphocytes so as to produce a population of cells substantially enriched for activated T lymphocytes. Many variations of the post array used to produce these results could be produced that have a critical diameter $D_c$ of about 6 microns, and any such variations would be expected to produce enriched samples of activated T lymphocytes substantially as shown above.

Example 3: Enrichment of Activated Human T Lymphocytes in a Microfluidic Device Having a Bypass Channel and a Sorting Channel Featuring Sequestration Pens CD3$^+$ human T lymphocytes isolated from peripheral blood were activated by mixing with anti-CD3/anti-CD28 magnetic beads (DYNABEADS™, Thermo Fisher Scientific, Inc.) at a ratio of 1 bead/1 cell, generally as described in Example 1. Following the incubation, the activated population of T lymphocytes was resuspended and labeled with a CellTracker™ reagent (Thermo Fisher Scientific, Inc.) having a red fluorescent label. At the same time, a non-activated population (i.e., "resting" population) of CD3+T lymphocytes isolated from peripheral blood was labeled with a CellTracker™ reagent having a green fluorescent label. The activated population of T lymphocytes was then mixed with the resting population of T lymphocytes to generate a T lymphocyte mixture having a density of about $1.0\times10^6$ cells/mL, with approximately 50% of the T lymphocytes originating from the activated population.

The T lymphocyte mixture was flowed through a microfluidic device having a configuration generally as shown for microfluidic device 715 in FIG. 7B, with a single inlet 702, a post array 706 located in a first region of a main channel of the device, a first channel 730 functioning as a bypass channel, a second channel 720 functioning as a sorting channel 720, and a single outlet 708/710 located immediately downstream of the position where the first channel 730 and the second channel 720 join back together. A plurality of sequestration pens 725 (referenced in FIG. 10) had connection regions opening to the second channel. The T lymphocyte mixture was flowed into the sample inlet 702 and through the post array 706 at a rate of about 1.0 microliter/second. The post array had a predicted critical size ($D_c$) of about 6 microns, with a tilt angle $\varepsilon=\frac{1}{12}$ radians, 25 micron gaps between posts in the same column, and triangular shaped posts having a diameter of about 50 microns (defined, in this case, an altitude of 50 microns and a base of 50 microns).

Figure 10:
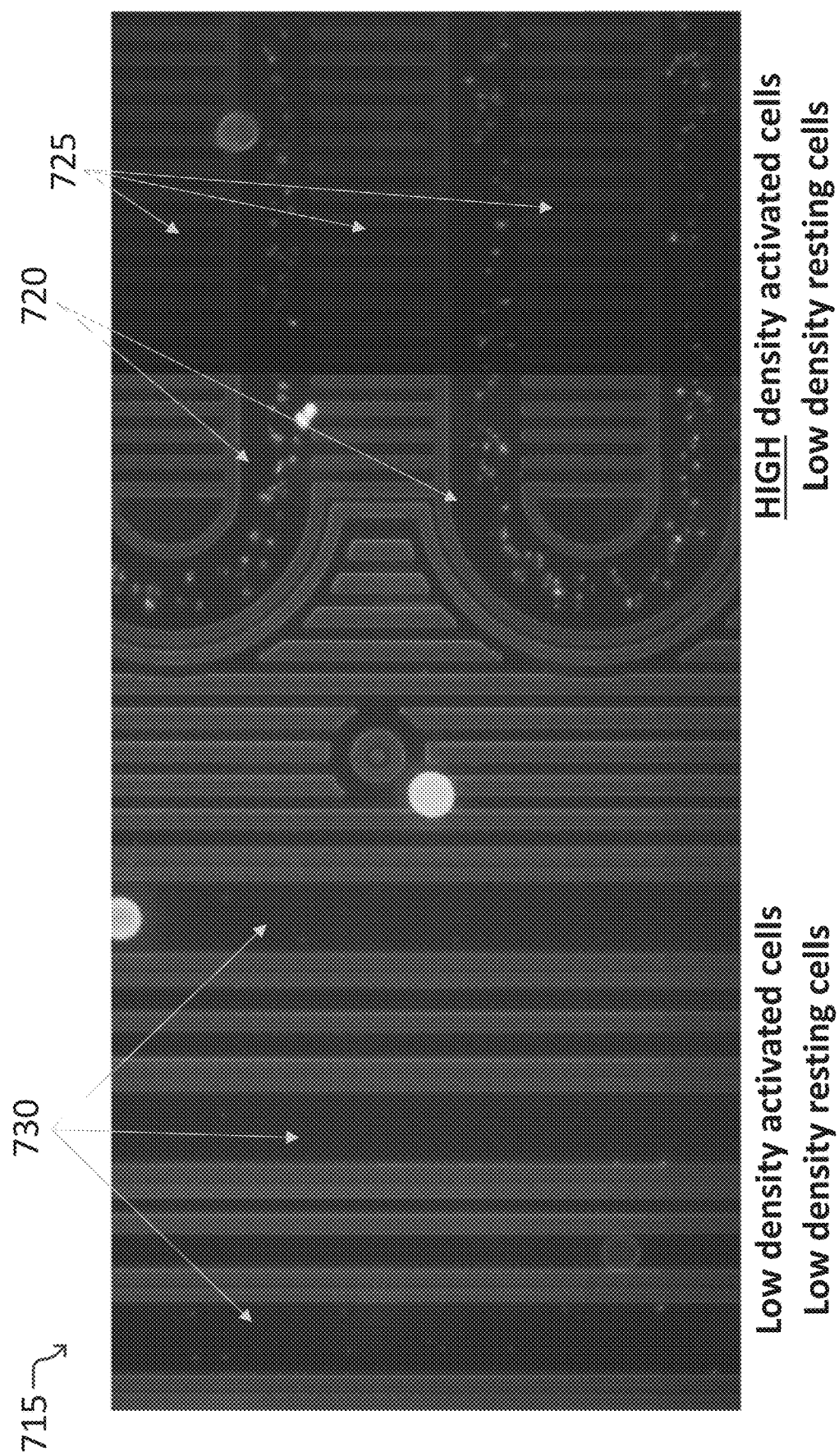
FIG. 10 is an image of a portion of a microfluidic device having first and second channels located downstream of an array of posts configured to separate cells larger than the critical size (Dc) of the post array into the second channel, where the microfluidic device further includes sequestration pens that open off of the second channel.

After flowing the T lymphocyte mixture through the post array 706, the flow rate was reduced to zero, and images such as shown in FIG. 10 were taken of the microfluidic chip. Analysis of the images showed that the density of activated T lymphocytes (stained red) in the second channel 720 was approximately $4.1 \times 10^6$ cells/mL+/−2.6%. As the starting mixture had an activated T lymphocyte density of approximately $5 \times 10^5$ cells/mL, this represented an enrichment of approximately 8-fold. In this example, enrichment was calculated as $P^+_{out}/P^+_{in}$, where $P^+_{out}$ is the concentration of activated T lymphocytes detected in the second channel and $P^+_{in}$ is the concentration of activated T lymphocytes detected in the starting mixture.

Example 4: Antigen-Specific Activation of Human T Lymphocytes Followed by Enrichment in a Microfluidic Device Step 1: A sample of peripheral blood is obtained from a healthy human donor and peripheral blood mononuclear cells (PBMCs) are harvested from the sample by leukapheresis. The PBMCs can be washed and frozen for later use, or processed immediately.

Step 2: $CD8^+$ T lymphocytes are isolated from the PBMCs using the EasySep™ Human CD8+ T Cell Enrichment kit (Stem Cell Technologies).

Step 3: $5 \times 10^6$ cells/mL of $CD8^+$ T lymphocytes are activated in an antigen-specific manner by contacting them with artificial antigen presenting cells (aAPCs) presenting MHC Class I tetramers bound to the M27L peptide of Melan-A, at a ratio of 1 T cell:1 aAPC. aAPCs have been described, for example, in PCT applications WO2013/086500, published Jun. 13, 2013, WO2014/160132, published Oct. 2, 2014, and WO2016/044530, published Mar. 24, 2016, the entire contents of which are incorporated herein by reference. Tetramers of MHC Class I molecules have been described in U.S. Pat. No. 5,635,363, the entire contents of which are incorporated herein by reference. The M27L peptide, which a tumor antigen associated with melanoma, has been described, for example, in Ho et al. (2006), Journal of Immunological Methods 310:40-52, the entire contents of which are incorporated herein by reference.

Contacting the $CD8^+$ T lymphocytes is performed in T cell culture medium containing 2 ug/mL soluble, functional grade anti-CD28 antibody (clone 15E8, Miltenyi 130-093-375). Various T cell culture media are known in the art. See, for example, Ho et al. (2006), referenced above, and International Application No. PCT/US17/22846, filed Mar. 16, 2017. The contacting step is carried out off-chip in a 96-well plate, in a 5% $CO_2$ incubator at 37° C. for a period of 3 to 4 days.

Step 4: $CD8^+$ T lymphocytes that have been activated are expected to be enlarged, and thus are selectively enriched by flowing the sample obtained at the end of the incubation in step 3 through a microfluidic device having a configuration generally as shown for microfluidic device 700 in FIG. 7A. The post array has a predicted critical size ($D_c$) of about 6 microns, with a tilt angle $\varepsilon=\frac{1}{12}$ radians, 25 micron gaps between posts in the same column, and triangular shaped posts having a diameter of about 50 microns (as described in Example 3, above). The incubated sample from step 3 is flowed through the post array of the microfluidic device at a rate of about 1.0 to about 10 microliters/sec.

Step 5: the enriched sample of activated CD8+T lymphocytes is collected from the outlet of the microfluidic device, at which point the CD8+T lymphocytes can be further expanded off chip or tested in various immunological assays.

Variations which can be incorporated into the foregoing methods include:

At step 1, the peripheral blood can be obtained from a human donor suffering from melanoma or, depending upon the antigenic peptide used in step 3, a different corresponding cancer.

At step 2, $CD8^+$ naïve T lymphocytes can be isolated from the PBMCs using the EasySep™ Human Naïve $CD8^+$ T Cell Enrichment kit (Stem Cell Technologies).

At step 2, $CD8^+$ naïve T lymphocytes can be isolated from the PBMCs using FACS and a combination of an anti-CD45RO antibody (for negative selection) and an anti-CCR7 antibody (for positive selection); additional antibodies that could be used for positive selection of $CD8^+$ naïve T lymphocytes include anti-CD45RA and/or anti-CD62L antibodies.

At step 2, CD8+T lymphocytes can be isolated from the PBMCs using FACS and an anti-CD8 antibody.

At step 3, the aAPCs present MHC Class I tetramers bound to the $WT1_{126}$ peptide of the Wilms tumor protein, which is widely expressed in a broad spectrum of leukemias, lymphomas and solid tumors. Use of the $WT1_{126}$ peptide at step 3 can be coupled with obtaining peripheral blood from a human donor suffering from any Wilms tumor-associated cancer at step 1.

At step 3, the anti-CD28 antibody can be conjugated to the aAPCs instead of providing it in the medium.

At step 3, the aAPCs can be replaced with dendritic cells (DCs) which have been pulsed with antigenic tumor-associated peptide, which can be the M27L peptide of Melan-A, the $WT1_{126}$ peptide of the Wilms tumor protein, or some other tumor-associated peptide. Methods of preparing such DCs and their use in stimulating CD8+T lymphocytes is known in the art. See, for example, Ho et al. (2006) and International Application No. PCT/US17/22846, filed Mar. 16, 2017, both of which are referred to above.

At step 4, the sample obtained after the incubation of step 3 is flowed through the post array of a microfluidic device having a configuration generally as shown for microfluidic device 715 in FIG. 7B. The post array has a predicted critical size ($D_c$) of about 6 microns, with a tilt angle $\varepsilon=\frac{1}{12}$ radians, 25 micron gaps between posts in the same column, and triangular shaped posts having a diameter of about 50 microns (as described in Example 3, above), and the microfluidic device includes a DEP configuration. The incubated sample of step 3 is flowed through the post array at a rate of about 0.1 microliters/second until the sorting channel 720 is filled with sorted T lymphocytes, at which time the flow is stopped. Individual T lymphocytes are selected and moved to corresponding sequestration pens 725, whereupon the isolated T lymphocytes are grown into clonal populations of cells. The cloning of activated T lymphocytes within a microfluidic device in this manner has been described, for example, in International Application No. PCT/US17/22846, filed Mar. 16, 2017, referred to above. Once cloned, one or more cells from select T cell clones can be exported from the microfluidic device for subsequent analysis, which may include TCR sequencing to identify antigen-specific TCRs.

Just prior to step 4, the incubated sample of step 3 can be contacted with fluorescently-labeled soluble MHC Class I tetramers bound to the M27L peptide of Melan-A (or other antigenic peptide, as appropriate), to facilitate the labeling and identification of antigen-specific T lymphocytes in the sorting channel 720 of microfluidic device 715. Such labeling and identification can be used to select individual T lymphocytes for movement into a sequestration pen 725 and subsequent cloning.

Alternatively, following the cloning of individual T lymphocytes in the sequestration pens 725, fluorescently-labeled soluble MHC Class I tetramers bound to the M27L peptide of Melan-A (or other antigenic peptide, as appropriate) can be flowed into the sorting channel 720 of microfluidic device 715 and allowed to diffuse into the sequestration pens 725, whereupon antigen-specific T lymphocyte clones can be labeled and identified. Such labeling and identification can be used to select T lymphocytes clones for export and subsequent analysis, as discussed above.

At step 5, the enriched sample of activated CD8+T lymphocytes that is collected from the outlet of the microfluidic device 700 can be used to treat a patient suffering from melanoma. This variation can be practiced with the variation of step 1 in which a subject suffering from melanoma is the peripheral blood donor. The subject the is the peripheral blood donor can also be the patient that is treated with the enriched sample of activated $CD8^+$ T lymphocytes. Optionally, the enriched sample of activated CD8+T lymphocytes that is collected from the outlet of the microfluidic device 700 can be expanded using a rapid expansion protocol (REP) prior to being introduced into the patient suffering from melanoma. REPs are known in the art. See, for example, Ho et al. (2006), referenced above.

LISTING OF EMBODIMENTS

Embodiment 1

A method of producing a sample enriched for activated T lymphocytes using a microfluidic device, the microfluidic device comprising a flow path having a first region comprising a first array of posts, the method comprising: flowing a fluid sample comprising a mixture of activated and resting T lymphocytes through the first region of the flow path of the microfluidic device, wherein: the direction of fluid flow in the first region of the flow path defines a first direction; the posts in the first array are arranged in rows and columns; the rows of posts in the first array define a first array direction that differs from the first direction of the first region by a tilt angle ($\epsilon$), and the columns of posts in the first array repeat periodically with a periodicity equal to $1/\epsilon$, wherein a is measured in radians; adjacent posts in each respective column in the first array are separated by gaps through which fluid of the fluid sample can flow generally transversely with respect to the columns, wherein a majority of the gaps have a characteristic size that corresponds to a primary gap size of the first array, and the first array is characterized by a critical size ($D_c$) of about 4 microns to about 10 microns.

Embodiment 2

The method of embodiment 1, wherein the first region of the flow path is a defined by a main channel having a width, and wherein the first array of posts extends across the entire width of the main channel.

Embodiment 3

The method of embodiment 1 or 2, wherein the first array is characterized by a Dc of about 4 microns to about 5 microns, about 4.5 microns to about 5.5 microns, about 5 microns to about 6 microns, about 5.5 microns to about 6.5 microns, about 6 microns to about 7 microns, about 6.5 microns to about 7.5 microns, about 7 microns to about 8 microns, about 7.5 microns to about 8.5 microns, about 8 microns to about 9 microns, about 8.5 microns to about 9.5 microns, about 9 microns to about 10 microns, or any range defined by two of the foregoing endpoints.

Embodiment 4

The method of embodiment 1 or 2, wherein the first array is characterized by a $D_c$ of about 4 microns to about 7 microns.

Embodiment 5

The method of embodiment 1 or 2, wherein the first array is characterized by a $D_c$ of about 7 microns to about 10 microns.

Embodiment 6

The method of embodiment 1 or 5, wherein the first array has a tilt angle ε of about ⅓ radians to about 1/100 radians.

Embodiment 7

The method of any one of embodiments 1 to 5, wherein the first array has a tilt angle ε of about ⅕ radians to about 1/30 radians.

Embodiment 8

The method of any one of embodiments 1 to 5, wherein the first array has a tilt angle ε of about 1/10 radians to about 1/16 radians.

Embodiment 9

The method of any one of embodiments 1 to 8, wherein the primary gap size of the first array is about 15 microns to about 25 microns.

Embodiment 10

The method of any one of embodiments 1 to 8, wherein the primary gap size of the first array is about 25 microns to about 40 microns.

Embodiment 11

The method of any one of embodiments 1 to 10, wherein the posts of the first array have a diameter of about 30 microns to about 100 microns (e.g., about 40 microns to about 85 microns, or about 50 microns to about 70 microns).

Embodiment 12

The method of embodiments 10 or 11, wherein the posts of the first array have a diameter that is larger than the primary gap size (e.g., 1.5 to 5 times larger).

Embodiment 13

The method of embodiments 10 or 11, wherein the posts of the first array have a diameter that is two to four times larger than the primary gap size.

Embodiment 14

The method of any one of embodiments 1 to 13, wherein the columns of the first array are arranged transversely with respect to the first direction of the first region.

Embodiment 15

The method of any one of embodiments 1 to 14, wherein the posts of the first array have a rounded shape in cross-section (e.g., circular or ellipsoidal shape).

Embodiment 16

The method of any one of embodiments 1 to 14, wherein the posts of the first array have a polygonal shape in cross-section (e.g., a triangular, square, rhomboid, or parallelogram shape).

Embodiment 17

The method of embodiments 15 or 16, wherein the posts of the first array all have the same orientation, and wherein the orientation is such that no axis of symmetry in the cross-sectional shape of the posts is parallel to an axis defined by the first direction.

Embodiment 18

The method of any one of embodiments 1 to 17, wherein the posts of the first array comprise a silicone polymer.

Embodiment 19

The method of any one of embodiments 1 to 18, wherein the first region of the flow path comprises a first lateral wall and a second lateral wall which together define the first direction, wherein all gaps between adjacent posts in the columns of the first array are equal to the primary gap size of the first array with the exception that the size of the gaps between adjacent posts of the same column that are most proximal to either the first or second lateral walls may deviate from the primary gap size, and wherein the deviations in gap sizes between posts in the first array reduce boundary irregularities in the flow of fluid sample through the first array otherwise caused by the first and second lateral walls.

Embodiment 20

The method of any one of embodiments 1 to 19, wherein the flow path of the microfluidic device comprises a second region configured to receive the fluid sample after the fluid sample passes through the first region of the microfluidic device, the second region having a divider that separates the second region into a first channel that receives a first portion of the fluid sample and a second channel that receives a second portion of the fluid sample, and wherein the divide of the second region is positioned such T lymphocytes having a diameter greater than $D_c$ are enriched, relative to the fluid sample, in the second portion of the fluid sample.

Embodiment 21

The method of embodiment 20, wherein T lymphocytes having a diameter less than $D_c$ are predominantly located in the first portion of the fluid sample.

Embodiment 22

The method of embodiment 20 or 21, wherein the first portion of the fluid sample comprises at least 50% of the fluid sample (e.g., at least 55%, 60%, 65%, 70%, 75%, 80%, 85%, 90%, or more).

Embodiment 23

The method of embodiment 20 or 21, wherein the first portion of the fluid sample comprises about 85% to about 95% of the fluid sample.

Embodiment 24

The method of any one of embodiments 20 to 23, wherein the first channel and the second channel are configured such that a pressure differential across the first channel is equal to a pressure differential across the second channel.

Embodiment 25

The method of any one of embodiments 20 to 24, wherein the first channel comprises a first length and the second channel comprises a second length, and wherein the second length is larger than the first length (e.g., wherein the second length of the second channel is at least 5 times longer than the first length of the first channel).

Embodiment 26

The method of any one of embodiments 20 to 25, wherein the microfluidic device comprises at least one sequestration pen having a connection region with a proximal opening to the second channel, and further wherein the at least one sequestration pen has an isolation region that has a volume large enough to hold at least one T lymphocyte (e.g., a plurality of T lymphocytes).

Embodiment 27

The method of embodiment 26, wherein the microfluidic device comprises a plurality of sequestration pens, each having a connection region with a proximal opening to the second channel of the second region, and each having an isolation region that has a volume large enough to hold at least one T lymphocyte (e.g., a plurality of T lymphocytes).

Embodiment 28

The method of embodiment 26 or 27, wherein the sequestration pen, or each sequestration pen of the plurality, has a volume of about 250 pL to about 3 nL (e.g., about 250 pL to about 750 pL, about 400 pL to about 900 pL, about 500 pL to about 1.5 nL, about 1 nL to about 2 nL, about 1.5 nL to about 2.5 nL, about 2 nL to about 3 nL, or any range defined by two of the foregoing endpoints).

Embodiment 29

The method of any one of embodiments 20 to 28, wherein T lymphocytes having a $CD8^+$, $CD45\ RO^+/RA^-$, $CCR7^-$, $CD62L^-$ phenotype are enriched in the second portion of the fluid sample.

Embodiment 30

The method of any one of embodiments 20 to 28, wherein T lymphocytes having a $CD8^+$, $CD45\ RO^+/RA^-$, $CCR7^+$, $CD62L^-$ phenotype are enriched in the second portion of the fluid sample.

Embodiment 31

The method of any one of embodiments 1 to 30, wherein the first region has a length of about 5 mm to about 15 mm.

Embodiment 32

The method of any one of embodiments 1 to 31, wherein the fluid sample is flowed through the first region of the flow path at a rate of about 0.01 microliters/second to about 10 microliters/second (e.g., about 0.001 to about 0.01 microliters/second, about 0.005 to about 0.05 microliters/second, about 0.01 to about 0.1 microliters/second, about 0.05 to about 0.5 microliters/second, about 0.1 to about 1.0 microliters/second, about 0.5 to about 5 microliters/second, about 1.0 to about 10 microliters/second, about 5 to about 50 microliters/second, about 10 to about 100 microliters/second, about 15 to about 50 microliters/second, about 25 to about 75 microliters/second, about 50 to about 100 microliters/second, or any range defined by two of the foregoing endpoints).

Embodiment 33

The method of any one of embodiments 20 to 32, wherein the second channel comprises a first sub-region comprising a second array of posts, wherein flowing the fluid sample through the first region of the flow path causes the second portion of the fluid sample, along with any cells contained therein, to flow through the second array of posts in the first sub-region, and further wherein: the direction of fluid flow in the first sub-region of the second channel defines a second direction; the posts in the second array are arranged in rows and columns; the rows of post in the second array define a second array direction that differs from the second direction by a tilt angle ($\varepsilon'$), and the columns of posts in the second array repeat periodically with a periodicity equal to $1/\varepsilon'$, wherein $\varepsilon'$ is measured in radians; adjacent posts in each respective column in the second array are separated by gaps through which fluid of the second portion of the fluid sample can flow generally transversely with respect to the columns, wherein a majority of the gaps have a characteristic size that corresponds to a secondary gap size of the second array, and the second array is characterized by a critical size ($D_c$) of about 4 microns to about 10 microns.

Embodiment 34

The method of embodiment 33, wherein the second channel has a width, and wherein the second array of posts extends across the entire width of the second channel.

Embodiment 35

The method of embodiment 33 or 34, wherein the second array is characterized by a Dc of about 4 microns to about 5 microns, about 4.5 microns to about 5.5 microns, about 5 microns to about 6 microns, about 5.5 microns to about 6.5 microns, about 6 microns to about 7 microns, about 6.5 microns to about 7.5 microns, about 7 microns to about 8 microns, about 7.5 microns to about 8.5 microns, about 8 microns to about 9 microns, about 8.5 microns to about 9.5 microns, about 9 microns to about 10 microns, or any range defined by two of the foregoing endpoints.

Embodiment 36

The method of embodiment 35, wherein the second array of posts is characterized by a $D_c$ of about 4 microns to about 7 microns.

Embodiment 37

The method of embodiment 35, wherein the second array of posts is characterized by a $D_c$ of about 7 microns to about 10 microns.

Embodiment 38

The method of any one of embodiments 33 to 37, wherein the second array has a tilt angle $\varepsilon$ of about $\frac{1}{3}$ radians to about $\frac{1}{100}$ radians.

Embodiment 39

The method of any one of embodiments 33 to 37, wherein the second array has a tilt angle $\varepsilon'$ of about $\frac{1}{5}$ radians to about $\frac{1}{30}$ radians.

Embodiment 40

The method of any one of embodiments 33 to 37, wherein the second array has a tilt angle $\varepsilon'$ of about $\frac{1}{10}$ radians to about $\frac{1}{16}$ radians.

Embodiment 41

The method of any one of embodiments 33 to 40, wherein the secondary gap size of the second array is about 15 microns to about 25 microns.

Embodiment 42

The method of any one of embodiments 33 to 40, wherein the secondary gap size of the second array is about 25 microns to about 40 microns.

Embodiment 43

The method of any one of embodiments 33 to 42, wherein the posts of the second array have a diameter of about 30 microns to about 100 microns (e.g., about 40 microns to about 85 microns, or about 50 microns to about 70 microns).

Embodiment 44

The method of embodiment 41 or 42, wherein the posts of the second array have a diameter that is larger than the secondary gap size (e.g., 1.5 to 5 times larger).

Embodiment 45

The method of embodiment 41 or 42, wherein the posts of the second array have a diameter that is two to four times larger than the secondary gap size.

Embodiment 46

The method of any one of embodiments 33 to 45, wherein the columns of the second array are arranged transversely with respect to the second direction of the first sub-region of the second channel.

Embodiment 47

The method of any one of embodiments 33 to 46, wherein the posts of the second array have a rounded shape in cross-section (e.g., circular or ellipsoidal shape).

Embodiment 48

The method of any one of embodiments 33 to 46, wherein the posts of the second array have a polygonal shape in cross-section (e.g., a triangular, square, rhomboid, or parallelogram shape).

Embodiment 49

The method of embodiment 47 or 48, wherein the posts of the second array all have the same orientation, and wherein the orientation is such that no axis of symmetry in the cross-sectional shape of the posts is parallel to an axis defined by the second direction.

Embodiment 50

The method of any one of embodiments 33 to 49, wherein the posts of the second array comprise a silicone polymer.

Embodiment 51

The method of any one of embodiments 33 to 50, wherein the first sub-region of the second channel comprises a third lateral wall and a fourth lateral wall which together define the second direction, wherein all gaps between adjacent posts in the columns of the second array are equal to the secondary gap size of the second array with the exception that the size of the gaps between adjacent posts of the same column that are most proximal to either the third or fourth lateral walls may deviate from the secondary gap size, and wherein the deviations in gap sizes between posts in the second array reduce boundary irregularities in the flow of the second portion of the fluid sample through the second array otherwise caused by the third and fourth lateral walls.

Embodiment 52

The method of any one of embodiments 33 to 51, wherein the second channel comprises a second sub-region configured to receive the second portion of the fluid sample after it passes through the first sub-region, the second sub-region having a divide that separates the second channel into a third channel that receives a first sub-portion of fluid from the second portion of the fluid sample and a fourth channel that receives a second sub-portion of fluid from the second portion of the fluid sample, and wherein the divide of the second sub-region is positioned such that T lymphocytes having a diameter greater than $D_c$ are enriched, relative to the second portion of the fluid sample, in the second sub-portion of fluid.

Embodiment 53

The method of embodiment 52, wherein T lymphocytes having a diameter less than $D_c$ are predominantly located in the first sub-portion of fluid.

Embodiment 54

The method of embodiment 52, wherein the first sub-portion of fluid comprises at least 50% of the second portion of the fluid sample (e.g., at least 55%, 60%, 65%, 70%, 75%, 80%, 85%, 90%, or more).

Embodiment 55

The method of embodiment 52, wherein the first sub-portion of fluid comprises about 85% to about 95% of the second portion of the fluid sample.

Embodiment 56

The method of any one of embodiments 52 to 55, wherein the third channel and the fourth channel are configured such that a pressure differential across the third channel is equal to a pressure differential across the fourth channel.

Embodiment 57

The method of embodiment 56, wherein the third channel comprises a third length and the fourth channel comprises a fourth length, and wherein the fourth length is larger than the third length.

Embodiment 58

The method of embodiment 57, wherein the fourth length is at least 5 times longer than the third length.

Embodiment 59

The method of any one of embodiments 52 to 58, wherein the microfluidic device comprises at least one sequestration pen having a connection region with a proximal opening to the third channel or the fourth channel, and further wherein the at least one sequestration pen has an isolation region that has a volume large enough to hold at least one T lymphocyte (e.g., a plurality of T lymphocytes).

Embodiment 60

The method of any one of claims 42 to 45, wherein the microfluidic device comprises a plurality of sequestration pen, each sequestration pen of the plurality having a connection region with a proximal opening to the third channel (or the fourth channel) and an isolation region that has a volume large enough to hold at least one T lymphocyte (e.g., a plurality of T lymphocytes).

Embodiment 61

The method of embodiment 59 or 60, wherein the sequestration pen, or each sequestration pen of the plurality, has a volume of about 250 pL to about 3 nL (e.g., about 250 pL to about 750 pL, about 400 pL to about 900 pL, about 500 pL to about 1.5 nL, about 1 nL to about 2 nL, about 1.5 nL to about 2.5 nL, about 2 nL to about 3 nL, or any range defined by two of the foregoing endpoints).

Embodiment 62

The method of any one of embodiments 1 to 61, wherein the fluid sample is a peripheral blood sample obtained from a subject or a sample derived therefrom. (e.g., PBMCs)

Embodiment 63

The method of embodiment 62, wherein the fluid sample is a peripheral blood sample that has been depleted at least one non-T lymphocyte cell type (e.g., myeloid cells, such as monocytes, macrophages, neutrophils, basophils, eosinophils, erythrocytes, dendritic cells, megakaryocytes, and platelets, B lymphocytes, natural killer (NK) cells, stem cells, or any combination thereof).

Embodiment 64

The method of embodiment 62 or 63, wherein the fluid sample is a peripheral blood sample that has been enriched for $CD8^+$ T lymphocytes.

Embodiment 65

The method of embodiment 64, wherein the fluid sample has been depleted of effector T lymphocytes ($T_{EFF}$) and/or memory T lymphocytes ($T_{CM}$). (e.g., cells having a $CD45RO^+$ phenotype, optionally in combination with $PD-1^+$, $PD-L1^+$, $CD137^+$, or any combination thereof or, alternatively in combination with $CCR7^+$ and/or $CD62L^+$).

Embodiment 66

The method of embodiment 64 or 65, wherein the fluid sample has been enriched for naïve T lymphocytes ($T_{naïve}$) or cells having a $CD45RA^+$ phenotype (optionally in combination with $CCR7^+$ and/or $CD62L^+$).

Embodiment 67

The method of embodiment 64 or 65, wherein the fluid sample has been enriched for central memory T lymphocytes ($T_{CM}$) or cells having a $CD45RO^+$ phenotype in combination with a $CCR7^+$ and/or $CD62L^+$ phenotype.

Embodiment 68

The method of embodiment 62 or 63, further comprising: obtaining a sample of peripheral blood or a sample derived therefrom, wherein the peripheral blood originates from a human subject; and generating the fluid sample from the sample of peripheral blood or the sample derived therefrom.

Embodiment 69

The method of embodiment 68, wherein generating the fluid sample comprises: depleting the peripheral blood sample, or the sample derived therefrom, of at least one non-T lymphocyte cell type; and/or enriching the peripheral blood sample, or the sample derived therefrom, for $CD8^+$ T lymphocytes.

Embodiment 70

The method of embodiment 69, wherein the enriching step comprises enriching the peripheral blood sample, or the sample derived therefrom, for $CD8^+$ naïve T lymphocytes or cells having a $CD45RA^+$ phenotype (optionally in combination with $CCR7^+$ and/or $CD62L^+$).

Embodiment 71

The method of any one of embodiments 1 to 61, wherein the fluid sample comprises cells isolated from a solid tumor sample of a subject.

Embodiment 72

The method of embodiment 71, wherein the solid tumor sample is a fine needle aspirate (FNA).

Embodiment 73

The method of embodiment 71, wherein the solid tumor sample is a biopsy.

Embodiment 74

The method of any one of embodiments 71 to 73, wherein the solid tumor is a breast cancer, genitourinary cancer (e.g., a cancer originating in the urinary tract, such as in the kidney (e.g., renal cell carcinoma), ureter, bladder, or urethra; cancer of the male reproductive tract (e.g., testicular cancer, prostate cancer, or a cancer of the seminal vesicles, seminal ducts, or penis); or of the female reproductive tract (e.g., ovarian cancer, uterine cancer, cervical cancer, vaginal cancer, or a cancer of the fallopian tubes)), a cancer of the nervous system (e.g., neuroblastoma), intestinal cancer (e.g., colorectal cancer), lung cancer, melanoma, or another type of cancer.

Embodiment 75

The method of any one of embodiments 71 to 73, wherein the solid tumor is a medullary breast cancer.

Embodiment 76

The method of any one of embodiments 71 to 73, wherein the solid tumor is mesothelioma.

Embodiment 77

The method of any one of embodiments 71 to 73, wherein the solid tumor is a melanoma.

Embodiment 78

The method of any one of embodiments 71 to 77, wherein the cells isolated from the solid tumor sample have been depleted of at least one non-T lymphocyte cell type (e.g., myeloid cells, such as monocytes, macrophages, neutrophils, basophils, eosinophils, erythrocytes, dendritic cells, megakaryocytes, and platelets, B lymphocytes, natural killer (NK) cells, stem cells, or any combination thereof).

Embodiment 79

The method of any one of embodiments 71 to 78, wherein the cells isolated from the solid tumor sample have been enriched for CD8⁺ T lymphocytes.

Embodiment 80

The method embodiment 79, wherein the cells isolated from the solid tumor sample have been depleted of T lymphocytes having a CD4+ phenotype and/or cells having a CD45RA⁺ phenotype (optionally in combination with a CCR7⁺ and/or CD62L+ phenotype).

Embodiment 81

The method of any one of embodiments 1 to 80, further comprising: contacting the T lymphocytes in the fluid sample with an activating agent.

Embodiment 82

The method of embodiment 81, wherein the T lymphocytes are contacted with the activating agent at least prior to flowing the fluid sample through the first region of the flow path of the microfluidic device.

Embodiment 83

The method of embodiment 81, wherein the T lymphocytes in the fluid sample are contacted with activating agent after the fluid sample is flowed through the first region of the flow path of the microfluidic device.

Embodiment 84

The method of embodiment 83, wherein the T lymphocytes are contacted with activating agent after being moved into sequestration pens (e.g., sequestration pens having a connection region with a proximal opening to the second channel, third channel, or fourth channel).

Embodiment 85

The method any one of embodiments 81 to 84, wherein the T lymphocytes in the fluid sample are contacted with the activating agent for a period of at least one hour prior to flowing the fluid sample through the first region of the flow path of the microfluidic device.

Embodiment 86

The method of any one of embodiments 81 to 85, wherein the T lymphocytes in the fluid sample are contacted with the activating agent for a period of at least 24 hours prior to flowing the fluid sample through the first region of the flow path of the microfluidic device (e.g., at least 36 hours, at least 48 hours, at least 60 hours, at least 72 hours, at least 84 hours, at least 96 hours, at least 108 hours, at least 120 hours, or any range of time defined by two of the foregoing values).

Embodiment 87

The method of any one of embodiments 81 to 86, wherein the activating agent comprises artificial antigen presenting cells (aAPCs), and wherein the aAPCs comprise MHC Class I molecules that are complexed with an antigenic peptide (e.g., a tumor associated-peptide).

Embodiment 88

The method embodiment 87, wherein the aAPCs further comprise a CD28 agonist. (e.g., an anti-CD28 agonist antibody).

Embodiment 89

The method of any one of embodiments 81 to 86, wherein the activating agent comprises dendritic cells (DCs).

Embodiment 90

The method of embodiment 89, wherein the DCs and the T lymphocytes of the fluid sample are autologous cells.

Embodiment 91

The method of embodiment 89 or 90, wherein the DCs are pulsed with an antigenic peptide prior to contacting the T lymphocytes in the fluid sample.

Embodiment 92

The method of embodiment 87, 88, or 91, wherein the antigenic peptide is identified in or isolated from tumor cells that are autologous with the T lymphocytes of the fluid sample. (Alternatively, the antigenic peptide can be identified in or isolated from a pathogen, such as a bacterial, fungal, parasitic, or viral pathogen).

Embodiment 93

The method of embodiment 87, 88, or 91, wherein the antigenic peptide is identified through genomic analysis of tumor cells (e.g., tumor cells that are autologous with the T lymphocytes of the fluid sample).

Embodiment 94

The method of any one of embodiments 20 to 94, further comprising: stopping the flow of the fluid sample through the flow path of the microfluidic device after the fluid sample has passed through the first region of the flow path and into the second channel of the microfluidic device (or the third or fourth channel of the microfluidic device).

Embodiment 95

The method of embodiment 94, further comprising: introducing at least one activated T lymphocyte into a sequestration pen.

Embodiment 96

The method of embodiment 94, further comprising: introducing at least one activated T lymphocyte into each of a plurality of sequestration pens.

Embodiment 97

The method of embodiment 95 or 96, wherein the sequestration pen or the sequestration pens of the plurality each have a connection region with a proximal opening to the second channel of the flow path of the microfluidic device (or to the third or fourth channel of the flow path of the microfluidic device).

Embodiment 98

The method of any one of embodiments 94 to 97, wherein the microfluidic device comprises a substrate having a dielectrophoresis (DEP) configuration, and wherein introducing the at least one T lymphocyte into the sequestration pen (or each sequestration pen of the plurality) comprises using a DEP force to select and move the at least one T lymphocyte into the sequestration pen (or each sequestration pen of the plurality).

Embodiment 99

The method of embodiment 98, wherein the at least one T lymphocyte is selected, at least in part, because its cell surface is $CD8^+$ (and/or has a TCR that specifically detects an antigen of interest).

Embodiment 100

The method of any one of embodiments 94 to 97, wherein introducing the at least one T lymphocyte into the sequestration pen (or each sequestration pen of the plurality) comprises tilting the microfluidic device such that gravity pulls the at least one T lymphocyte into the sequestration pen (or each sequestration pen of the plurality).

Embodiment 101

The method of any one of embodiments 94 to 100, wherein after introducing the at least on T lymphocyte into the sequestration pen (or each sequestration pen of the plurality), culture medium is perfused through the flow path of the microfluidic device for a period of at least 24 hours (e.g., at least 48 hours, at least 72 hours, at least 96 hours, or longer).

Embodiment 102

The method of any one of embodiments 94 to 101, wherein the at least one T lymphocyte is contacted with an activating agent after being introduced into the sequestration pen (or each sequestration pen of the plurality).

Embodiment 103

The method of any one of embodiments 20 to 102, further comprising: selectively exporting a population of T lymphocytes from the second channel (or the third or fourth channel) of the flow path of the microfluidic device, wherein the population of T lymphocytes is exported separately from any cells or T lymphocytes that have flowed through the first channel of the second region of the flow path of the microfluidic device.

Embodiment 104

The method of embodiment 103, wherein the population of T lymphocytes are exported from a third channel of a second subregion of a second channel of a second region of the flow path of the microfluidic device, and wherein the population of T lymphocytes is exported separately from any cells or T lymphocytes that have flowed through a fourth channel of the second subregion of the second channel.

Embodiment 105

The method of any one of embodiments 1 to 104, wherein prior to flowing the fluid through the first region of the flow path of the microfluidic device, the flow region of the microfluidic device is treated with a blocking solution comprising a blocking agent that bonds to an inner surface of the microfluidic device (e.g., the surfaces of a channel and/or any sequestration pens)

Embodiment 106

The method of embodiment 105, wherein the blocking solution comprises serum, BSA, or a polymer (e.g., a polymer comprising polyethylene glycol (PEG) and/or polypropylene glycol (PPG)).

Embodiment 107

The method of any one of embodiments 1 to 106, wherein the microfluidic device comprises an inner surface that comprises a coating material.

Embodiment 108

The method of embodiment 107, wherein the coating material comprises fluoroalkane moieties.

Embodiment 109

The method of embodiment 107, wherein the coating material comprises carboxylic acid moieties, saccharide moieties (e.g., dextran) or polyethylene glycol (PEG) moieties.

Embodiment 110

The method of any one of embodiments 1 to 109, wherein flowing the fluid sample through the first region of the flow path of the microfluidic device produces a sorted sample that is enriched in activated T lymphocytes, and wherein the enrichment is at least 2-fold (e.g., at least 3-fold, at least 4-fold, at least 5-fold), at least 6-fold, at least 7-fold, at least 8-fold, at least 9-fold, at least 10-fold, or greater).

Embodiment 111

A microfluidic device comprising: a flow path having a first region comprising a first array of posts, wherein: the first region comprises a first lateral wall and a second lateral wall which together define a general direction of fluid flow in the first region of the flow path, the general direction corresponding to a first direction of the first region; the posts in the first array are arranged in rows and columns; the rows of posts in the first array define a first array direction that differs from the first direction of the first region by a tilt angle ($\varepsilon$), and the columns of posts in the first array repeat periodically with a periodicity equal to $1/\varepsilon$, where $\varepsilon$ is measured in radians; adjacent posts in each respective column in the first array are separated by gaps through which fluid of a fluid sample can flow generally transversely with respect to the columns, wherein a majority of the gaps have a characteristic size that corresponds to a primary gap size of the first array, and the first array is characterized by a critical size ($D_c$) of about 4 microns to about 10 microns.

Embodiment 112

The device of embodiment 111, wherein the first region of the flow path is a main channel having a width defined by the first and second lateral walls, and wherein the first array of posts extends across the entire width of the main channel.

Embodiment 113

The device of embodiment 111 or 112, wherein the first array is characterized by a $D_c$ of about 4 microns to about 7 microns.

Embodiment 114

The device of embodiment 111 or 112, wherein the first array is characterized by a $D_c$ of about 7 microns to about 10 microns.

Embodiment 115

The device of any one of embodiments 111 to 114, wherein the first array has a tilt angle ε of about 1/3 radians to about 1/100 radians.

Embodiment 116

The device of any one of embodiments 111 to 114, wherein the first array has a tilt angle ε of about 1/5 radians to about 1/30 radians.

Embodiment 117

The device of any one of embodiments 111 to 114, wherein the first array has a tilt angle ε of about 1/10 radians to about 1/16 radians.

Embodiment 118

The device of any one of embodiments 111 to 117, wherein the primary gap size of the first array is about 15 microns to about 25 microns.

Embodiment 119

The device of any one of embodiments 111 to 117, wherein the primary gap size of the first array is about 25 microns to about 40 microns.

Embodiment 120

The device of any one of embodiments 111 to 119, wherein the posts of the first array have a diameter of about 30 microns to about 100 microns (e.g., about 40 microns to about 85 microns, or about 50 microns to about 70 microns).

Embodiment 121

The device of embodiments 118 or 119, wherein the posts of the first array have a diameter that is larger than the primary gap size (e.g., 1.5 to 5 times larger).

Embodiment 122

The device of embodiments 118 or 119, wherein the posts of the first array have a diameter that is two to four times larger than the primary gap size.

Embodiment 123

The device of any one of embodiments 111 to 122, wherein the columns of the first array are arranged transversely with respect to the first direction of the first region.

Embodiment 124

The device of any one of embodiments 111 to 123, wherein the posts of the first array have a rounded shape in cross-section (e.g., circular or ellipsoidal shape).

Embodiment 125

The device of any one of embodiments 111 to 123, wherein the posts of the first array have a polygonal shape in cross-section (e.g., a triangular, square, rhomboid, or parallelogram shape).

Embodiment 126

The device of embodiments 124 or 125, wherein the posts of the first array all have the same orientation, and wherein the orientation is such that no axis of symmetry in the cross-sectional shape of the posts is parallel to an axis defined by the first direction.

Embodiment 127

The device of any one of embodiments 111 to 126, wherein the posts of the first array comprise a silicone polymer.

Embodiment 128

The device of any one of embodiments 111 to 126, wherein all gaps between adjacent posts in the columns of the first array are equal to the primary gap size of the first array with the exception that the size of the gaps between adjacent posts of the same column that are most proximal to either the first or second lateral walls may deviate from the primary gap size, and wherein the deviations in gap sizes between posts in the first array reduce boundary irregularities in the flow of a fluid sample through the first array otherwise caused by the first and second lateral walls.

Embodiment 129

The device of any one of embodiments 111 to 128, wherein the flow path of the microfluidic device comprises a second region configured to receive a fluid sample after the fluid sample passes through the first region of the microfluidic device, the second region having a divide that separates the second region into a first channel that receives a first portion of the fluid sample and a second channel that receives a second portion of the fluid sample.

Embodiment 130

The device of embodiment 129, wherein the divide of the second region is positioned such T lymphocytes having a diameter greater than $D_c$ are enriched, relative to the fluid sample, in the second portion of the fluid sample; and T lymphocytes having a diameter less than $D_c$ are predominantly located in the first portion of the fluid sample.

Embodiment 131

The device of embodiment 129 or 130, wherein the first portion of the fluid sample comprises at least 50% of the fluid sample (e.g., at least 55%, 60%, 65%, 70%, 75%, 80%, 85%, 90%, or more).

Embodiment 132

The device of embodiment 129 or 130, wherein the first portion of the fluid sample comprises about 85% to about 95% of the fluid sample.

Embodiment 133

The device of any one of embodiments 129 to 132, wherein the first channel and the second channel are configured such that a pressure differential across the first channel is equal to a pressure differential across the second channel.

Embodiment 134

The device of any one of embodiments 129 to 133, wherein the first channel comprises a first length and the second channel comprises a second length, and wherein the second length is larger than the first length (e.g., wherein the second length of the second channel is at least 5 times longer than the first length of the first channel).

Embodiment 135

The device of any one of embodiments 129 to 134, wherein the microfluidic device comprises at least one sequestration pen having a connection region with a proximal opening to the second channel, and further wherein the at least one sequestration pen has an isolation region that has a volume large enough to hold at least one T lymphocyte (e.g., a plurality of T lymphocytes).

Embodiment 136

The device of any one of embodiments 129 to 134, wherein the microfluidic device comprises a plurality of sequestration pens, each having a connection region with a proximal opening to the second channel of the second region, and each having an isolation region that has a volume large enough to hold at least one T lymphocyte (e.g., a plurality of T lymphocytes).

Embodiment 137

The device of embodiment 135 or 136, wherein the sequestration pen or each sequestration pen of the plurality has a volume of about 250 pL to about 3 nL (e.g., about 250 pL to about 750 pL, about 400 pL to about 900 pL, about 500 pL to about 1.5 nL, about 1 nL to about 2 nL, about 1.5 nL to about 2.5 nL, about 2 nL to about 3 nL, or any range defined by two of the foregoing endpoints).

Embodiment 138

The device of any one of embodiments 111 to 137, wherein the first region has a length of about 5 mm to about 15 mm.

Embodiment 139

The device of any one of embodiments 129 to 138, wherein the second channel comprises a first sub-region comprising a second array of posts, wherein flowing the fluid sample through the first region of the flow path causes the second portion of the fluid sample, along with any cells contained therein, to flow through the second array of posts in the first sub-region of the second channel, and further wherein: the general direction of fluid flow in the first sub-region of the second channel defines a second direction; the posts in the second array are arranged in rows and columns; the rows of post in the second array define a second array direction that differs from the second direction by a tilt angle ($\varepsilon'$), and the columns of posts in the second array repeat periodically with a periodicity equal to $1/\varepsilon'$, wherein $\varepsilon'$ is measured in radians; adjacent posts in each respective column in the second array are separated by gaps through which fluid of the second portion of the fluid sample can flow generally transversely with respect to the columns, wherein a majority of the gaps have a characteristic size that corresponds to a secondary gap size of the second array, and the second array is characterized by a critical size ($D_c$) of about 4 microns to about 10 microns.

Embodiment 140

The device of embodiment 139, wherein the second channel has a width, and wherein the second array of posts extends across the entire width of the second channel.

Embodiment 141

The device of embodiment 139 or 140, wherein the first array is characterized by a Dc of about 4 microns to about 5 microns, about 4.5 microns to about 5.5 microns, about 5 microns to about 6 microns, about 5.5 microns to about 6.5 microns, about 6 microns to about 7 microns, about 6.5 microns to about 7.5 microns, about 7 microns to about 8 microns, about 7.5 microns to about 8.5 microns, about 8 microns to about 9 microns, about 8.5 microns to about 9.5 microns, about 9 microns to about 10 microns, or any range defined by two of the foregoing endpoints.

Embodiment 142

The device of embodiment 139 or 140, wherein the second array of posts is characterized by a $D_c$ of about 4 microns to about 7 microns, or wherein the second array of posts is characterized by a $D_c$ of about 7 microns to about 10 microns.

Embodiment 143

The device of any one of embodiments 139 to 142, wherein the second array has a tilt angle $\varepsilon$ of about ⅓ radians to about ¹⁄₁₀₀ radians.

Embodiment 144

The device of any one of embodiments 139 to 142, wherein the second array has a tilt angle ε' of about 1/5 radians to about 1/30 radians.

Embodiment 145

The device of any one of embodiments 139 to 144, wherein the secondary gap size of the second array is about 15 microns to about 25 microns.

Embodiment 146

The device of any one of embodiments 139 to 144, wherein the secondary gap size of the second array is about 25 microns to about 40 microns.

Embodiment 147

The device of any one of embodiments 139 to 146, wherein the posts of the second array have a diameter of about 30 microns to about 100 microns (e.g., about 40 microns to about 85 microns, or about 50 microns to about 70 microns).

Embodiment 148

The device of embodiment 145 or 146, wherein the posts of the second array have a diameter that is larger than the secondary gap size (e.g., 1.5 to 5 times larger).

Embodiment 149

The device of embodiment 145 or 146, wherein the posts of the second array have a diameter that is two to four times larger than the secondary gap size.

Embodiment 150

The device of any one of embodiments 139 to 149, wherein the columns of the second array are arranged transversely with respect to the second direction of the first sub-region of the second channel.

Embodiment 151

The device of any one of embodiments 139 to 150, wherein the posts of the second array have a rounded shape in cross-section (e.g., circular or ellipsoidal shape).

Embodiment 152

The device of any one of embodiments 139 to 150, wherein the posts of the second array have a polygonal shape in cross-section (e.g., a triangular, square, rhomboid, or parallelogram shape).

Embodiment 153

The device of embodiment 151 or 152, wherein the posts of the second array all have the same orientation, and wherein the orientation is such that no axis of symmetry in the cross-sectional shape of the posts is parallel to an axis defined by the second direction.

Embodiment 154

The device of any one of embodiments 139 to 153, wherein the posts of the second array comprise a silicone polymer.

Embodiment 155

The device of any one of embodiments 139 to 154, wherein the first sub-region of the second channel comprises a third lateral wall and a fourth lateral wall which together define the second direction, wherein all gaps between adjacent posts in the columns of the second array are equal to the secondary gap size of the second array with the exception that the size of the gaps between adjacent posts of the same column that are most proximal to either the third or fourth lateral walls may deviate from the secondary gap size, and wherein the deviations in gap sizes between posts in the second array reduce boundary irregularities in the flow of the second portion of the fluid sample through the second array otherwise caused by the third and fourth lateral walls.

Embodiment 156

The device of any one of embodiments 139 to 155, wherein the second channel comprises a second sub-region configured to receive the second portion of the fluid sample after it passes through the first sub-region, the second sub-region having a divide that separates the second channel into a third channel that receives a first sub-portion of fluid from the second portion of the fluid sample and a fourth channel that receives a second sub-portion of fluid from the second portion of the fluid sample.

Embodiment 157

The device of embodiment 156, wherein the divide of the second sub-region is positioned such that T lymphocytes having a diameter greater than $D_c$ are enriched, relative to the second portion of the fluid sample, in the second sub-portion of fluid, and wherein T lymphocytes having a diameter less than $D_c$ are predominantly located in the first sub-portion of fluid.

Embodiment 158

The device of embodiments 156 or 157, wherein the first sub-portion of fluid comprises at least 50% of the second portion of the fluid sample (e.g., at least 55%, 60/o %, 65%, 70%, 75%, 80%, 85%, 90%, or more).

Embodiment 159

The device of embodiment 156 or 157, wherein the first sub-portion of fluid comprises about 85% to about 95% of the second portion of the fluid sample.

Embodiment 160

The device of any one of embodiments 156 to 159, wherein the third channel and the fourth channel are configured such that a pressure differential across the third channel is equal to a pressure differential across the fourth channel.

Embodiment 161

The device of embodiment 160, wherein the third channel comprises a third length and the fourth channel comprises a fourth length, and wherein the fourth length is larger than the third length (e.g., wherein the fourth length is at least 5 times longer than the third length).

Embodiment 162

The device of any one of embodiments 156 to 161, wherein the microfluidic device comprises at least one sequestration pen having a connection region with a proximal opening to the third channel or the fourth channel, and further wherein the at least one sequestration pen has an isolation region that has a volume large enough to hold at least one T lymphocyte (e.g., a plurality of T lymphocytes).

Embodiment 163

The device of any one of embodiments 156 to 161, wherein the microfluidic device comprises a plurality of sequestration pens, each sequestration pen of the plurality having a connection region with a proximal opening to the third channel (or the fourth channel) and an isolation region that has a volume large enough to hold at least one T lymphocyte (e.g., a plurality of T lymphocytes).

Embodiment 164

The device of embodiment 162 or 163, wherein the sequestration pen or each sequestration pen of the plurality has a volume of about 250 pL to about 3 nL (e.g., about 250 pL to about 750 pL, about 400 pL to about 900 pL, about 500 pL to about 1.5 nL, about 1 nL to about 2 nL, about 1.5 nL to about 2.5 nL, about 2 nL to about 3 nL, or any range defined by two of the foregoing endpoints).

Embodiment 165

The device of any one of embodiments 111 to 164, wherein the microfluidic device comprises an inner surface (e.g., at least one inner surface of the first region, the second region, the first sub-region, the second sub-region, the first channel, the second channel, the third channel, the fourth channel) that comprises a coating material.

Embodiment 166

The device of embodiment 165, wherein the coating material comprises fluoroalkane moieties.

Embodiment 167

The device of embodiment 165, wherein the coating material comprises carboxylic acid moieties, saccharide moieties (e.g., dextran), or polyethylene glycol (PEG) moieties.

Embodiment 168

A composition comprising T lymphocytes sorted according to the methods of any one of embodiments 20 to 51 and 62 to 110, wherein the T lymphocytes are obtained by exporting cells from the second channel of the flow path of the microfluidic device, wherein the population of T lymphocytes is exported separately from any cells or T lymphocytes that have flowed through the first channel of the flow path of the microfluidic device.

Embodiment 169

A composition comprising T lymphocytes sorted according to the methods of any one of embodiments 52 to 110, wherein the T lymphocytes are obtained by exporting cells from the third channel (or fourth channel) of the flow path of the microfluidic device, and wherein the population of T lymphocytes is exported separately from any cells or T lymphocytes that have flowed through the fourth channel (or third channel) of the flow path of the microfluidic device

Embodiment 170

The composition of embodiment 168 or 169 further comprising a pharmaceutically acceptable carrier.

Embodiment 171

A method of treating a subject suffering from a pathogenic disorder or cancer, the method comprising administering a composition of embodiment 170.

EQUIVALENTS

The foregoing written specification is considered to be sufficient to enable one skilled in the art to practice the embodiments. The foregoing description and Examples detail certain embodiments and describes the best mode contemplated. It will be appreciated, however, that no matter how detailed the foregoing may appear in text, the embodiment may be practiced in many ways and should be construed in accordance with the appended claims and any equivalents thereof.

What is claimed:
1. A method of producing a sample enriched for activated T lymphocytes using a microfluidic device, the microfluidic device comprising a flow path having a first region comprising a first array of posts, the method comprising:
flowing a fluid sample comprising a mixture of activated and resting T lymphocytes through the first region of the flow path of the microfluidic device, wherein:
the direction of fluid flow in the first region of the flow path defines a first direction;
the posts in the first array are arranged in rows and columns;
the rows of posts in the first array define a first array direction that differs from the first direction of the first region by a tilt angle ($\varepsilon$), and the columns of posts in the first array repeat periodically with a periodicity equal to $1/\varepsilon$, wherein $\varepsilon$ is measured in radians;
adjacent posts in each respective column in the first array are separated by gaps through which fluid of the fluid sample can flow generally transversely with respect to the columns, wherein a majority of the gaps have a characteristic size that corresponds to a primary gap size of the first array, the first array is characterized by a critical size ($D_c$) of about 4 microns to about 7 microns, the first array has a tilt angle $\varepsilon$ of $1/5$ radians to $1/50$ radians, the primary gap size of the first array is 15 microns to 40 microns, and the posts of the first array have a diameter of 30 microns to 100 microns;

the flow path of the microfluidic device comprises a second region configured to receive the fluid sample after the fluid sample passes through the first region of the microfluidic device, the second region having a divider that separates the second region into a first channel that receives a first portion of the fluid sample and a second channel that receives a second portion of the fluid sample;

the divider of the second region is positioned such that T lymphocytes having a diameter greater than $D_c$ are enriched, relative to the fluid sample, in the second portion of the fluid sample; and the microfluidic device comprises at least one sequestration pen having a connection region with a proximal opening to the second channel, and further wherein the at least one sequestration pen has an isolation region that has a volume large enough to hold at least one T lymphocyte, stopping the flow of the fluid sample through the flow path of the microfluidic device after the fluid sample has passed through the first region of the flow path and into the second channel of the microfluidic device; and introducing at least one activated T lymphocyte into the at least one sequestration pen.

2. The method of claim 1, wherein the posts of the first array have a rounded shape in cross-section or a polygonal shape in cross-section.

3. The method of claim 2, wherein the posts of the first array all have the same orientation, and wherein the orientation is such that no axis of symmetry in the cross-sectional shape of the posts is parallel to an axis defined by the first direction.

4. The method of claim 1, wherein the first portion of the fluid sample comprises about 85% to about 95% of the fluid sample.

5. The method of claim 1, wherein T lymphocytes having a CD8$^+$, CD45 RO$^+$/RA$^-$, CCR7$^-$, CD62L$^-$ and/or CD8$^+$, CD45 RO$^+$/RA$^-$, CCR7$^-$, CD62L$^-$ phenotype are enriched in the second portion of the fluid sample.

6. The method of claim 1, wherein the fluid sample is flowed through the first region of the flow path at a rate of about 0.01 microliters/second to about 10 microliters/second.

7. The method of claim 1, wherein the second channel comprises a first sub-region comprising a second array of posts, wherein flowing the fluid sample through the first region of the flow path causes the second portion of the fluid sample, along with any cells contained therein, to flow through the second array of posts in the first sub-region, and further wherein:

the direction of fluid flow in the first sub-region of the second channel defines a second direction;

the posts in the second array are arranged in rows and columns;

the rows of posts in the second array define a second array direction that differs from the second direction by a tilt angle ($\epsilon'$), and the columns of posts in the second array repeat periodically with a periodicity equal to 1/$\epsilon'$, wherein $\epsilon'$ is measured in radians;

adjacent posts in each respective column in the second array are separated by gaps through which fluid of the second portion of the fluid sample can flow generally transversely with respect to the columns, wherein a majority of the gaps have a characteristic size that corresponds to a secondary gap size of the second array, and the second array is characterized by a critical size ($D_c$) of about 4 microns to about 10 microns.

8. The method of claim 7, wherein the second channel has a width, and wherein the second array of posts extends across the entire width of the second channel, wherein the second array has a tilt angle $\epsilon'$ of about 1/5 radians to about 1/30 radians, wherein the secondary gap size of the second array is about 15 microns to about 25 microns or about 25 microns to about 40 microns, wherein the posts of the second array have a diameter of about 30 microns to about 100 microns.

9. The method of claim 7, wherein the second channel comprises a second sub-region configured to receive the second portion of the fluid sample after it passes through the first sub-region, the second sub-region having a divider that separates the second channel into a third channel that receives a first sub-portion of fluid from the second portion of the fluid sample and a fourth channel that receives a second sub-portion of fluid from the second portion of the fluid sample, and wherein the divider of the second sub-region is positioned such that T lymphocytes having a diameter greater than $D_c$ are enriched, relative to the second portion of the fluid sample, in the second sub-portion of fluid.

10. The method of claim 9, wherein the first sub-portion of fluid comprises at least 50% of the second portion of the fluid sample.

11. The method of claim 1 wherein the fluid sample is a peripheral blood sample obtained from a subject or a derived sample derived therefrom.

12. The method of claim 11, wherein the fluid sample is a peripheral blood sample that has been depleted of at least one non-T lymphocyte cell type.

13. The method of claim 11, wherein the fluid sample is a peripheral blood sample that has been enriched for CD8$^+$ T lymphocytes.

14. The method of claim 13, wherein the fluid sample has been depleted of effector T lymphocytes ($T_{EFF}$) and/or the fluid sample has been enriched for naïve T lymphocytes ($T_{naïve}$), cells having a CD45RA$^+$ phenotype, central memory T lymphocytes ($T_{CM}$), or cells having a CD45RO$^+$ phenotype in combination with a CCR7$^+$ and/or CD62L$^+$ phenotype.

15. The method of claim 11, further comprising:

obtaining the peripheral blood sample or the derived sample from a human subject; and generating the fluid sample from the peripheral blood sample or the derived sample.

16. The method of claim 15, wherein generating the fluid sample comprises:

depleting the peripheral blood sample, or the sample derived therefrom, of at least one non-T lymphocyte cell type; and/or enriching the peripheral blood sample, or the sample derived therefrom, for CD8$^+$ T lymphocytes.

17. The method of claim 11, further comprising:

contacting the T lymphocytes in the fluid sample with an activating agent to create the mixture of activated and resting T lymphocytes.

18. The method of claim 17, wherein the T lymphocytes in the fluid sample are contacted with the activating agent for a period of at least 48 hours prior to flowing the fluid sample through the first region of the flow path of the microfluidic device.

19. The method of claim 17, wherein the activating agent comprises artificial antigen presenting cells (aAPCs), and wherein the aAPCs comprise WIC Class I molecules that are complexed with an antigenic peptide.

20. The method of claim 19, wherein the aAPCs further comprise a CD28 agonist.

21. The method of claim 19, wherein the antigenic peptide is identified in or isolated from a bacterial pathogen, a fungal pathogen, a parasitic pathogen, a viral pathogen, or tumor cells.

22. The method of claim 1, further comprising:
selectively exporting a population of T lymphocytes from the second channel of the flow path of the microfluidic device, wherein the population of T lymphocytes is exported separately from any cells or T lymphocytes that have flowed through the first channel of the flow path of the microfluidic device.

23. The method of claim 1, wherein the microfluidic device comprises an inner surface that comprises a coating material.

24. The method of claim 1, wherein flowing the fluid sample through the first region of the flow path of the microfluidic device produces a sorted sample that is enriched in activated T lymphocytes, and wherein the enrichment is at least 2-fold.

25. The method of claim 1, wherein the microfluidic device comprises a substrate having a dielectrophoresis (DEP) configuration, and wherein introducing the at least one activated T lymphocyte into the sequestration pen comprises using a DEP force to select and move the at least one activated T lymphocyte into the sequestration pen.

* * * * *